(12) United States Patent
Trees et al.

(10) Patent No.: US 12,354,729 B2
(45) Date of Patent: Jul. 8, 2025

(54) COGNITIVE SCREENS, MONITOR AND COGNITIVE TREATMENTS TARGETING IMMUNE-MEDIATED AND NEURO-DEGENERATIVE DISORDERS

(71) Applicant: Akili Interactive Labs, Inc., Boston, MA (US)

(72) Inventors: Jason Daniel Trees, Dedham, MA (US); Vincent Hennemand, Brookline, MA (US); Scott Charles Kellogg, Mattapoisett, MA (US); Guillaume Poirier, Arlington, MA (US)

(73) Assignee: Akili Interactive Labs, Inc., Boston, MA (US)

( * ) Notice: Subject to any disclaimer, the term of this patent is extended or adjusted under 35 U.S.C. 154(b) by 1130 days.

(21) Appl. No.: 17/013,480

(22) Filed: Sep. 4, 2020

(65) Prior Publication Data
US 2020/0402643 A1 Dec. 24, 2020

Related U.S. Application Data

(63) Continuation of application No. PCT/US2019/020508, filed on Mar. 4, 2019.
(Continued)

(51) Int. Cl.
*G16H 20/70* (2018.01)
*G16H 40/63* (2018.01)
(Continued)

(52) U.S. Cl.
CPC ............. *G16H 20/70* (2018.01); *G16H 40/63* (2018.01); *G16H 50/20* (2018.01); *G16H 50/30* (2018.01);
(Continued)

(58) Field of Classification Search
CPC ........ G16H 20/70; G16H 50/30; G16H 50/20; G16H 40/63; G16H 70/20; A61B 5/16; A61B 5/4088
See application file for complete search history.

(56) References Cited

U.S. PATENT DOCUMENTS

| 8,016,416 B1 | 9/2011 | Straus |
| 9,265,458 B2 | 2/2016 | Stack |

(Continued)

FOREIGN PATENT DOCUMENTS

| JP | 2017518856 A | 7/2017 |
| TW | 201734940 A | 10/2017 |

(Continued)

OTHER PUBLICATIONS

Neuman, M. R. "Biopotential Electrodes." The Biomedical Engineering Handbook: Second Ed. Joseph D. Bronzino; Boca Raton: CRC Press LLC, 2000 (Year: 2000).*
(Continued)

*Primary Examiner* — Pamela M. Bays
(74) *Attorney, Agent, or Firm* — Gregory Finch; Finch Paolino, LLC

(57) ABSTRACT

Systems and methods for generating a personalized cognitive treatment recommendation for an individual. The system includes one or more processors; and a memory to store processor-executable instructions. Upon execution of the instructions, the one or more processors receive parameters for at least one cognitive treatment tool; receive physiological data indicative of a condition of the individual, and/or clinical data associated with the individual; and generate the personalized cognitive treatment recommendation based on the physiological data and/or the clinical data. The recommendation includes a specification of (i) at least one first cognitive treatment tool, (ii) at least one second cognitive treatment tool different from the at least one first cognitive (Continued)

treatment tool, or (iii) both (i) and (ii). Optionally, the one or more processors receive performance data indicative of the individual's performance of at least one task associated with the at least one cognitive treatment tool of the recommendation.

20 Claims, 32 Drawing Sheets

Related U.S. Application Data

(60) Provisional application No. 62/638,299, filed on Mar. 4, 2018.

(51) Int. Cl.
 | | |
 |---|---|
 | *G16H 50/20* | (2018.01) |
 | *G16H 50/30* | (2018.01) |
 | *A61B 5/00* | (2006.01) |
 | *A61B 5/16* | (2006.01) |
 | *G16H 70/20* | (2018.01) |

(52) U.S. Cl.
 CPC .............. *A61B 5/16* (2013.01); *A61B 5/4088* (2013.01); *G16H 70/20* (2018.01)

(56) References Cited

U.S. PATENT DOCUMENTS

| 9,940,844 | B2 | 4/2018 | Gazzaley |
| 2008/0003558 | A1* | 1/2008 | Chan ..................... G09B 5/00 434/323 |
| 2009/0312817 | A1 | 12/2009 | Hogle et al. |
| 2010/0292545 | A1 | 11/2010 | Berka et al. |
| 2011/0098777 | A1 | 4/2011 | Silverstone |
| 2012/0088216 | A1 | 4/2012 | Wexler |
| 2014/0370479 | A1 | 12/2014 | Gazzaley |
| 2017/0098385 | A1 | 4/2017 | Martucci et al. |
| 2017/0228505 | A1 | 8/2017 | Allen et al. |

FOREIGN PATENT DOCUMENTS

| WO | 0205247 A2 | 1/2002 | |
| WO | 2012064999 A1 | 5/2012 | |
| WO | 2014138925 A1 | 9/2014 | |
| WO | 2015179522 A1 | 11/2015 | |
| WO | 2015192021 A1 | 12/2015 | |
| WO | 2016145372 A1 | 9/2016 | |
| WO | 2016156867 A1 | 10/2016 | |
| WO | 2017106770 A1 | 6/2017 | |
| WO | 2018017767 A1 | 1/2018 | |
| WO | 2018027080 A1 | 2/2018 | |
| WO | WO-2018039610 A1 * | 3/2018 | ............. A61B 5/021 |
| WO | 2018112103 A1 | 6/2018 | |

OTHER PUBLICATIONS

Office Action, English translation. Taiwan patent application No. 108107129. Date of mailing: Aug. 11, 2022. Taiwan Intellectual Property Office, Taipei City, TW.
Office Action, Australian patent application No. 2019229979. Date of mailing: Nov. 30, 2022. IP Australia, Woden, AU.
Extended European Search Report, EP application No. 19764469.3. Date of mailing: Mar. 7, 2022. European Patent Office, Munich, DE.
International Search Report, International application No. PCT/US2019/020508. Date of mailing: May 17, 2019. ISA/US, Alexandria, VA.
Written Opinion of the International Searching Authority, International application No. PCT/US2019/020508. Date of mailing: May 17, 2019. ISA/US, Alexandria, VA.
Office Action, English translation. Japanese patent application No. 2020-546125. Date of mailing: Jan. 13, 2023. Japan Patent Office, Tokyo, Japan.
Office Action, English translation. Taiwan patent application No. 108107129. Date of mailing: Feb. 24, 2023. Taiwan Intellectual Property Office, Taipei City, TW.
Examination Report, Canadian application No. 3093252. Date of mailing: Feb. 7, 2024. Canadian Intellectual Property Office, Gatineau, CA.
English translation, Office Action, Chinese application No. 2019800294896. Date of mailing: Jan. 31, 2024. CNIPA, Beijing, CN.
English translation, Search Report, Korean application No. 10-2020-7028297. Date of mailing: Mar. 25, 2024. KIPO, Daejeon, KR.

* cited by examiner

COGNITIVE SCREENS, MONITOR AND COGNITIVE TREATMENTS TARGETING IMMUNE-MEDIATED AND NEURO-DEGENERATIVE DISORDERS

CROSS-REFERENCE TO RELATED APPLICATIONS

This application is a continuation of PCT Patent Application No. PCT/US2019/020508 entitled "COGNITIVE SCREENS, MONITOR AND COGNITIVE TREATMENTS TARGETING IMMUNE-MEDIATED AND NEURO-DEGENERATIVE DISORDERS" filed on Mar. 4, 2019, which claims priority to and benefit from U.S. Provisional Application No. 62/638,299 entitled "COGNITIVE SCREENS, MONITOR AND COGNITIVE TREATMENTS TARGETING IMMUNE-MEDIATED AND NEURO-DEGENERATIVE DISORDERS" filed on Mar. 4, 2018, the entireties of each disclosure, including drawings, being incorporated herein at least by virtue of this reference.

FIELD OF THE DISCLOSURE

The disclosure relates to personalizing cognitive treatment, such as for immune-mediated and neuro-degenerative disorders.

BACKGROUND

There is growing concern and unmet needs related to the baseline evaluation of, the short-term and long-term monitoring of, and the treatment of cognition in individuals having a condition such as an immune-mediated or neuro-degenerative disorder. With an increased access to novel pharmacological treatments targeting the underlying inflammatory and neurodegenerative aspects of these diseases, the concerns associated with life-impairing cognitive disabilities have grown in importance. The latter led to the emergence of remediation techniques mainly accessible in clinical settings and in scarce access relative to the number of patients in need.

SUMMARY

Apparatus, systems, and methods are provided for personalizing cognitive treatments.

In an aspect, embodiments relate to a system for generating a personalized cognitive treatment recommendation for an individual. The system includes one or more processors, and a memory to store processor-executable instructions and communicatively coupled with the one or more processors. Upon execution of the processor-executable instructions by the one or more processors, the one or more processors are configured to a) receive parameters for at least one cognitive treatment tool; b) receive at least one of physiological data indicative of a condition of the individual, or clinical data associated with the individual; and c) generate the personalized cognitive treatment recommendation based on at least one of the physiological data or the clinical data. The recommendation includes a specification of (i) at least one first cognitive treatment tool, (ii) at least one second cognitive treatment tool different from the at least one first cognitive treatment tool, or (iii) both (i) and (ii).

One or more of the following features may be included with any aspect of any embodiment. The clinical data may be obtained from at least one patient registry.

The one or more processors may be further configured to receive performance data indicative of the individual's performance of at least one task associated with the at least one cognitive treatment tool of the recommendation. The personalized cognitive treatment recommendation may be further based on the received performance data.

Steps b) and c) may be repeated after the individual performs the personalized cognitive treatment recommendation, with the data received during the repetition of step b) including data collected subsequent to the individual's performance of at least one task associated with the at least one cognitive treatment tool of the recommendation.

The one or more processors may be further configured to monitor a status of the condition of the individual based on an analysis of at least one of the physiological data, the clinical data, or data indicative of an interaction of the individual with at least one cognitive monitoring tool, with data received during the repetition of step b) including data indicative of the status of the condition based on the monitoring.

Generating the personalized cognitive treatment recommendation may include using a predictive model that is trained using a plurality of training datasets, each training dataset corresponding to a previously classified individual of a plurality of individuals, and each training dataset comprising data representing the at least one indicator of the cognitive ability of the classified individual and data indicative of a diagnosis of a status or progression of the condition in the classified individual.

The predictive model may include a linear/logistic regression, principal component analysis, a generalized linear mixed model, a random decision forest, a support vector machine, and/or an artificial neural network.

The condition may include multiple sclerosis and/or lupus.

The condition may include dementia, Parkinson's disease, cerebral amyloid angiopathy, familial amyloid neuropathy, Huntington's disease, autism spectrum disorder, presence of the 16p11.2 duplication, attention deficit hyperactivity disorder, sensory-processing disorder (SPD), mild cognitive impairment, Alzheimer's disease, schizophrenia, depression, and/or anxiety.

The one or more processors may be further configured to generate an output indicative of (i) a likelihood of onset of the condition of the individual, (ii) a stage of progression of the condition, or (iii) combinations thereof.

The one or more processors may be further configured to monitor a status of the condition of the individual based on an analysis of at least one of the physiological data, the clinical data, or data indicative of an interaction of the individual with the at least one cognitive treatment tool.

The at least one cognitive treatment tool may include an interference processing tool, a spatial navigation tool, and/or an emotional processing tool.

The recommendation may include an interference processing tool, and the one or more processors may be further configured to generate a user interface. Via the user interface, a first instance of a task may be presented with an interference at the user interface, requiring a first response from the individual to the first instance of the task in the presence of the interference. Via the user interface, the first instance of the task may be presented, requiring a second response from the individual to the first instance of the task in the absence of the interference. At least one of the first instance of the task and the interference may include a computerized element. The first response from the individual to the first instance of the task and the response from the individual to the interference may be measured substantially simultaneously. Data indicative of the first response and the second response may be received The data indicative of the first response and the second response may be analyzed to compute at least one performance metric comprising at least one quantified indicator of cognitive abilities of the individual.

The one or more processors may be configured to present the task as a continuous visuo-motor tracking task, and the first instance of the task may be a first time interval of the continuous visuo-motor task. The one or more processors may be configured to present via the user interface the interference as a target discrimination interference.

The recommendation may include a spatial navigation tool, and the one or more processors may be further configured to generate a user interface. Via the user interface, a first task that requires navigation of a specified route through an environment may be presented. Via the user interface, a first indicator configured to navigate the specified route from an initial point in the environment to a target end-point with or without input from the individual may be presented. The user interface may be configured to display instructions to the individual to perform a second task, the second task requiring the individual either: (i) to navigate a reverse of at least a portion of the specified route, or (ii) to navigate at least a portion of the specified route at least one additional time. Via the user interface a second indicator configured to navigate in the environment in response to physical actions of the individual to control one of (i) a relative direction of the second indicator, or (ii) a speed of movement of the second indicator, or (iii) both (i) and (ii), to perform the second task. Measurement data may be obtained by measuring data indicative of the physical actions of the individual to control the second indicator in performing the second task. The measurement data may be analyzed to generate a performance metric for the performance of the second task, the performance metric providing an indication of the cognitive ability of the individual.

Generating the performance metric may include considering a total time taken to successfully complete the second task, a number of incorrect turns made by the second indicator, a number of incorrect directions of movement made by the second indicator, and/or a degree of deviation of the user-navigated route in the second task as compared to the specified route.

The recommendation may include an emotional processing tool, and the one or more processors may be further configured to generate a user interface. Via the user interface, a first instance of a task with an interference at the user interface is presented, requiring a first response from the individual to the first instance of the task in the presence of the interference and a response from the individual to at least one evocative element. At least one of the first instance of the task and the interference may include the at least one evocative element. The first response from the individual to the first instance of the task and the response from the individual to the at least one evocative element may be measured substantially simultaneously, providing a measure of emotional processing capabilities of the individual under emotional load. Data indicative of the first response and the response of the individual to the at least one evocative element is received. The data indicative of the first response and the response of the individual to the at least one evocative element is analyzed to compute at least one performance metric including at least one quantified indicator of cognitive abilities of the individual under emotional load.

The system may include an actuating component, and the one or more processors may be further configured to control the actuating component to effect an auditory stimulus, a tactile stimulus, or a vibrational stimulus, and the evocative element may include at least one of the auditory stimulus, the tactile stimulus, or the vibrational stimulus.

The system may include one or more sensor components, with the one or more processors being configured to control the one or more sensor components to measure the data indicative of the individual's performance of the task.

The one or more sensor components may include a gyroscope, an accelerometer, a motion sensor, a position sensor, a pressure sensor, an optical sensor, a video camera, an auditory sensor, and/or a vibrational sensor.

The system may be at least one of a virtual reality system, an augmented reality system, or a mixed reality system.

In another aspect, embodiments relate to a computer-implemented method for generating a personalized cognitive treatment recommendation for an individual. The method includes using one or more processors to execute instructions stored in one or more memory storage devices including computer executable instructions to perform operations. The operations include receive parameters for at least one cognitive treatment tool; receive at least one of physiological data indicative of a condition of the individual, or clinical data associated with the individual; and generate the personalized cognitive treatment recommendation based on at least one of the physiological data or the clinical data. The recommendation includes a specification of (i) at least one first cognitive treatment tool, (ii) at least one second cognitive treatment tool different from the at least one first cognitive treatment tool, or (iii) both (i) and (ii).

One or more of the following features may be included. The clinical data may be obtained from at least one patient registry.

The operations may further include receiving performance data indicative of the individual's performance of at least one task associated with the at least one cognitive treatment tool of the recommendation.

The personalized cognitive treatment recommendation may be further based on the received performance data.

The operations may further include repeating steps b) and c) after the individual performs the personalized cognitive treatment recommendation, with the data received during the repetition of step b) including data collected subsequent to the individual's performance of at least one task associated with the at least one cognitive treatment tool of the recommendation.

The operations may further include monitoring a status of the condition of the individual based on an analysis of at least one of the physiological data, the clinical data, or data indicative of an interaction of the individual with at least one cognitive monitoring tool, with data received during the repetition of step b) including data indicative of the status of the condition based on the monitoring.

Generating the personalized cognitive treatment recommendation may include using a predictive model that is trained using a plurality of training datasets, each training dataset corresponding to a previously classified individual of a plurality of individuals, and each training dataset comprising data representing the at least one indicator of the cognitive ability of the classified individual and data indicative of a diagnosis of a status or progression of the condition in the classified individual.

The predictive model may include a linear/logistic regression, principal component analysis, a generalized linear mixed model, a random decision forest, a support vector machine, and/or an artificial neural network.

The condition may include multiple sclerosis and/or lupus.

The condition may include dementia, Parkinson's disease, cerebral amyloid angiopathy, familial amyloid neuropathy, Huntington's disease, autism spectrum disorder, presence of the 16p11.2 duplication, attention deficit hyperactivity disorder, sensory-processing disorder (SPD), mild cognitive impairment, Alzheimer's disease, schizophrenia, depression, and/or anxiety.

The operations may further include generating an output indicative of (i) a likelihood of onset of the condition of the individual, (ii) a stage of progression of the condition, and/or (iii) combinations thereof.

The operations may further include monitoring a status of the condition of the individual based on an analysis of at least one of the physiological data, the clinical data, or data indicative of an interaction of the individual with the at least one cognitive treatment tool.

The at least one cognitive treatment tool may include at least one of an interference processing tool, a spatial navigation tool, or an emotional processing tool.

The recommendation may include an interference processing tool, and the one or more processors may be further configured to generate a user interface. Via the user interface, a first instance of a task may be presented with an interference at the user interface, requiring a first response from the individual to the first instance of the task in the presence of the interference. Via the user interface, the first instance of the task may be presented, requiring a second response from the individual to the first instance of the task in the absence of the interference. At least one of the first instance of the task and the interference may include a computerized element. The first response from the individual to the first instance of the task and the response from the individual to the interference may be measured substantially simultaneously. Data indicative of the first response and the second response may be received The data indicative of the first response and the second response may be analyzed to compute at least one performance metric comprising at least one quantified indicator of cognitive abilities of the individual.

The task may be presented as a continuous visuo-motor tracking task, and the first instance of the task may be a first time interval of the continuous visuo-motor task.

The interference may be presented as a target discrimination interference.

The recommendation may include a spatial navigation tool, and the one or more processors may be further configured to generate a user interface. Via the user interface, a first task that requires navigation of a specified route through an environment may be presented. Via the user interface, a first indicator configured to navigate the specified route from an initial point in the environment to a target end-point with or without input from the individual may be presented. The user interface may be configured to display instructions to the individual to perform a second task, the second task requiring the individual either: (i) to navigate a reverse of at least a portion of the specified route, or (ii) to navigate at least a portion of the specified route at least one additional time. Via the user interface a second indicator configured to navigate in the environment in response to physical actions of the individual to control one of (i) a relative direction of the second indicator, or (ii) a speed of movement of the second indicator, or (iii) both (i) and (ii), to perform the second task. Measurement data may be obtained by measuring data indicative of the physical actions of the individual to control the second indicator in performing the second task. The measurement data may be analyzed to generate a performance metric for the performance of the second task, the performance metric providing an indication of the cognitive ability of the individual.

Generating the performance metric may include considering a total time taken to successfully complete the second task, a number of incorrect turns made by the second indicator, a number of incorrect directions of movement made by the second indicator, and/or a degree of deviation of the user-navigated route in the second task as compared to the specified route.

The recommendation may include an emotional processing tool, and the one or more processors may be further configured to generate a user interface. Via the user interface, a first instance of a task with an interference at the user interface is presented, requiring a first response from the individual to the first instance of the task in the presence of the interference and a response from the individual to at least one evocative element. At least one of the first instance of the task and the interference may include the at least one evocative element. The first response from the individual to the first instance of the task and the response from the individual to the at least one evocative element may be measured substantially simultaneously, providing a measure of emotional processing capabilities of the individual under emotional load. Data indicative of the first response and the response of the individual to the at least one evocative element is received. The data indicative of the first response and the response of the individual to the at least one evocative element is analyzed to compute at least one performance metric including at least one quantified indicator of cognitive abilities of the individual under emotional load.

The operations may further include controlling an actuating component to effect an auditory stimulus, a tactile stimulus, or a vibrational stimulus, and herein the evocative element comprises at least one of the auditory stimulus, the tactile stimulus, or the vibrational stimulus.

The operations may further include controlling one or more sensor components to measure the data indicative of the individual's performance of the task.

The one or more sensor components may include a gyroscope, an accelerometer, a motion sensor, a position sensor, a pressure sensor, an optical sensor, a video camera, an auditory sensor, and/or a vibrational sensor.

BRIEF DESCRIPTION OF DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

Figure 1:
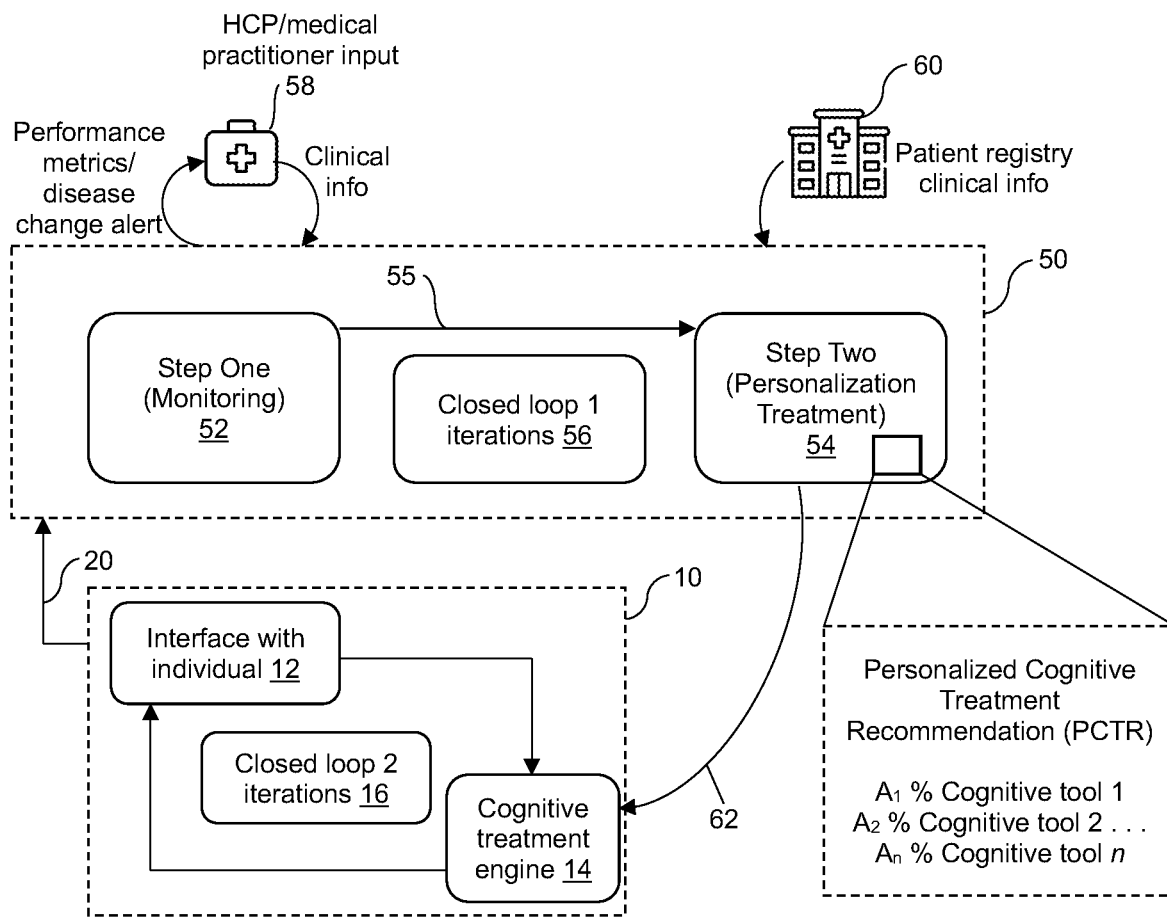
FIG. 1 is a schematic diagram illustrating the generation of a personalized cognitive treatment recommendation, according to the principles herein.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, apparatus and systems comprising a cognitive platform and/or platform product configured for coupling with one or more other types of measurement components, and for analyzing data collected from user interaction with the cognitive platform and/or from at least one measurement of the one or more other types of components. As non-limiting examples, the cognitive platform and/or platform product can be configured for cognitive training and/or for clinical purposes. The example systems, methods, and apparatus are applicable to the monitoring and/or treatment of cognition in individuals having an immune-mediated or neuro-degenerative disorder.

In an example implementation, the cognitive platform may be integrated with one or more physiological or monitoring components and/or cognitive testing components.

In another example implementation, the cognitive platform may be separate from, and configured for coupling with, the one or more physiological or monitoring components and/or cognitive testing components.

In any example herein, the cognitive platform and systems including the cognitive platform can be configured to present computerized tasks and platform interactions that inform cognitive assessment (including screening and/or monitoring) and/or to deliver cognitive treatment.

In any example herein, the platform product herein may be formed as, be based on, or be integrated with, an AKILI® platform product by Akili Interactive Labs, Inc. (Boston, MA), which is configured for presenting computerized tasks and platform interactions that inform cognitive assessment (including screening and/or monitoring) or to deliver cognitive treatment.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The example methods, apparatus and systems comprising the cognitive platform or platform product can be used by an individual, a clinician, a physician, and/or other medical or healthcare practitioner to provide data that can be used for an assessment and/or screening, monitoring, and treatment of the individual.

The disclosure relates to the growing concern and unmet needs related to the baseline evaluation of, the short-term and long-term monitoring of, and the treatment of cognition in individuals having immune-mediated or neuro-degenerative disorders. Technology for relatively specific diagnostics and sub-classifications of population exists for categories of disorders (such as but not limited to a diagnosis of Progressive Multiple Sclerosis—primary or secondary—versus Relapse Remitting Multiple Sclerosis). Cognitive dysfunctions are perceived as co-morbidities of immune-mediated or neuro-degenerative disorders and there is no sub-classification based on the cognitive profile of patients suffering from the same immune-mediated or neurodegenerative disorders, creating the risk of prescribing inadequate remediation therapies to certain patients cognitively impaired for different reasons. As an example, two patients with Multiple Sclerosis diagnosed with the same form of the disease, Relapsing-Remitting Multiple Sclerosis and receiving similar or comparable anti-inflammatory treatments, may yet suffer from completely different forms of cognitive impairments as the underlying brain disturbances (e.g. lesions, microlesions, and other microstructural or functional alterations) may be of different nature and could be impacting different locations or networks across the central nervous system (grey or white matter).

For example, individuals diagnosed as having Multiple Sclerosis may have differing types cognitive profiles depending on the positions, nature, and size of the lesions in the central nervous system. As a result of such heterogeneous lesion patterns, the same type and/or sequence of cognitive treatments that is effective in treating cognitive dysfunction identified in the cognitive profile of a first individual having an immune-mediated or neuro-degenerative disorder may be ineffective for a second individual diagnosed as having the same disorder.

In non-limiting examples, the methods, apparatus and systems comprising the cognitive platform or platform product can be used to determine a personalized cognitive treatment regimen for an individual having a condition, such as but not limited to an immune-mediated or neuro-degenerative disorder, and/or as a tool to aid in the monitoring of the progress of the individual as the individual interacts with the cognitive platform according to the personalized cognitive treatment regimen. The example tools can be built and trained using one or more training datasets obtained from individuals having a known condition, such as but not limited to an immune-mediated or neuro-degenerative disorder, including but not exclusively with classifier tools associated with deep learning based on support vector machines to find patterns in association with clinician-provided data via a patient registry, such as magnetic resonance imaging written or verbal reports integrated using natural language processing.

As used herein, the term "includes" means includes but is not limited to, the term "including" means including but not limited to. The term "based on" means based at least in part on.

The example platform products and cognitive platforms according to the principles described herein can be applicable to many different types of conditions, including immune-mediated and neuro-degenerative disorders, such as but not limited to multiple sclerosis and lupus.

The example systems according to the principles described herein can be applicable to many other types of conditions, including neuropsychological conditions, such as but not limited to dementia, Parkinson's disease, cerebral amyloid angiopathy, familial amyloid neuropathy, Huntington's disease, or other neurodegenerative condition, autism spectrum disorder (ASD), presence of the 16p11.2 duplication, and/or an executive function disorder (such as but not limited to attention deficit hyperactivity disorder (ADHD), sensory-processing disorder (SPD), mild cognitive impairment (MCI), Alzheimer's disease, multiple-sclerosis, schizophrenia, depression, or anxiety).

The instant disclosure is directed to computer-implemented devices formed as example cognitive platforms or platform products configured to implement software and/or other processor-executable instructions for the purpose of implementing example closed loop systems. In an example, the closed-loop system can be configured to adapt the digital cognitive treatment recommendation of each individual patient to personalize the cognitive treatment regimen according to the actual nature of the cognitive impairments associated with each individual patient. The cognitive treatment regimen can also be adjusted according to data provided by the individual, a clinician, a physician, and/or other medical or healthcare practitioner, as well as according to individual perceptual and/or sensori-motor deficits due to the disease process itself or resulting from present physiological state during treatment delivery. Such physiological states may comprise fatigue/drowsiness/alertness, or other data obtained via assessment by the device or as self-reported by the patient. Adjustments can also be made accordingly to means of device control/interaction, with non-limiting examples of such inputs including touch, swipe or other gesture relative to a user interface or image capture device (such as but not limited to a touch-screen or other pressure sensitive screen, or a camera), including any form of graphical user interface configured for recording a user interaction, a pointing device 320 (e.g., a mouse), a camera or other image recording device, a microphone or other sound recording device, an accelerometer, a gyroscope, or a sensor for tactile, vibrational, or auditory signal.

In an example, the system is configured to implement a set of algorithms and associated methods according to a first set of mathematical algorithms (the trained monitoring component 52) and is implemented on a computing device (such as but not limited to a digital smart device) producing multiple measures related to cognitive and physiological performance (such as but not limited to reaction time or targeting abilities). This monitoring phase differentiates the specific needs of one individual patient according to its distinct physio-pathological context associated with its cognitive impairments.

FIG. 1 shows a non-limiting example of the closed loop systems. The non-limiting example system of FIG. 1 includes closed loop system 10 and closed loop system 50. Closed loop system 10 is implemented via an interface 12 used by the individual to interact with a cognitive treatment engine 14 for a number of closed loop iterations 16. Closed loop system 50 is implemented via a monitoring component 52 for assessing and/or monitoring a status of the individual and a treatment generation component 54 for generating a personalized cognitive treatment recommendation for the individual, based on at least one closed loop iteration 56 of data between monitoring component 52 and treatment generation component 54. In an example, there are a plurality of iterations between the interface 12 and the cognitive treatment engine 14, to implement a continual adapting of the difficulty level of the tasks presented at the interface 12.

Closed loop system 10 can be any one or more of the cognitive tools described herein. Closed loop system 10 is configured such that the interface 12 presents to the individual one or more tasks generated by the cognitive treatment engine 14 and/or presents one or more questions or informational materials to the individual. In non-limiting examples, the cognitive treatment engine 14 can be configured to present task(s) to the individual at interface 12 to implement one or more task(s) associated with the interference processing, and/or the spatial navigation, and/or the emotional processing, and/or any other type of applicable cognitive tools, including cognitive tools described herein. The interface is also configured to measure data indicative of one or more physical interactions of the individual in performing the one or more tasks, and/or collect other data indicative of the performance and/or status of the individual. The cognitive treatment engine 14 is also configured to analyze the data measured and/or collected at interface 12, to generate an indication of cognitive abilities of the individual. In an example, the data is collected and analyzed to assess a status of the individual. In another example, the cognitive treatment engine 14 is also configured to adapt a difficulty level of at least one of the task(s) presented at interface 12, and analysis of the data measured and/or collected at interface 12 can be used to provide an indication of a change in cognitive abilities of the individual. In any example implementation of closed loop system 10, the cognitive treatment engine 14 also can be configured to analyze the responses to the one or more questions presented to the individual at interface 12 along with the data measured and/or collected to generate the indicator of cognitive abilities of the individual.

As shown in FIG. 1, the closed loop system 10 is configured to implement a number of closed loop iterations 16 to adapt a difficulty level of the one or more tasks presented at interface 12 based on the analysis using the cognitive treatment engine 14 of the data measured and/or collected at interface 12. In any example, the adapting can be effected using a staircasing method.

In an example, interface 12 can be configured as a graphical user interface presented at a display to present the one or more tasks. In another example, interface 12 can be configured to present the one or more tasks based on auditory, vibrational, and/or haptic signals. For example, interface 12 could include at least one actuator, haptic unit, or vibration unit, or other similar component for presenting the one or more tasks of the cognitive tool and to measure and/or otherwise collect data indicative of the individual's physical or other actions in interacting with the one or more tasks. In another example, the interface 12 can be configured to measure the measure and/or otherwise collect data indicative of the individual's physical or other actions in interacting with the one or more tasks using at least one camera or other image capture device.

Closed loop system 50 is configured to receive data 20 output from the closed loop system 10. In the non-limiting example of FIG. 1, the monitoring component 52 is configured to receive data 20 output from closed loop system 10. Monitoring component 52 is configured for assessing and/or monitoring a status of the individual based at least in part on an analysis of the data 20. The closed loop system 50 can also take as input data collected from questions presented to the individual as to symptoms of the individual's conditions, the individual's mood and emotional state, mobility, clinical info (which may include associated nData) about the individual obtained from a healthcare provider (HCP) or other medical practitioner 58, nData from one or more physiological measurement equipment and laboratories (such as but not limited to magnetic resonance imaging (MRI), heart-rate monitor, thermometer, etc). As a non-limiting example of nData from a physiological measurement using a MRI is a type, location and distribution of lesions in areas of the brain of an individual with multiple-sclerosis. For example, the nData can include data indicative of a region of the brain of the individual where lesions have formed, such as but not limited to the prefrontal cortex, hippocampal network, amygdala, caudate nucleus region of the brain, or the entorhinal cortex region of the brain. In an example, the monitoring component 52 is configured to receive that input data and analyze the input data to build a profile of the individual based on the indication of cognitive abilities received from the closed loop system 10 and other nData received for the individual. The clinical information may include clinical measures of the individual's symptoms and nData indicative of the individual's physiological condition, clinician diagnoses based on the clinical measures and nData, and other data.

In an example, the monitoring component 52 may also receive clinical data from one or more patient registries 60. A patient registry 60 could receive de-identified data from hospital or other health networks. The patient registry can be used to provide data which indicates the physiological measurements of a plurality of individuals and their disease condition, including trend data showing level of biomarkers for individuals and their disease condition (such as but not limited to levels of deficit, disease progression data, and MRI scans, measures of patient mobility, visual acumen, measures of cognitive abilities, etc. The patient registry 60 includes data from multiple patient with markers and progression that could be related to some of the data input to the monitoring component 52.

The monitoring component 52 can be configured as a predictive model based on training computational techniques and machine learning tools using training input dataset collected from individuals previously classified as to stage or degree of progression of the known conditions of interest. As used herein, the term "predictive model" encompasses models trained and developed based on models providing continuous output values and/or models based on discrete labels. In any example herein, the predictive model encompasses a classifier model. Non-limiting examples of the computational techniques and machine learning tools can include but are not limited to linear/logistic regression, principal component analysis, generalized linear mixed models, random decision forests, support vector machines, or artificial neural networks.

The example closed loop system 50 can be configured to apply the predictive model of the monitoring component 52, using the trained computational techniques and machine learning tools, to the output 20 from closed loop system 10, and/or received data indicative of the individual's response to one or more other tasks of a cognitive monitoring tool, and/or data from one or more physiological measures, and/or the clinical data, to generate the output 55. In an example, the predictive model can be configured for generating output 55 such as but not limited to a profile of the individual including indications of a degree of onset of the condition, a stage of progression of the condition, an assessment of cognitive health of the individual, performance measure of the individual in performing at least one task of a cognitive tool, a status of or a change in a motor function or cognitive condition of the individual, data indicative of a type and/or dose of a drug, biologic, pharmaceutical agent, or other treatment regimen being followed by the individual. A cognitive monitoring tool can be any cognitive tool that provides data indicative of a status of the cognitive abilities of the individual at a given point in time, without applying a treatment to the individual or enhancing cognition in the individual. As a non-limiting example, a cognitive monitoring tool can be a cognitive tool that is configured to presents one or more tasks to be performed by the individual but little or no adapting of the difficult levels of the tasks. In an example, the cognitive monitoring tool can be configured to present one or more tasks involving interference processing to the individual, without little or no adapting of the difficult levels. In any example herein, a cognitive treatment tool may be configured to function as a cognitive monitoring tool, to assess cognitive abilities of an individual without applying treatment.

An example system, method, and apparatus according to the principles herein can be configured to train monitoring component 52 based on the data 20 measured from a plurality of individuals from their interactions with the one or more tasks presented using the cognitive treatment engine of the closed loop system 10. In this example, the training dataset includes data measured from individuals that are previously classified as to an indication of cognitive abilities, and physiological condition. For example, the monitoring component 52 can be trained using a plurality of training datasets, where each training dataset is associated with a previously classified individual from a group of individuals. Each of the training dataset includes data indicative of one or more parameters indicative of the performance of the classified individual at the task(s) presented using the one or more cognitive tool(s), based on the classified individual's interaction with an example apparatus, system, or computing device described herein. The example monitoring component 52 also can take as input data indicative of the performance of the classified individual at a cognitive test, and/or a behavioral test, and/or data indicative of a diagnosis of a likelihood of onset of, or stage of progression of, a cognitive condition, a disease, or a disorder (including an executive function disorder) of the classified individual.

In an example, the monitoring component 52 can include a cognitive monitoring tool that monitors a cognitive condition of the individual. As a non-limiting example, the cognitive tool can be configured to present an interference processing tasks to the individual, with little or no adapting of the difficulty level of the tasks, such that the cognitive tool provides an assessment of the cognitive abilities of the individual without providing treatment.

In any example herein, the example trained monitoring component 52 can be used as an intelligent proxy for quantifiable assessments of an individual's cognitive abilities and/or the individuals disease or condition status (e.g., extent and location of lesions in brain). That is, once a monitoring component 52 is trained, the monitoring component 52 output can be used to provide the indication of the cognitive abilities of multiple individuals without use of a physiological measure, or another cognitive or behavioral assessment test. In an example, the trained monitoring component 52 can be used as an intelligent proxy to provide an indication of a likelihood of onset of a condition of the individual, or the stage of progression of the condition. In an example, the trained monitoring component 52 can be used as an intelligent proxy for subsequent measures of the condition of the individual. For example, as shown in FIG. 1, performance metrics and/or disease or condition change can be communicated to a HCP or other medical practitioner concerning the individual (with consent of the individual).

In an example, the trained monitoring component 52 can be used as a biomarker of certain clinical conditions of the individual based on a measure of data from one or more interactions of the individual with a cognitive tool.

Closed loop system 50 also includes a personalized treatment component 54 to receive output 55 from the monitoring component 52 and clinical data from one or more patient registries 60 to generate a personalized cognitive treatment recommendation (PCTR) for the individual, and to transmit the PCTR (shown at element 62 in FIG. 1) to the closed loop system 10. The patient registries includes images from patients that have previously had scans performed to measure their nData (including scans of lesions in the brain) and other measures of the clinical and physical condition of the individual. Using the data received from the monitoring component 52 and other data, such as but not limited to data from the one or more patient registries 60, the personalized treatment component 54 generates the PCTR. In a non-limiting example, the PCTR is an output that specifies a treatment regimen for the individual's which includes a recommendation of the percentage of time and treatment level ($A_i$) the individual should perform of one or more cognitive tools or other engine. The PCTR may provide a recommendation that uses only a single cognitive tool ($A_i=A_1$), two types of cognitive tools ($A_i=A_1, A_2$), three types of cognitive tools ($A_i=A_1, A_2, A_3$), or more. For example, the PCTR can specify $A_1$% a first cognitive tool, $A_2$% a second cognitive tool, $A_3$% a third cognitive tool, etc. Where a value $A_i=0$, the PCTR would indicate that the cognitive tool is not being used as a part of the treatment regimen of cognitive tools to the individual. As shown in FIG. 1, the closed loop system 50 can be configured to effect an iterative process (closed loop iterations 56) between the monitoring component 52 and the personalized treatment component 54, such that PCTR output generated by the personalized treatment component 54 for an individual is also transmitted to the monitoring component 52 to further train and refine the monitoring component 52 for refining the monitoring of the condition status and progression of the individual of interest and other individuals.

Based on the PCTR transmitted (as shown at element 62 in FIG. 1), the closed loop system 10 can be configured to effect the PCTR. For example, based on specification in the PCTR as to the $A_i$ for each different type of cognitive tool, the cognitive treatment engine 14 can cause the closed loop system 10 to present one or more tasks associated with a particular cognitive tool at the interface 12, for a certain duration of time, and at a specified level of intensity or amount of adapting of difficulty levels of the one or more task(s) presented.

As non-limiting examples, the PCTR can include specifications as to the duration of a regimen using a cognitive tool, an intensity of a treatment session (including adapting of the difficulty level), the types of cognitive tools to be used in the treatment.

The personalized treatment component 54 can be configured as a predictive model based on training computational techniques and machine learning tools using training input dataset collected from individuals previously classified as to stage or degree of progression of the known conditions of interest and known measurements and scores from one or more cognitive tools. Non-limiting examples of the computational techniques and machine learning tools can include but are not limited to linear/logistic regression, principal component analysis, generalized linear mixed models, random decision forests, support vector machines, or artificial neural networks.

The example closed loop system 50 can be configured to apply the predictive model of the personalization treatment component 54, using the trained computational techniques and machine learning tools, to the output data 55, and/or data from one or more physiological measures, and/or the clinical data, to generate the output data 62. In an example, the predictive model can be configured for generating output data 62 such as but not limited to the PCTR, data indicative of a degree of onset of the condition, a stage of progression of the condition, an assessment of cognitive health of the individual, a status of or a change in a motor function or cognitive condition of the individual, data indicative of a type and/or dose of a drug, biologic, pharmaceutical agent, or other treatment regimen being followed by the individual.

An example system, method, and apparatus according to the principles herein can be configured to train personalized treatment component 54 based on the output 55 from de-identified data from the output of the monitoring of a plurality of individuals. In this example, the training dataset includes monitoring data output generated from individuals that are previously classified as to an indication of cognitive abilities, and physiological condition. For example, the personalized treatment component 54 can be trained using a plurality of training datasets, where each training dataset is associated with a previously classified individual from a group of individuals. Each of the training dataset includes data indicative of one or more parameters indicative of the monitored condition of the classified individual. The example personalized treatment component 54 also can take as input data indicative of the performance of the classified individual at a cognitive test, and/or a behavioral test, and/or data indicative of a diagnosis of a likelihood of onset of, or stage of progression of, a cognitive condition, a disease, or a disorder (including an executive function disorder) of the classified individual.

In any example herein, the example trained personalized treatment component 54 can be used as an intelligent proxy for quantifiable assessments of an individual's cognitive abilities and/or the individuals disease or condition status (e.g., extent and location of lesions in brain). That is, once a personalized treatment component 54 is trained, the personalized treatment component 54 output can be used to provide the indication of the type of treatment regimen that can provide treatment for a cognitive condition of an individual without use of a physiological measure, or another cognitive or behavioral assessment test. In an example, the trained personalized treatment component 54 can be used as an intelligent proxy to provide an indication of a likelihood of change of a stage of progression of the condition. In an example, a PCTR for an individual can be communicated to a HCP or other medical practitioner concerning the individual (with consent of the individual).

The training of the personalized treatment component 54 based on machine learning or other computational technique could use scores indicative of the cognitive abilities of individuals using a cognitive tools and other aspects (e.g., data from other patients or HCPs), could also use data from patients not interacting with the cognitive tools and their disease progression to help train the personalized treatment component 54 to generate the personalize treatment (PCTR). Based on data from a plurality of individual (e.g., from thousands of other patients), the monitoring component 52 and/or the personalized treatment component 54 can be trained as disease markers. For example, the monitoring component 52 and/or the personalized treatment component 54 can be trained to predict a disease level of an individual based on the individual's scores using a cognitive tool, to provide a prediction of their cognitive status and of the potential efficacy on basis of their profile, duration of regimen, intensity, potentially the type of areas of being affected by the disease condition (e.g., the multiple-sclerosis lesions.

In an example, the monitoring component 52 can be trained to analyze the sensor and motor abilities of an individual, and monitor how they are affected by the course of the disease condition of the individual. The output data 55 from the monitoring component 52 can include performance measures that are transmitted to a HCP or other medical practitioner as an alert of the condition of the individual. As an example, the output from the monitoring component 52 can be transmitted as an alert that the individual being monitored may not be having the benefit of a prescribed drug regimen and/or prescribed cognitive tools regimen, or may be improving satisfactorily or at rates faster than projected based on use of the prescribed drug regimen and/or prescribed cognitive tools regimen.

The performance measures from the monitoring component 52 can be used as a proxy markers and/or biomarkers for the individual's condition, to trigger scheduling of a visit to the HCP or medical practitioner, or to cause re-evaluation or change in a regimen of drugs prescribed to the patient. For example, if the monitoring component 52 provides output 55 indicating a change in a motor function or cognitive condition of the individual, the HCP or medical practitioner can determine whether to increase a dose of a medication to take care of a condition that is deteriorating or improving.

As non-limiting examples, the type of tool specified in the PCTR output from the personalized treatment component 54, and the proportion/percentage of interaction recommended for the particular cognitive tool, can be dependent on the regions of the brain of an individual determined to be affected by lesions and/or the type of cognitive abilities of the individual that are determined to be affected. For example, the PCTR may specify a percentage amount (including duration of interaction) of the individual with a cognitive tool implementing interference processing tasks where it is determined from the nData that the lesions may be affecting or located in or near the prefrontal cortex and/or if the cData or nData indicates that cognitive abilities such as but not limited to working memory, and/or executive functions are affected. As another example, the PCTR may specify a percentage amount (including duration of interaction) of the individual with a cognitive tool implementing tasks involving spatial navigation and/or episodic memory components where it is determined from the nData that the lesions may be affecting or located in or near the extended hippocampal network, the caudate nucleus, or the entorhinal cortex region of the brain, and/or if the cData or nData indicates that cognitive abilities such as but not limited to working memory, spatial memory, motor control, and/or executive function are affected. As another example, the PCTR may specify a percentage amount (including duration of interaction) of the individual with a cognitive tool implementing tasks involving emotional processing where it is determined from the nData that the lesions may be affecting or located in or near the amygdala-dependent network and/or if the cData or nData indicates that cognitive abilities such as but not limited to working memory, mood, depressive condition are affected.

In an example, the output data 62 from the treatment personalization component 54 can be transmitted to a HCP or other medical practitioner as an alert of the condition of the individual. As an example, the output data 62 from the treatment personalization component 54, including the PCTR, can be transmitted as an alert that the individual being monitored may not be having the benefit of a prescribed drug regimen and/or prescribed cognitive tools regimen, or may be improving satisfactorily or at rates faster than projected based on use of the prescribed drug regimen and/or prescribed cognitive tools regimen.

In another example, the PCTR can specify differing combinations of the types of cognitive tools in the treatment regimen based on emerging lesion in differing areas of the brain. The PCTR can be specified to target a desired level of cognitive abilities and treatment regimen for the individual, including desired adherence and compliance with using the cognitive tools. For example, an individual with major depressive disorder may be prescribed increased sessions with the cognitive tool implementing emotional processing tasks, to address the depression and potentially increase compliance with the treatment for cognitive tools that address other cognitive conditions.

In some examples, the PCTR may include specified amounts of exposure and duration to cognitive tools such as psychoeducation (educational materials about disease process and coping skills), mindfulness (including meditation, focus on breathing, relaxation, etc.), or cognitive behavioral therapies. As an example, the mindfulness portion of the treatment PCTR regimen can be used as part of a regimen to reduce anxiety or depression in order to help improve the adherence and compliance to the other cognitive tool(s). In addition, mindfulness practice may help to reduce fatigue, and thereby reduce the amount of time the individual needs to spend using other prescribed cognitive tools in the PCTR regimen.

Monitoring component 52 (monitoring) enables the assessment of cognition according to the prescribed tasks in a manner that is comparable across subjects, and the association of the evolution of personalized treatment protocols with certain clinical cognitive assessments and/or biomarkers related to cognitive impairments or disease activity (e.g., anticipation of an exacerbation event or progression of disease severity or possibly disease remediation). Here, a health care provider during a health care visit, may measure cognitive functions and pathophysiology. Inputs for the Monitoring component 52 may be performance metrics generated by a patient while performing a prescribed task, as described below. Another input for monitoring component 52 may include data obtained by the patient's clinician or other health care provider on mental health, such as cognition and depressive symptoms using performance-based instruments and clinical interviews and/or pathophysiology using gold standards where applicable such as brain lesion load based on magnetic resonance imaging or immune state based on tissue sampling techniques. In some examples, the performance-based instruments may be validated. A non-limiting example input from the clinician or other healthcare provider for systemic lupus erythematosus (SLE) may comprise SLE Disease Activity Index (SLEDAI) physiological markers and the SLE neuropsychiatric symptom (SLE-NP) checklist. Another input for Monitoring component 52 may be health care provider drug, biologic, or other treatment information (e.g. Disease-Modifying Therapy choice and regimen, glucocorticoids, etc.). One of the outputs of Monitoring component 52 may be the personalized cognitive profile based on performance on the personalized treatment protocols and/or health care provider assessments (validated performance-based instruments and clinical interviews). Another output of Monitoring component 52 may be the personalized sensori-motor profile including perceptuo-motor abilities (e.g., visual and auditory acuity/sensitivity, and dexterity). Another output of monitoring component 52 may be the evolution of the performance on the personalized task protocols in relation to profile of pathophysiological information (i.e., clinical data) from the health care provider, such as gold standards where applicable such as brain lesion load based on magnetic resonance imaging or immune state based on tissue sampling techniques, in addition to information pertaining to the drug, biologic, or any other treatment regimen being followed by the patient. A further output of monitoring component 52 may be to the health care provider, in the form of performance metrics and/or alerts if certain pre-established performance thresholds are attained and prompt a clinical reappraisal (for example in relation to imminent relapse or change in neurodegenerative disease stage).

The output of the monitoring component 52 may be used by another set of algorithms and associated methods according to a second set of mathematical algorithms (the trained treatment personalization component 54) to titrate and adapt the therapeutic intervention to provide a personalized recommendation, adjusting the nature of the cognitive intervention for the actual cognitive profile of each patient. This recommendation serves as a personalized cognitive treatment recommendation (PCTR).

In particular, treatment personalization component 54 (personalization of treatment) may include several inputs, including outputs of monitoring component 52, such as the clinical information from the health care provider, patient's self-reported outcomes, such as experience of fatigue, perceived cognitive deficit, emotional/affective status. Yet another input may be physiological measures (e.g., % eye openness, vocal, actigraphic markers, etc.), obtained by the computing device and the graphic user interface and/or other I/O devices for receiving input from a user, for example, a keyboard or any suitable multi-point touch interface 318, a pointing device 320 (e.g., a mouse), a camera or other image recording device, a microphone or other sound recording device, an accelerometer, a gyroscope, a sensor for tactile, vibrational, or auditory signal, and/or at least one actuator.

Still another input for treatment personalization component 54 may be a personalized cognitive profile associated with the patient's measured cognitive impairments (including but not limited to processing speed and attentional processes of alerting and orienting, as well as executive control.). Yet another input for the Treatment personalization component 54 may be a personalized sensori-motor profile including perceptuo-motor abilities (e.g., visual and auditory acuity/sensitivity, and dexterity). Finally, another input may be from patient registries, including neuropsychological, cognitive, pathophysiological information, treatment regimen, and disease progression information.

The PCTR generated by Treatment personalization component 54 may include one or more of the following:

$A_1$% Interference processing for cognitive control and attention, depending on a condition of the prefrontal cortex;

$A_2$% Spatial navigation and episodic memory components, depending on a condition of the extended hippocampal network;

$A_3$% Emotional appraisal and regulation, depending on a condition of the amygdala-dependent network);

$A_4$% other engine as appropriate, e.g., working memory and other executive functions such as cognitive flexiblity; and $A_5$% psychoeducation, mindfulness, cognitive-behavioral training, other For example, a patient with Relapsing-Remitting Multiple Sclerosis exhibiting a lesion load manifesting mostly in prefrontal cortex, yet accompanied by lower levels in the extended hippocampal network but nowhere else, may receive a PCTR including 60% of interference processing and 40% of spatial navigation and episodic memory components.

The personalized treatment algorithm, used in the training of the treatment personalization component 54, may be based on physiologic (MRI—brain lesion localization), cognitive performance profile, and complementary performance-based tests or questionnaires, for example respectively for perceptual or sensori-motor abilities and affective status. Treatment personalization component 54 may also utilize clinical symptoms including an allocation of core mechanics as well as an adaptation of treatment (including duration) based on each individual's engagement level with the digital treatment, i.e. their sustained effort, beyond mere time on task.

Closed loop 1 iterations 56 includes periodic iterations of providing outputs from monitoring component 52 and other factors described above as inputs to treatment personalization component 54. As used herein the "periodic iterations" can be repeated at regular time intervals or at irregular time intervals. For example, closed loop system 50 can be configured to execute iterations of exchange of input data from the monitoring component 52 to personalized treatment component 54, or output of PCTR from the personalized treatment component 54 to the monitoring component 52, at regular time intervals or irregularly (e.g., initiated based on input of clinical data from a HCP or medical practitioner, or based on monitoring component 52 indication of a threshold change in a monitored parameter for the individual's disease state or performance metric). A benefit of implementing this closed loop 1 is rapid adjustment of the Personalized Cognitive Treatment Recommendation on the basis of incoming updates on cognitive, pathophysiological, or other factors, which, based on clinic-only standard care, would otherwise only lead to a revised course of treatment every few months if not annually or at even longer even longer periods, if at all.

The PCTR is provided to a digital treatment engine to treat the patient. The PCTR is translated to a set of tasks and challenges targeting functions of interest, including cognitive, perceptual, and sensory-motor abilities, through interaction with the device and/or in combination with physical activities dictated by the program.

The PCTR may be manually dictated by a health care provider. Datasets, such as from patient registries 60 (e.g. magnetic resonance imaging written or verbal reports integrated using natural language processing, drug, biologic, or other treatment regimen; disease progression), obtained from individuals having a known condition, such as an immune-mediated or neuro-degenerative disorder, can be used to train Treatment personalization component 54 using as a non-limiting example machine learning tools associated with deep learning to find disease profiles and progression patterns that can be associated with neuropsychological performance, and used to optimize cognitive treatment efficacy. Through such dataset training, informed by feedback with patient performance and progression, along with other factors affecting cognition and/or cognitive treatment engagement and/or cognitive treatment efficacy, Treatment personalization component 54 can fully automatically provide a PCTR.

In an example, the PCTR may also include a recommendation for use of sensory stimulation in combination with one or more of the cognitive tools. Sensory stimulation according to specific frequency bands may boost cognitive treatment and/or help reduce inflammation, e.g., during active device use or otherwise, such as during sleep. As non-limiting examples, for suitable sensory stimulation using gamma frequency patterns, around 40 Hz, the computing device can be configured to present auditory stimulus or initiate other auditory-based interaction with the user, and/or to present vibrational stimuli or initiate other vibrational-based interaction with the user, and/or to present tactile stimuli or initiate other tactile-based interaction with the user, and/or to present visual stimuli or initiate other visual-based interaction with the user, using an actuating component. Such sensory stimulation may be implemented by graphic user interface and/or other I/O devices for delivering input to a user, for example, a sensor for tactile, vibrational, or auditory signal, and/or at least one actuating component.

Device control may be adapted according to a personalized sensori-motor profile, e.g., instead of tapping a target with a finger, a patient may use a head nod or a vocal command.

The PCTR can be transmitted (at transmission point 62 of FIG. 1) to be used by a digital treatment engine (such as cognitive treatment engine 14) to combine each distinct cognitive therapeutic algorithm (comprising interference processing, spatial navigation, emotional/affective, full-body motion integrating cognitive and physical training, complemented with sensory/motor discrimination (e.g. visual or auditory), fine motor control training, Cognitive-Behavioral Therapy, mindfulness, psychoeducation or other) and recommend an appropriate composition of algorithms and stimulus (type and duration) over the course of treatments (staircase profiles, percentage (%) of each cognitive treatment administered to the patient over the course of treatment) to compose the personalized cognitive treatment program for each patient.

Closed loop 2 iterations 16 provides a continuous or continual iterations of performance thresholds to achieve on any prescribed task based on real-time performance in order to constantly maintain the user at the desired degree of difficulty to reap maximal cognitive benefits. For example, closed loop system 10 can be configured to execute continuous or continual iterations of exchange of input data, measurement data, or output data between interface 12 and cognitive treatment engine 14, and/or the adapting of difficulty levels of one or more sessions or trials of at least one of the tasks presented at interface 12 based on the analysis performed at cognitive treatment engine 14 based on the data input or measured at interface 12.

A performance metric generated by the device based on the performance of recommended tasks by the patient may be provided as an input to Monitoring component 52. For example, an index of interference processing under neutral of under emotional load, of spatial navigation ability, or of memory.

The novel adaptive treatment closed loop allows for adjustment at periodic interval of the PCTR to personalize the treatment to the evolving cognitive profiles of patients receiving cognitive treatments.

In some embodiments, the health care provider collects the appropriate inputs for Treatment personalization component 54 and Treatment personalization component 54 calculates a PCTR based on data received from the HCP of his or her interpretation of the inputs and knowledge of various possible treatments. In other embodiments, machine learning techniques may be employed to use the data received from the HCP to train the treatment personalization component 54 to generate a PCTR.

The example methods, apparatus and systems are configured for measuring data indicative of a user's performance at one or more tasks, to provide a user performance metric, which may ultimately be used as a disease biomarker. The example tasks may include an interference processing task, and/or a spatial navigation and memory task, and/or an emotional/affective task. The example performance metric can be used to derive an assessment of a user's cognitive abilities and/or to measure a user's response to a cognitive treatment, and/or to provide data or other quantitative indicia of a user's condition (including physiological condition and/or cognitive condition). Non-limiting example cognitive platforms or platform products according to the principles herein can be configured to classify an individual with respect to a condition, such as but not limited to an immune-mediated or neurodegenerative disorder, the expression level of protein(s) that can be of clinical interest in the condition, and/or potential efficacy of use of the cognitive platform and/or platform product when the individual is administered a drug, biologic or other pharmaceutical agent, based on the data collected from the individual's interaction with the cognitive platform and/or platform product and/or metrics computed based on the analysis (and associated computations) of that data. Yet other non-limiting example cognitive platforms or platform products according to the principles herein can be configured to classify an individual with respect to likelihood of onset and/or stage of progression of an immune-mediated or neurodegenerative condition, based on the data collected from the individual's interaction with the cognitive platform and/or platform product and/or metrics computed based on the analysis (and associated computations) of that data. The immune-mediated condition can be, but is not limited to, multiple sclerosis or lupus.

Any performance indicator and/or classification of an individual as to likelihood of onset and/or stage of progression of a neurodegenerative condition according to the principles herein can be transmitted as a signal to a medical device, healthcare computing system, or other device, and/or to a medical practitioner, a health practitioner, a physical therapist, a behavioral therapist, a sports medicine practitioner, a pharmacist, or other practitioner, to allow formulation of a course of treatment for the individual or to modify an existing course of treatment, including to determine a change in dosage of a drug, biologic or other pharmaceutical agent to the individual or to determine an optimal type or combination of drug, biologic or other pharmaceutical agent to the individual.

In any example herein, the platform product or cognitive platform can be configured as any combination of a medical device platform, a monitoring device platform, a screening device platform, a treatment device platform, or other device platform.

The instant disclosure is also directed to example systems that include platform products and cognitive platforms that are configured for coupling with one or more physiological or monitoring component and/or cognitive testing component. In some examples, the systems include platform products and cognitive platforms that are integrated with the one or more other physiological or monitoring component and/or cognitive testing component. In other examples, the systems include platform products and cognitive platforms that are separately housed from and configured for communicating with the one or more physiological or monitoring component and/or cognitive testing component, to receive data indicative of measurements made using such one or more components.

As used herein, the term "cData" refers to data collected from measures of an interaction of a user with a computer-implemented device formed as a platform product or a cognitive platform.

As used herein, the term "nData" refers to other types of data that can be collected according to the principles herein. Any component used to provide nData is referred to herein as a nData component.

In any example herein, the cData and/or nData can be collected in real-time.

In non-limiting examples, the nData can be collected from measurements using one or more physiological or monitoring components and/or cognitive testing components. In any example herein, the one or more physiological components are configured for performing physiological measurements. The physiological measurements provide quantitative measurement data of physiological parameters and/or data that can be used for visualization of physiological structure and/or functions.

As a non-limiting example, nData can be collected from measurements of types of protein and/or conformation of proteins (can provide an indication of protein formation (e.g., whether the proteins are forming aggregates) in the tissue or fluid (including blood) of an individual and/or in tissue or fluid (including blood) collected from the individual. In some examples, the measurement can be of tissue and/or fluid in situ or extracted from the individual's brain. The expression group can be defined based on a threshold expression level of the protein of clinical interest in the neurodegenerative condition, where a measured value of expression level above a pre-specified threshold defines a first expression group and a measured value of expression level below the pre-specified threshold defines a second expression group. In other examples, the nData can be neuropsychological or other clinical instrument data.

It is understood that reference to "drug" herein encompasses a drug, a biologic and/or other pharmaceutical agent.

In a non-limiting example, the physiological instrument can be based on MRI, and the nData can be measurement data indicative of the cortical thickness, brain functional activity changes, or other measure.

In other non-limiting examples, nData can include any data that can be used to characterize an individual's status, such as but not limited to age, gender or other similar data.

In any example herein, the data (including cData and nData) is collected with the individual's consent.

In any example herein, the one or more physiological components can include any means of measuring physical characteristics of the body and nervous system, including electrical activity, heart rate, blood flow, and oxygenation levels, to provide the nData. This can include camera-based heart rate detection, measurement of galvanic skin response, blood pressure measurement, electroencephalogram, electrocardiogram, magnetic resonance imaging, near-infrared spectroscopy, vocal patterns, actigraphy, and/or pupil dilation measures, to provide the nData.

Other examples of physiological measurements to provide nData include, but are not limited to, the measurement of body temperature, heart or other cardiac-related functioning using an electrocardiograph (ECG), electrical activity using an electroencephalogram (EEG), event-related potentials (ERPs), magnetic resonance imaging (MRI), functional magnetic resonance imaging (fMRI), blood pressure, electrical potential at a portion of the skin, galvanic skin response (GSR), magneto-encephalogram (MEG), eye-tracking device or other optical detection device including processing units programmed to determine degree of pupillary dilation, functional near-infrared spectroscopy (fNIRS), and/or a positron emission tomography (PET) scanner. An EEG-fMRI or MEG-fMRI measurement allows for simultaneous acquisition of electrophysiology (EEG/MEG) nData and hemodynamic (fMRI) nData.

The fMRI also can be used to provide measurement data (nData) indicative of neuronal activation, based on the difference in magnetic properties of oxygenated versus de-oxygenated blood supply to the brain. The fMRI can provide an indirect measure of neuronal activity by measuring regional changes in blood supply, based on a positive correlation between neuronal activity and brain metabolism.

A PET scanner can be used to perform functional imaging to observe metabolic processes and other physiological measures of the body through detection of gamma rays emitted indirectly by a positron-emitting radionuclide (a tracer). The tracer can be introduced into the user's body using a biologically-active molecule. Indicators of the metabolic processes and other physiological measures of the body can be derived from the scans, including from computer reconstruction of two- and three-dimensional images of from nData of tracer concentration from the scans. The nData can include measures of the tracer concentration and/or the PET images (such as two- or three-dimensional images).

In any example herein, the task can be a spatial navigation task according to the principles herein. In this example, a computing device is configured to present an elevated, overhead view of a landscape that includes one or more internal course and obstacles. In this example, portions of the course are configured to include pathways and passageways that allow traversal of an avatar or other guidable element. The navigation task requires an individual to formulate a pathway about the strategically positioned obstacles from an initial point ("A") to at least one target location ("B"). The computing device can be configured to present instructions to the individual to navigate the course.

The computing device also can be configured to provide an individual with an input device or other type of control element that allows the individual to traverse the course, including specifying and/or controlling one or more of the speed of movement, orientation, velocity, choice of navigation strategy, the wait or delay period, or other period of inaction, prior to continuing in a given direction of a course or changing direction, time interval to complete a course, and/or frequency or number of times of referral to an aerial or elevated view of a landscape (including as a map), including values of any of these parameters as a function of time.

The computing device can be configured to collect data indicative of the performance metric that quantifies the navigation strategy employed by the individual from the initial point ("A") to reach one or more target points ("B"). For example, the computing device can be configured to collect data indicative of the individual's decision to proceed from the initial point ("A") along the dashed line or the dotted line, the speed of movement, the orientation of the avatar or other guidable element, among other measures. In the various examples, performance metrics that can be measured using the computing device can include data indicative of the speed of movement, orientation, velocity, choice of navigation strategy, wait or delay period, or other period of inaction, prior to continuing in a given direction of a course or changing direction, time interval to complete a course, and/or frequency or number of times of referral to an aerial or elevated view of a landscape (including as a map), including values of any of these parameters as a function of time. As another non-limiting example, the performance metrics can include a measure of the degree of optimization of the path navigated by the individual through the course, such as though determining the shortest path or near-shortest path through the course.

In another example herein, a task can involve one or more activities that a user is required to engage in. Any one or more of the tasks can be computer-implemented as computerized stimuli or interaction (described in greater detail below). For a targeting task, the cognitive platform may require temporally-specific and/or position-specific responses from a user. For a navigation task, the cognitive platform may require position-specific and/or motion-specific responses from the user. For a memory task, the cognitive platform may require stimulus-specific, position-specific, and/or temporally-specific responses from the user. For a facial expression recognition or object recognition task, the cognitive platform may require temporally-specific and/or position-specific responses from the user. For integrative cognitive and full-body motion tasks, the cognitive platform may require stimulus-specific, position-specific, and/or temporally-specific responses, in combination with specific physical movements/choreographies. The multi-tasking tasks can include any combination of two or more tasks. In non-limiting examples, the user response to tasks, such as but not limited to targeting and/or navigation and/or facial expression recognition or object recognition task(s), can be recorded using an input device of the cognitive platform. Non-limiting examples of such input devices can include a touch, swipe or other gesture relative to a user interface or image capture device (such as but not limited to a touch-screen or other pressure sensitive screen, or a camera), including any form of graphical user interface configured for recording a user interaction. In other non-limiting examples, the user response recorded using the cognitive platform for tasks, such as but not limited to targeting and/or navigation and/or facial expression recognition or object recognition task(s), can include user actions that cause changes in a position, orientation, or movement of a computing device including the cognitive platform. Such changes in a position, orientation, or movement of a computing device can be recorded using an input device disposed in or otherwise coupled to the computing device, such as but not limited to a sensor. Non-limiting examples of sensors include a motion sensor, position sensor, and/or an image capture device (such as but not limited to a camera).

In an example implementation involving multi-tasking tasks, the computer device is configured (such as using at least one specially-programmed processing unit) to cause the cognitive platform to present to a user two or more different type of tasks, such as but not limited to, targeting and/or navigation and/or facial expression recognition or object recognition tasks, during a short time frame (including in real-time and/or substantially simultaneously). The computer device is also configured (such as using at least one specially-programmed processing unit) to collect data indicative of the type of user response received to the multi-tasking tasks, within the short time frame (including in real-time and/or substantially simultaneously). In these examples, the two or more different types of tasks can be presented to the individual within the short time frame (including in real-time and/or substantially simultaneously), and the computing device can be configured to receive data indicative of the user response(s) relative to the two or more different types of tasks within the short time frame (including in real-time and/or substantially simultaneously).

In some examples, the short time frame can be of any time interval at a resolution of up to about 1.0 millisecond or greater. The time intervals can be, but are not limited to, durations of time of any division of a periodicity of about 2.0 milliseconds or greater, up to any reasonable end time. The time intervals can be, but are not limited to, about 3.0 millisecond, about 5.0 millisecond, about 10 milliseconds, about 25 milliseconds, about 40 milliseconds, about 50 milliseconds, about 60 milliseconds, about 70 milliseconds, about 100 milliseconds, or greater. In other examples, the short time frame can be, but is not limited to, fractions of a second, about a second, between about 1.0 and about 2.0 seconds, or up to about 2.0 seconds, or more.

In some examples, the platform product or cognitive platform can be configured to collect data indicative of a reaction time of a user's response relative to the time of presentation of the tasks. For example, the computing device can be configured to cause the platform product or cognitive platform to provide smaller or larger reaction time window for a user to provide a response to the tasks as a way of adjusting the difficulty level.

As used herein, the term "computerized stimuli or interaction" or "CSI" refers to a computerized element that is presented to a user to facilitate the user's interaction with a stimulus or other interaction, whether active or passive. As non-limiting examples, the computing device can be configured to present auditory stimulus or initiate other auditory-based interaction with the user, and/or to present vibrational stimuli or initiate other vibrational-based interaction with the user, and/or to present tactile stimuli or initiate other tactile-based interaction with the user, and/or to present visual stimuli or initiate other visual-based interaction with the user.

Any task according to the principles herein can be presented to a user via a computing device, actuating component, or other device that is used to implement one or more stimuli or other interactive element. For example, the task can be presented to a user by rendering a graphical user interface to present the computerized stimuli or interaction (CSI) or other interactive elements. In other examples, the task can be presented to a user as auditory, tactile, or vibrational computerized elements (including CSIs) using an actuating component. Description of use of (and analysis of data from) one or more CSIs in the various examples herein also encompasses use of (and analysis of data from) tasks comprising the one or more CSIs in those examples.

In an example where the computing device is configured to present visual CSI, the CSI can be rendered using at least one graphical user interface to be presented to a user. In some examples, at least one graphical user interface is configured for measuring responses as the user interacts with CSI computerized element rendered using the at least one graphical user interface. In a non-limiting example, the graphical user interface can be configured such that the CSI computerized element(s) are active, and may require at least one response from a user, such that the graphical user interface is configured to measure data indicative of the type or degree of interaction of the user with the platform product. In another example, the graphical user interface can be configured such that the CSI computerized element(s) are a passive and are presented to the user using the at least one graphical user interface but may not require a response from the user. In this example, the at least one graphical user interface can be configured to exclude the recorded response of an interaction of the user, to apply a weighting factor to the data indicative of the response (e.g., to weight the response to lower or higher values), or to measure data indicative of the response of the user with the platform product as a measure of a misdirected response of the user (e.g., to issue a notification or other feedback to the user of the misdirected response).

In an example, the cognitive platform and/or platform product can be configured as a processor-implemented system, method or apparatus that includes and at least one processing unit. In an example, the at least one processing unit can be programmed to render at least one graphical user interface to present the computerized stimuli or interaction (CSI) or other interactive elements to the user for interaction. In other examples, the at least one processing unit can be programmed to cause an actuating component of the platform product to effect auditory, tactile, or vibrational computerized elements (including CSIs) to effect the stimulus or other interaction with the user. The at least one processing unit can be programmed to cause a component of the program product to receive data indicative of at least one user response based on the user interaction with the CSI or other interactive element (such as but not limited to cData), including responses provided using the input device. In an example where at least one graphical user interface is rendered to present the computerized stimuli or interaction (CSI) or other interactive elements to the user, the at least one processing unit can be programmed to cause graphical user interface to receive the data indicative of at least one user response. The at least one processing unit also can be programmed to: analyze the cData to provide a measure of the individual's cognitive condition, and/or analyze the differences in the individual's performance based on determining the differences between the user's responses (including based on differences in the cData), and/or adjust the difficulty level of the auditory, tactile, or vibrational computerized elements (including CSIs), the CSIs or other interactive elements based on the analysis of the cData (including the measures of the individual's performance determined in the analysis), and/or provide an output or other feedback from the platform product that can be indicative of the individual's performance, and/or cognitive assessment, and/or response to cognitive treatment, and/or assessed measures of cognition. In non-limiting examples, the at least one processing unit also can be programmed to classify an individual with respect to an immune-mediated or neurodegenerative condition, the expression level of protein(s) that can be of clinical interest in the condition, and/or potential efficacy of use of the cognitive platform and/or platform product when the individual is administered a drug, biologic or other pharmaceutical agent, based on the cData collected from the individual's interaction with the cognitive platform and/or platform product and/or metrics computed based on the analysis (and associated computations) of that cData. In non-limiting examples, the at least one processing unit also can be programmed to classify an individual as to likelihood of onset and/or stage of progression of an immune-mediated or neurodegenerative condition, based on the cData collected from the individual's interaction with the cognitive platform and/or platform product and/or metrics computed based on the analysis (and associated computations) of that cData. The neurodegenerative condition can be, but is not limited to, lupus or multiple sclerosis.

In an example, the at least one processing unit can be programmed to render at least one graphical user interface to present the CSI or other interactive elements and/or to cause an actuating component of the platform product to effect auditory, tactile, or vibrational computerized elements (including CSIs) or connected devices (for example goggles, earphones, haptic device or otherwise) to effect the stimulus for passive consumption by the user, as presented in a pattern intended for frequency-band entrainment of the brain and/or for reduction of inflammation/modulation of immune responses during cognitive treatment via the graphic user interface and/or independently of graphic user interface interaction.

An example system, method, and apparatus according to the principles herein includes a platform product (including using an APP) that uses a cognitive platform configured to render at least one emotional/affective element (EAE), to add emotional processing as an overt component for tasks in multi-task gameplay (MTG) or single-task gameplay (STG). In one example, the EAE is used in the tasks configured to assess cognition or to improve cognition related to emotions, and the data (including cData) collected as a measure of user interaction with the rendered EAE in the platform product is used to determine the measures of the assessment of cognition or the improvement to measures of cognition after a treatment configured for interaction using the graphical user interface, or as auditory, tactile, or vibrational elements, of the platform product. The EAE can be configured to collect data to measure the impact of emotions on non-emotional cognition, such as by causing the graphical user interface to render spatial tasks for the user to perform under emotional load, and/or to collect data to measure the impact of non-emotional cognition on emotions, such as by causing the graphical user interface to render features that employ measures of executive function to regulate emotions. In one example implementation, the graphical user interface can be configured to render tasks for identifying the emotion indicated by the CSI (based on measurement data), maintaining that identification in working memory, and comparing it with the measures of emotion indicated by subsequent CSI, while under cognitive load due to MTG.

In other examples, the platform product can be configured as a processor-implemented system, method or apparatus that includes a display component, an input device, and the at least one processing unit. The at least one processing unit can be programmed to render at least one graphical user interface, for display at the display component, to present the computerized stimuli or interaction (CSI) or other interactive elements to the user for interaction. In other examples, the at least one processing unit can be programmed to cause an actuating component of the platform product to effect auditory, tactile, or vibrational computerized elements (including CSIs) to effect the stimulus or other interaction with the user.

Non-limiting examples of an input device include a touch-screen, or other pressure-sensitive or touch-sensitive surface, a motion sensor, a position sensor, a pressure sensor, joystick, exercise equipment, and/or an image capture device (such as but not limited to a camera).

In any example, the input device is configured to include at least one component configured to receive input data indicative of a physical action of the individual(s), where the data provides a measure of the physical action of the individual(s) in interacting with the cognitive platform and/or platform product, e.g., to perform the one or more tasks and/or tasks with interference.

The analysis of the individual's performance may include using the computing device to compute percent accuracy, number of hits and/or misses during a session or from a previously completed session. Other indicia that can be used to compute performance measures are the amount time the individual takes to respond after the presentation of a task (e.g., as a targeting stimulus). Other indicia can include, but are not limited to, reaction time, response variance, number of correct hits, omission errors, false alarms, learning rate, spatial deviance, subjective ratings, and/or performance threshold, etc.

In a non-limiting example, the user's performance can be further analyzed to compare the effects of two different types of tasks on the user's performances, where these tasks present different types of interferences (e.g., a distraction or an interruptor). The computing device is configured to present the different types of interference as CSIs or other interactive elements that divert the user's attention from a primary task. For a distraction, the computing device is configured to instruct the individual to provide a primary response to the primary task and not to provide a response (i.e., to ignore the distraction). For an interruptor, the computing device is configured to instruct the individual to provide a response as a secondary task, and the computing device is configured to obtain data indicative of the user's secondary response to the interruptor within a short time frame (including at substantially the same time) as the user's response to the primary task (where the response is collected using at least one input device). The computing device is configured to compute measures of one or more of a user's performance at the primary task without an interference, performance with the interference being a distraction, and performance with the interference being an interruption. The user's performance metrics can be computed based on these measures. For example, the user's performance can be computed as a cost (performance change) for each type of interference (e.g., distraction cost and interruptor/multi-tasking cost). The user's performance level on the tasks can be analyzed and reported as feedback, including either as feedback to the cognitive platform for use to adjust the difficulty level of the tasks, and/or as feedback to the individual concerning the user's status or progression.

In a non-limiting example, the computing device can also be configured to analyze, store, and/or output the reaction time for the user's response and/or any statistical measures for the individual's performance (e.g., percentage of correct or incorrect response in the last number of sessions, over a specified duration of time, or specific for a type of tasks (including non-target and/or target stimuli, a specific type of task, etc.).

In a non-limiting example, the computerized element includes at least one task rendered at a graphical user interface as a visual task or presented as an auditory, tactile, or vibrational task. Each task can be rendered as interactive mechanics that are designed to elicit a response from a user after the user is exposed to stimuli for the purpose of cData and/or nData collection.

In a non-limiting example, the computerized element includes at least one platform interaction (gameplay) element of the platform rendered at a graphical user interface, or as auditory, tactile, or vibrational element of a program product. Each platform interaction (gameplay) element of the platform product can include interactive mechanics (including in the form of videogame-like mechanics) or visual (or cosmetic) features that may or may not be targets for cData and/or nData collection.

As used herein, the term "gameplay" encompasses a user interaction (including other user experience) with aspects of the platform product.

In a non-limiting example, the computerized element includes at least one element to indicate positive feedback to a user. Each element can include an auditory signal and/or a visual signal emitted to the user that indicates success at a task or other platform interaction element, i.e., that the user responses at the platform product has exceeded a threshold success measure on a task or platform interaction (gameplay) element.

In a non-limiting example, the computerized element includes at least one element to indicate negative feedback to a user. Each element can include an auditory signal and/or a visual signal emitted to the user that indicates failure at a task or platform interaction (gameplay) element, i.e., that the user responses at the platform product has not met a threshold success measure on a task or platform interaction element.

In a non-limiting example, the computerized element includes at least one element for messaging, i.e., a communication to the user that is different from positive feedback or negative feedback.

In a non-limiting example, the computerized element includes at least one element for indicating a reward. A reward computer element can be a computer-generated feature that is delivered to a user to promote user satisfaction with the CSIs and as a result, increase positive user interaction (and hence enjoyment of the user experience).

In a non-limiting example, the cognitive platform can be configured to render multi-task interactive elements. In some examples, the multi-task interactive elements are referred to as multi-task gameplay (MTG). The multi-task interactive elements include interactive mechanics configured to engage the user in multiple temporally-overlapping tasks, i.e., tasks that may require multiple, substantially simultaneous responses from a user.

In a non-limiting example, the cognitive platform can be configured to render single-task interactive elements. In some examples, the single-task interactive elements are referred to as single-task gameplay (STG). The single-task interactive elements include interactive mechanics configured to engage the user in a single task in a given time interval.

According to the principles herein, the term "cognition" or "cognitive" refers to the mental action or process of acquiring knowledge and understanding through thought, experience, and the senses. This includes, but is not limited to, psychological concepts/domains such as, executive function, memory, perception, attention, emotion/affect, motor control, and interference processing. An example computer-implemented device according to the principles herein can be configured to collect data indicative of user interaction with a platform product, and to compute metrics that quantify user performance. The quantifiers of user performance can be used to provide measures of cognition (for cognitive assessment) or to provide measures of status or progress of a cognitive treatment.

According to the principles herein, the term "treatment" or "treat" refers to any manipulation of CSI in a platform product (including in the form of an APP) that results in a measurable improvement of the abilities of a user, such as but not limited to improvements related to cognition, a user's mood, emotional state, and/or level of engagement or attention to the cognitive platform. The degree or level of improvement can be quantified based on user performance measures as describe herein. In an example, the term "treatment" may also refer to a therapy.

According to the principles herein, the term "session" refers to a discrete time period, with a clear start and finish, during which a user interacts with a platform product to receive assessment or treatment from the platform product (including in the form of an APP).

According to the principles herein, the term "assessment" refers to at least one session of user interaction with CSIs or other feature or element of a platform product. The data collected from one or more assessments performed by a user using a platform product (including in the form of an APP) can be used as to derive measures or other quantifiers of cognition, or other aspects of a user's abilities.

According to the principles herein, the term "emotional load" refers to cognitive load that is specifically associated with processing emotional information or regulating emotions.

According to the principles herein, the term "cognitive load" refers to the amount of mental resources that a user may need to expend to complete a task. This term also can be used to refer to the challenge or difficulty level of a task or gameplay.

In an example, the platform product comprises a computing device that is configured to present to a user a cognitive platform based on interference processing. In an example system, method and apparatus that implements interference processing, at least one processing unit is programmed to render at least one first graphical user interface or cause an actuating component to generate an auditory, tactile, or vibrational signal, to present first CSIs as a first task that requires a first type of response from a user. The example system, method and apparatus is also configured to cause the at least one processing unit to render at least one second graphical user interface or cause the actuating component to generate an auditory, tactile, or vibrational signal, to present second CSIs as a first interference with the first task, requiring a second type of response from the user to the first task in the presence of the first interference. In a non-limiting example, the second type of response can include the first type of response to the first task and a secondary response to the first interference. In another non-limiting example, the second type of response may not include, and be quite different from, the first type of response. The at least one processing unit is also programmed to receive data indicative of the first type of response and the second type of response based on the user interaction with the platform product (such as but not limited to cData), such as but not limited to by rendering the at least one graphical user interface to receive the data. The platform product also can be configured to receive nData indicative of measurements made before, during, and/or after the user interacts with the cognitive platform (including nData from measurements of physiological or monitoring components and/or cognitive testing components). The at least one processing unit also can be programmed to: analyze the cData and/or nData to provide a measure of the individual's condition (including physiological and/or cognitive condition), and/or analyze the differences in the individual's performance based on determining the differences between the measures of the user's first type and second type of responses (including based on differences in the cData) and differences in the associated nData. The at least one processing unit also can be programmed to: adjust the difficulty level of the first task and/or the first interference based on the analysis of the cData and/or nData (including the measures of the individual's performance and/or condition (including physiological and/or cognitive condition) determined in the analysis), and/or provide an output or other feedback from the platform product that can be indicative of the individual's performance, and/or cognitive assessment, and/or response to cognitive treatment, and/or assessed measures of cognition. In non-limiting examples, the at least one processing unit also can be programmed to classify an individual as to an immune-mediated or neurodegenerative condition, the expression level of protein(s) that can be of clinical interest in the condition, and/or potential efficacy of use of the cognitive platform and/or platform product when the individual is administered a drug, biologic or other pharmaceutical agent, based on nData and the cData collected from the individual's interaction with the cognitive platform and/or platform product and/or metrics computed based on the analysis (and associated computations) of that cData and the nData. In non-limiting examples, the at least one processing unit also can be programmed to classify an individual as to likelihood of onset and/or stage of progression of an immune-mediated or neurodegenerative condition, based on nData and the cData collected from the individual's interaction with the cognitive platform and/or platform product and/or metrics computed based on the analysis (and associated computations) of that cData and the nData. The immune-mediated or neurodegenerative condition can be, but is not limited to, lupus and multiple sclerosis.

In an example, the feedback from the differences in the individual's performance based on determining the differences between the measures of the user's first type and second type of responses and the nData can be used as an input in the cognitive platform that indicates real-time performance of the individual during one or more session(s). The data of the feedback can be used to as an input to a computation component of the computing device to determine a degree of adjustment that the cognitive platform makes to a difficulty level of the first task and/or the first interference that the user interacts within the same ongoing session and/or within a subsequently-performed session.

As a non-limiting example, the cognitive platform based on interference processing can be a cognitive platform based on the Project: EVO™ platform by Akili Interactive Labs, Inc. (Boston, MA).

In an example system, method and apparatus according to the principles herein that is based on interference processing, the graphical user interface is configured such that, as a component of the interference processing, one of the discriminating features of the targeting task that the user responds to is a feature in the platform that displays an emotion, a shape, a color, and/or a position that serves as an interference element in interference processing.

An example system, method, and apparatus according to the principles herein includes a cognitive platform and/or platform product (including using an APP) that is configured to set baseline metrics of CSI levels/attributes in APP session(s) based on measurements nData indicative of physiological condition and/or cognition condition (including indicators of neuropsychological disorders), to increase accuracy of assessment and efficiency of treatment. The CSIs may be used to calibrate a nData component to individual user dynamics of nData.

An example system, method, and apparatus according to the principles herein includes a cognitive platform and/or platform product (including using an APP) that is configured to use nData to detect states of attentiveness/inattentiveness, alertness, vigilance, and/or fatigue, to optimize delivery of CSIs related to treatment or assessment.

An example system, method, and apparatus according to the principles herein includes a cognitive platform and/or platform product (including using an APP) that is configured to use analysis of nData with CSI cData to detect and direct attention to specific CSIs related to treatment or assessment through subtle or overt manipulation of CSIs.

An example system, method, and apparatus according to the principles herein includes a cognitive platform and/or platform product (including using an APP) that is configured to use analysis of CSIs patterns of cData with nData within or across assessment or treatment sessions to generate user profiles (including profiles of ideal, optimal, or desired user responses) of cData and nData and manipulate CSIs across or within sessions to guide users to replicate these profiles.

An example system, method, and apparatus according to the principles herein includes a cognitive platform and/or platform product (including using an APP) that is configured to monitor nData for indicators of parameters related to user engagement and to optimize the cognitive load generated by the CSIs to align with time in an optimal engaged state to maximize neural plasticity and transfer of benefit resulting from treatment. As used herein, the term "neural plasticity" refers to targeted re-organization of the central nervous system.

An example system, method, and apparatus according to the principles herein includes a cognitive platform and/or platform product (including using an APP) that is configured to monitor nData indicative of anger and/or frustration to promote continued user interaction (also referred to as "play") with the cognitive platform by offering alternative CSIs or disengagement from CSIs.

An example system, method, and apparatus according to the principles herein includes a cognitive platform and/or platform product (including using an APP) that is configured to change CSI dynamics within or across assessment or treatment sessions to optimize nData related to cognition or other physiological or cognitive aspects of the user.

An example system, method, and apparatus according to the principles herein includes a cognitive platform and/or platform product (including using an APP) that is configured to adjust the CSIs or CSI cognitive load if nData signals of task automation are detected, or the physiological measurements that relate to task learning show signs of attenuation.

An example system, method, and apparatus according to the principles herein includes a cognitive platform and/or platform product (including using an APP) that is configured to combine signals from CSI cData with nData to optimize individualized treatment promoting improvement of indicators of cognitive abilities, and thereby, cognition.

An example system, method, and apparatus according to the principles herein includes a cognitive platform and/or platform product (including using an APP) that is configured to use a profile of nData to confirm/verify/authenticate a user's identity.

An example system, method, and apparatus according to the principles herein includes a cognitive platform and/or platform product (including using an APP) that is configured to use nData to detect positive emotional response to CSIs in order to catalog individual user preferences to customize CSIs to optimize enjoyment and promote continued engagement with assessment or treatment sessions.

An example system, method, and apparatus according to the principles herein includes a cognitive platform and/or platform product (including using an APP) that is configured to generate user profiles of cognitive improvement (such as but not limited to, user profiles associated with users classified or known to exhibit improved working memory, attention, processing speed, and/or perceptual detection/discrimination), and deliver a treatment that adapts CSIs to optimize the profile of a new user as confirmed by profiles from nData.

An example system, method, and apparatus according to the principles herein includes a cognitive platform and/or platform product (including using an APP) that is configured to provide to a user a selection of one or more profiles configured for cognitive improvement.

An example system, method, and apparatus according to the principles herein includes a cognitive platform and/or platform product (including using an APP) that is configured to monitor nData from auditory and visual physiological measurements to detect interference from external environmental sources that may interfere with the assessment or treatment being performed by a user using a cognitive platform or program product.

An example system, method, and apparatus according to the principles herein includes a cognitive platform and/or platform product (including using an APP) that is configured to monitor nData from device auditory and visual measurements of the environment to detect interference from external environmental sources that may interfere with the assessment or treatment being performed by a user using a cognitive platform or program product, and accordingly adjust the platform or product, or notify the user to change environmental conditions or postpone until more suitable.

An example system, method, and apparatus according to the principles herein includes a cognitive platform and/or platform product (including using an APP) that is configured to use cData and/or nData (including metrics from analyzing the data) as a determinant or to make a decision as to whether a user (including a patient using a medical device) is likely to respond or not to respond to a treatment (such as but not limited to a cognitive treatment and/or a treatment using a biologic, a drug or other pharmaceutical agent). For example, the system, method, and apparatus can be configured to select whether a user (including a patient using a medical device) should receive treatment based on specific physiological or cognitive measurements that can be used as signatures that have been validated to predict efficacy in a given individual or certain individuals of the population (e.g., individual(s) classified to a given group the immune-mediated or neurodegenerative disease). Such an example system, method, and apparatus configured to perform the analysis (and associated computation) described herein can be used as a biomarker to perform monitoring and/or screening. As a non-limiting example, the example system, method and apparatus configured to provide a provide a quantitative measure of the degree of efficacy of a cognitive treatment (including the degree of efficacy in conjunction with use of a biologic, a drug or other pharmaceutical agent) for a given individual or certain individuals of the population (e.g., individual(s) classified to a given group based on status of the immune-mediated disease). In some examples, the individual or certain individuals of the population may be classified as having a certain neurodegenerative condition.

The non-limiting example classifier model can be trained to generate predictors of the status of the immune-mediated or neurodegenerative disease of individuals using training cData and corresponding nData, and based on metrics collected from at least one interaction of users with an example cognitive platform and/or platform product. The training nData can include data indicative of the status of the immune-mediated disease and age of each user that corresponds to cData collected for a given user (such as but not limited to that user's score from at least one interaction with any example cognitive platform and/or platform product herein). In some examples, the nData can include data indicative of the gender of the user. In other examples, the nData collected can be indicative of compliance or efficacy, in consideration cognitive treatment adjustment. For example, the cData can be collected based on a limited user interaction, e.g., on the order of a few minutes, with any example cognitive platform and/or platform product herein. The length of time of the limited user interaction can be, e.g., about 5 minutes, about 7 minutes, about 10 minutes, about 15 minutes, about 20 minutes, or about 30 minutes. The example cognitive platform and/or platform product can be configured to implement an assessment session (such as but not limited to an assessment implemented using a Project: EVO™ platform).

Non-limiting example system, method, and apparatus according to the principles herein also provide a cognitive platform and/or platform product that is configured to implement an example classifier model that is configured to identify individuals having a positive status of the immune-mediated disease versus a negative status of the immune-mediated disease with a high degree of accuracy based on measurement data (including cData) from a plurality of user interactions with the example cognitive platform and/or platform product. For example, the example classifier model can be configured to identify individuals that have positive status of the immune-mediated disease with about a 83% degree of accuracy, and to identify individuals that have negative status of the immune-mediated disease with about a 79% degree of accuracy, based on measurement data (including cData) from comparing baseline performance data in the first moments of the user performance of a first assessment using the example cognitive platform and/or platform product with values of performance data from the user performance of three (3) subsequent assessments using the example cognitive platform and/or platform product.

The non-limiting example classifier model according to the principles herein can be trained to generate predictors of the status of the immune-mediated disease of individuals using training cData and corresponding nData, and based on metrics collected from a plurality of interactions of users with an example cognitive platform and/or platform product. The training nData can includes data indicative of the status of the immune-mediated disease, and age of each user. In some examples, the nData can include data indicative of the gender of the user. The corresponding cData is collected for a given user (such as but not limited to that user's score from at least one interaction with any example cognitive platform and/or platform product herein). For example, the cData can be collected based on a plurality of interaction sessions of a user using a cognitive platform and/or platform product herein, e.g., two or more interaction sessions. The length of time of each interaction session can be, e.g., about 5 minutes, about 7 minutes, about 10 minutes, about 15 minutes, about 20 minutes, or about 30 minutes. The example cognitive platform and/or platform product can be configured to implement the plurality of assessment sessions (such as but not limited to an assessment implemented using a Project: EVO™ platform).

Figure 2:
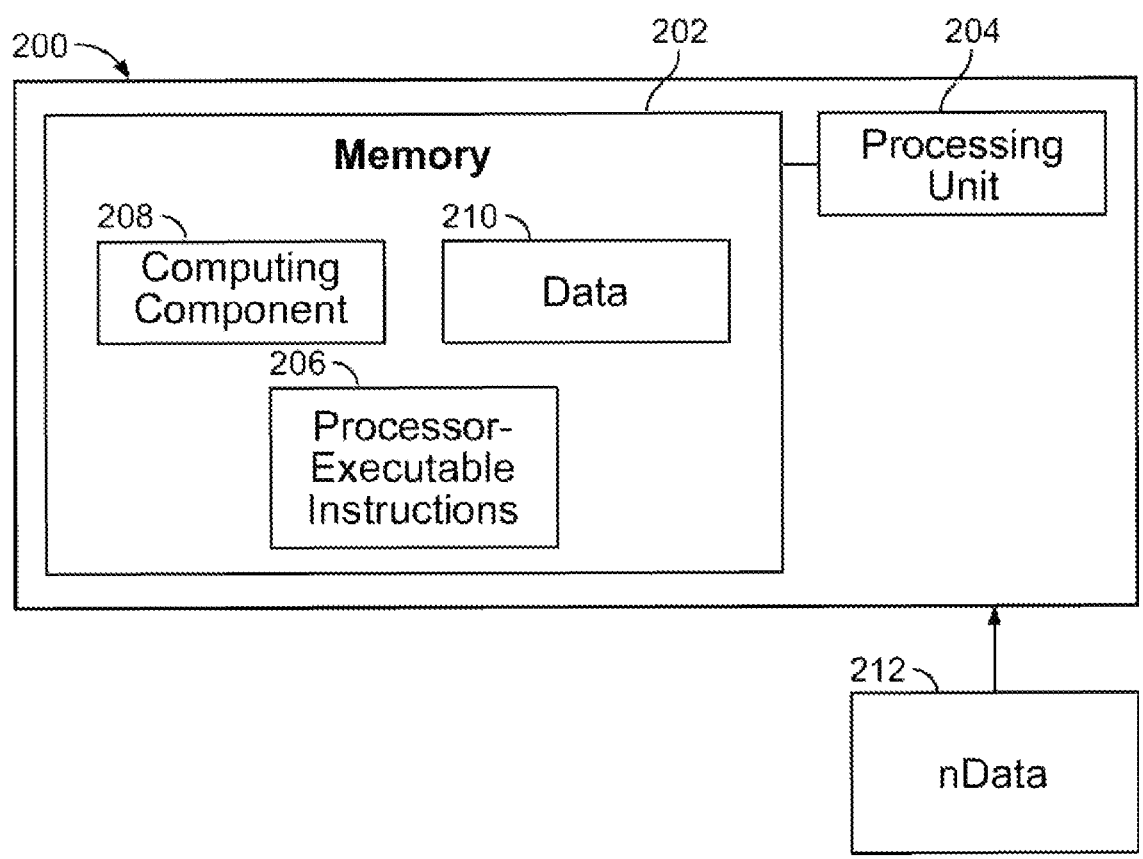
FIG. 2 is a block diagram of an example computing device, according to the principles herein.

As described hereinabove, the example systems, methods, and apparatus according to the principles herein can be implemented, using at least one processing unit of a programmed computing device, to provide the cognitive platform and/or platform product. FIG. 2 shows an example apparatus 200 according to the principles herein that can be used to implement the cognitive platform and/or platform product including the classifier model described hereinabove herein. The example apparatus 100 includes at least one memory 202 and at least one processing unit 204. The at least one processing unit 204 is communicatively coupled to the at least one memory 202.

Example memory 202 can include, but is not limited to, hardware memory, non-transitory tangible media, magnetic storage disks, optical disks, flash drives, computational device memory, random access memory, such as but not limited to DRAM, SRAM, EDO RAM, any other type of memory, or combinations thereof. Example processing unit 204 can include, but is not limited to, a microchip, a processor, a microprocessor, a special purpose processor, an application specific integrated circuit, a microcontroller, a field programmable gate array, any other suitable processor, or combinations thereof.

The at least one memory 202 is configured to store processor-executable instructions 206 and a computing component 208. In a non-limiting example, the computing component 208 can be used to analyze the cData and/or nData received from the cognitive platform and/or platform product coupled with the one or more physiological or monitoring components and/or cognitive testing components as described herein. As shown in FIG. 2, the memory 202 also can be used to store data 210, such as but not limited to the nData 212 (including computation results from application of an example classifier model, measurement data from measurement(s) using one or more physiological or monitoring components and/or cognitive testing components) and/or data indicative of the response of an individual to the one or more tasks (cData), including responses to tasks rendered at a graphical user interface of the apparatus 100 and/or tasks generated using an auditory, tactile, or vibrational signal from an actuating component coupled to or integral with the apparatus 200. The data 210 can be received from one or more physiological or monitoring components and/or cognitive testing components that are coupled to or integral with the apparatus 200.

In a non-limiting example, the at least one processing unit 204 executes the processor-executable instructions 206 stored in the memory 202 at least to analyze the cData and/or nData received from the cognitive platform and/or platform product coupled with the one or more physiological or monitoring components and/or cognitive testing components as described herein, using the computing component 208. The at least one processing unit 204 also can be configured to execute processor-executable instructions 206 stored in the memory 202 to apply the example classifier model to the cDdata and nData, to generate computation results indicative of the classification of an individual according to likelihood of onset of an immune-mediated or neurodegenerative condition, and/or likelihood of onset and/or stage of progression of a neurodegenerative condition (including an executive function disorder). The at least one processing unit 204 also executes processor-executable instructions 206 to control a transmission unit to transmit values indicative of the analysis of the cData and/or nData received from the cognitive platform and/or platform product coupled with the one or more physiological or monitoring components and/or cognitive testing components as described herein, and/or controls the memory 202 to store values indicative of the analysis of the cData and/or nData.

In another non-limiting example, the at least one processing unit 204 executes the processor-executable instructions 206 stored in the memory 202 at least to apply signal detection metrics in computer-implemented adaptive response-deadline procedures.

Figure 3:
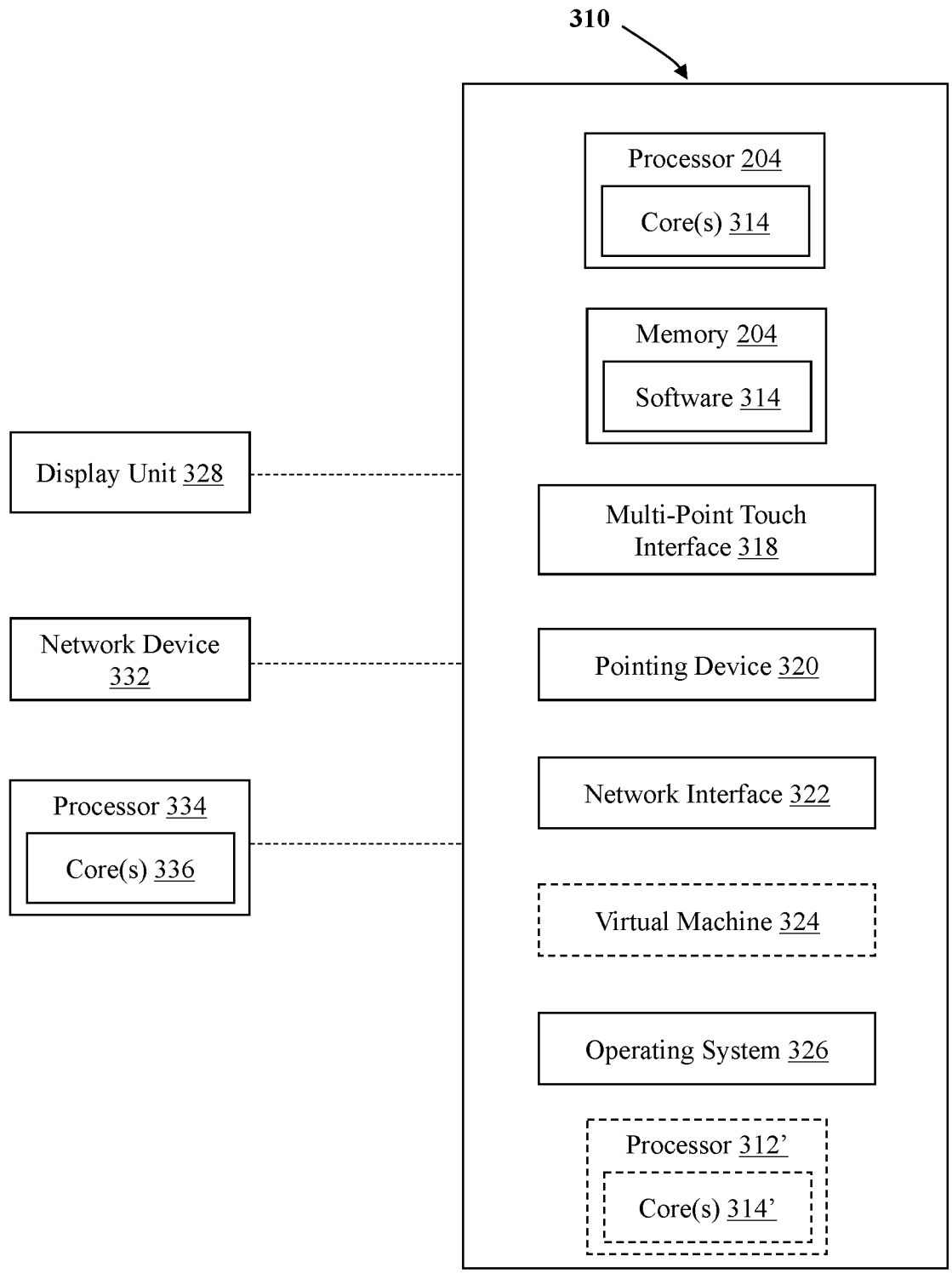
FIG. 3 is a block diagram of an exemplary computer system, according to the principles herein.

FIG. 3 is a block diagram of an example computing device 310 that can be used as a computing component according to the principles herein. In any example herein, computing device 310 can be configured as a console that receives user input to implement the computing component, including to apply the signal detection metrics in computer-implemented adaptive response-deadline procedures. For clarity, FIG. 3 also refers back to and provides greater detail regarding various elements of the example system of FIG. 2. The computing device 310 can include one or more non-transitory computer-readable media for storing one or more computer-executable instructions or software for implementing examples. The non-transitory computer-readable media can include, but are not limited to, one or more types of hardware memory, non-transitory tangible media (for example, one or more magnetic storage disks, one or more optical disks, one or more flash drives), and the like. For example, memory 202 included in the computing device 310 can store computer-readable and computer-executable instructions or software for performing the operations disclosed herein. For example, the memory 202 can store a software application 340 which is configured to perform various of the disclosed operations (e.g., analyze cognitive platform and/or platform product measurement data and response data, apply an example classifier model, or performing a computation). The computing device 310 also includes configurable and/or programmable processor 204 and an associated core 314, and optionally, one or more additional configurable and/or programmable processing devices, e.g., processor(s) 312' and associated core(s) 314' (for example, in the case of computational devices having multiple processors/cores), for executing computer-readable and computer-executable instructions or software stored in the memory 202 and other programs for controlling system hardware. Processor 204 and processor(s) 312' can each be a single core processor or multiple core (314 and 314') processor.

Virtualization can be employed in the computing device 310 so that infrastructure and resources in the console can be shared dynamically. A virtual machine 324 can be provided to handle a process running on multiple processors so that the process appears to be using only one computing resource rather than multiple computing resources. Multiple virtual machines can also be used with one processor.

Memory 202 can include a computational device memory or random access memory, such as but not limited to DRAM, SRAM, EDO RAM, and the like. Memory 202 can include a non-volatile memory, such as but not limited to a hard-disk or flash memory. Memory 202 can include other types of memory as well, or combinations thereof.

In a non-limiting example, the memory 202 and at least one processing unit 204 can be components of a peripheral device, such as but not limited to a dongle (including an adapter) or other peripheral hardware. The example peripheral device can be programmed communicate with or otherwise couple to a primary computing device, to provide the functionality of any of the example cognitive platform and/or platform product, apply an example classifier model, and implement any of the example analyses (including the associated computations) described herein. In some examples, the peripheral device can be programmed to directly communicate with or otherwise couple to the primary computing device (such as but not limited to via a USB or HDMI input), or indirectly via a cable (including a coaxial cable), copper wire (including, but not limited to, PSTN, ISDN, and DSL), optical fiber, or other connector or adapter. In another example, the peripheral device can be programmed to communicate wirelessly (such as but not limited to Wi-Fi or Bluetooth®) with primary computing device. The example primary computing device can be a smartphone (such as but not limited to an iPhone®, a BlackBerry®, or an Android™-based smartphone), a television, a workstation, a desktop computer, a laptop, a tablet, a slate, an electronic-reader (e-reader), a digital assistant, or other electronic reader or hand-held, portable, or wearable computing device, or any other equivalent device, an Xbox®, a Wii®, or other equivalent form of computing device.

A user can interact with the computing device 310 through a visual display unit 328, such as a computer monitor, which can display one or more user interfaces 330 that can be provided in accordance with example systems and methods. The computing device 310 can include other I/O devices for receiving input from a user, for example, a keyboard or any suitable multi-point touch interface 318, a pointing device 320 (e.g., a mouse), a camera or other image recording device, a microphone or other sound recording device, an accelerometer, a gyroscope, a sensor for tactile, vibrational, or auditory signal, and/or at least one actuator. The keyboard 318 and the pointing device 320 can be coupled to the visual display unit 328. The computing device 310 can include other suitable conventional I/O peripherals.

The computing device 310 can also include one or more storage devices 334 (including a single core processor or multiple core processor 336), such as a hard-drive, CD-ROM, or other computer readable media, for storing data and computer-readable instructions and/or software that perform operations disclosed herein. Example storage device 334 (including a single core processor or multiple core processor 336) can also store one or more databases for storing any suitable information required to implement example systems and methods. The databases can be updated manually or automatically at any suitable time to add, delete, and/or update one or more items in the databases.

The computing device 310 can include a network interface 322 configured to interface via one or more network devices 332 with one or more networks, for example, Local Area Network (LAN), metropolitan area network (MAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 322 can include a built-in network adapter, network interface card, PCMCIA network card, card bus network adapter, wireless network adapter, USB network adapter, modem or any other device suitable for interfacing the computing device 310 to any type of network capable of communication and performing the operations described herein. Moreover, the computing device 310 can be any computational device, such as a smartphone (such as but not limited to an iPhone®, a BlackBerry®, or an Android™-based smartphone), a television, a workstation, a desktop computer, a server, a laptop, a tablet, a slate, an electronic-reader (e-reader), a digital assistant, or other electronic reader or hand-held, portable, or wearable computing device, or any other equivalent device, an Xbox®, a Wii®, or other equivalent form of computing or telecommunications device that is capable of communication and that has or can be coupled to sufficient processor power and memory capacity to perform the operations described herein. The one or more network devices 332 may communicate using different types of protocols, such as but not limited to WAP (Wireless Application Protocol), TCP/IP (Transmission Control Protocol/Internet Protocol), NetBEUI (NetBIOS Extended User Interface), or IPX/SPX (Internetwork Packet Exchange/Sequenced Packet Exchange).

The computing device 310 can run any operating system 326, such as any of the versions of the Microsoft® Windows® operating systems, iOS® operating system, Android™ operating system, the different releases of the Unix and Linux operating systems, any version of the MacOS® for Macintosh computers, any embedded operating system, any real-time operating system, any open source operating system, any proprietary operating system, or any other operating system capable of running on the console and performing the operations described herein. In some examples, the operating system 326 can be run in native mode or emulated mode. In an example, the operating system 326 can be run on one or more cloud machine instances.

In any example herein, the adjustments to the type of tasks and/or CSIs can be made in real-time.

Examples of Cognitive Tools
Interference

FIGS. 4A-6D show non-limiting example user interfaces that can be rendered using example systems, methods, and apparatus herein to render the tasks and/or interferences (either or both with computer-implemented time-varying element) for user interactions. The non-limiting example user interfaces of FIGS. 4A-6D also can be used for one or more of: to display instructions to the individual for performing the tasks and/or interferences, interact with the computer-implemented time-varying element, to collect the data indicative of the individual's responses to the tasks and/or the interferences and the computer-implemented time-varying element, to show progress metrics, and to provide analysis metrics.

Figure 4A:
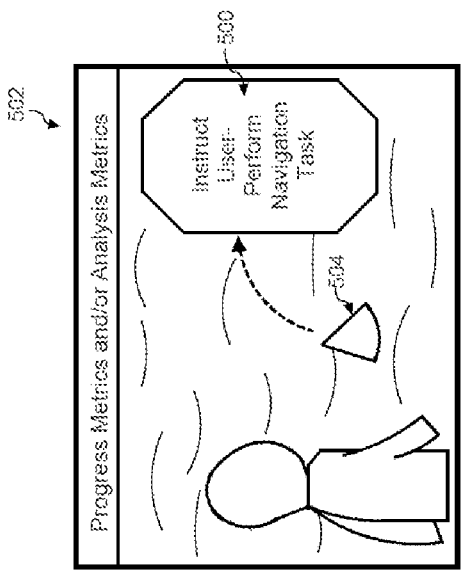
FIGS. 4A-4D show example user interfaces with instructions to a user that can be rendered to an example user interface, according to the principles herein.
Figure 4B:
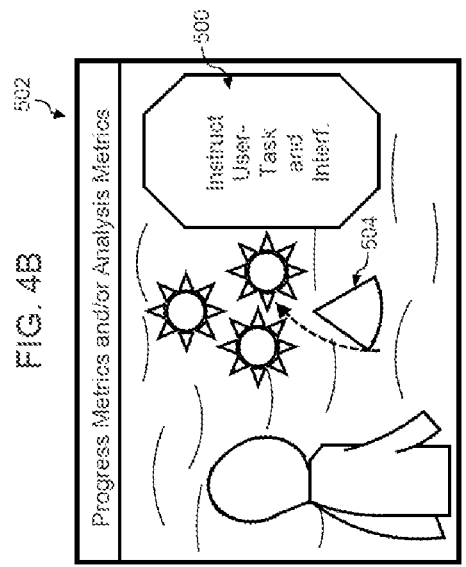
Figure 4C:
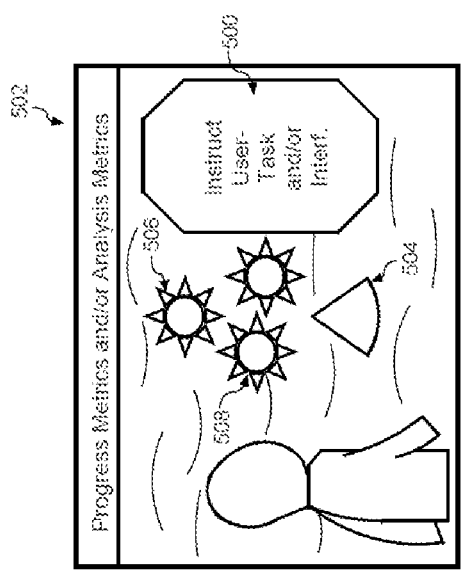
Figure 4D:
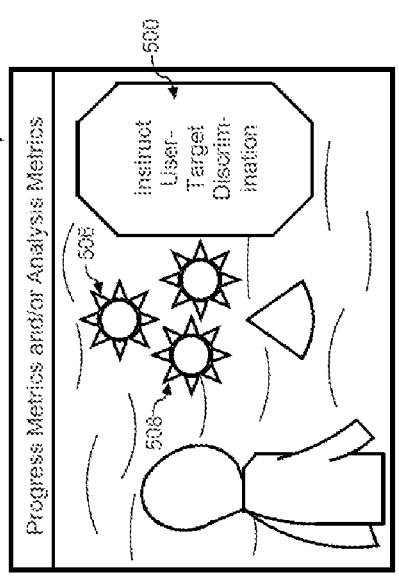

FIGS. 4A-4D show non-limiting example user interfaces rendered using example systems, methods, and apparatus herein. As shown in FIGS. 4A-4B, an example programmed processing unit can be used to render to the user interfaces (including graphical user interfaces) display features 500 for displaying instructions to the individual for performing the tasks and/or interference, and metric features 502 to show status indicators from progress metrics and/or results from application of analytics to the data collected from the individual's interactions (including the responses to tasks/interferences) to provide the analysis metrics. In any example systems, methods, and apparatus herein, the predictive model can be used to provide the analysis metrics provided as a response output. In any example systems, methods, and apparatus herein, the data collected from the user interactions can be used as input to train the predictive model. As shown in FIGS. 4A-4B, an example programmed processing unit also may be used to render to the user interfaces (including graphical user interfaces) an avatar or other processor-rendered guide 504 that an individual is required to control (such as but not limited to navigate a path or other environment in a visuo-motor task, and/or to select an object in a target discrimination task). As shown in FIG. 4B, the display features 500 can be used to instruct the individual what is expected to perform a navigation task while the user interface depicts (using the dashed line) the type of movement of the avatar or other processor-rendered guide 504 required for performing the navigation task. In an example, the navigation task may include milestone objects 510 that the individual is required to steer an avatar to cross or avoid, in order to determine the scoring. As shown in FIG. 4C, the display features 500 can be used to instruct the individual what is expected to perform a target discrimination task while the user interface depicts the type of object(s) 506 and 508 that may be rendered to the user interface, with one type of object 506 designated as a target while the other type of object 508 that may be rendered to the user interface is designated as a non-target, e.g., by being crossed out in this example. As shown in FIG. 4D, the display features 500 can be used to instruct the individual what is expected to perform both a navigation task as a primary task and a target discrimination as a secondary task (i.e., an interference) while the user interface depicts (using the dashed line) the type of movement of the avatar or other processor-rendered guide 504 required for performing the navigation task, and the user interface renders the object type designated as a target object 506 and the object type designated as a non-target object 508.

The measured data indicative of the individual's response to the single-tasking task rendered as a targeting task can be analyzed to provide quantitative insight into the cognitive domains of perception (detection & discrimination), motor function (detection & discrimination), impulsivity/inhibitory control, and visual working memory. The measured data indicative of the individual's response to the single-tasking task rendered as a navigation task can be analyzed to provide quantitative insight into the cognitive domains of visuomotor tracking and motor function. The measured data indicative of the individual's response to a primary task (rendered as a navigation task) in the presence of an interference (rendered as a targeting task), in a multi-tasking task, can be analyzed to provide quantitative insight into the cognitive domains of divided attention and interference management.

Figure 5A:
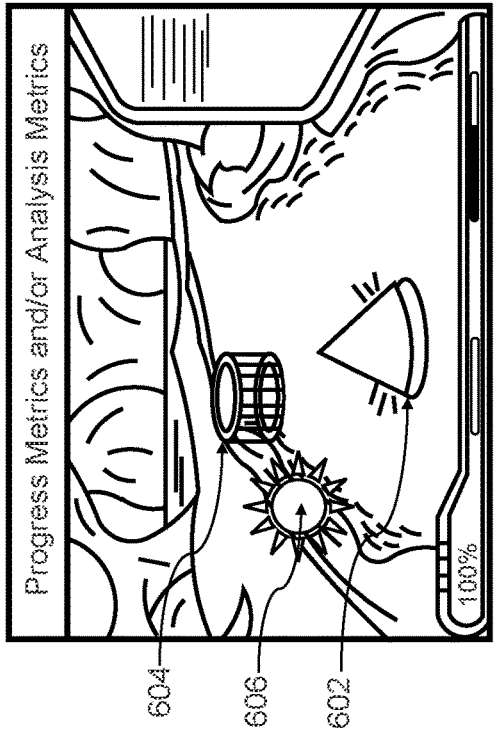
FIGS. 5A-5T show examples of the rendering of tasks and interferences at user interfaces, according to the principles herein.
Figure 5B:
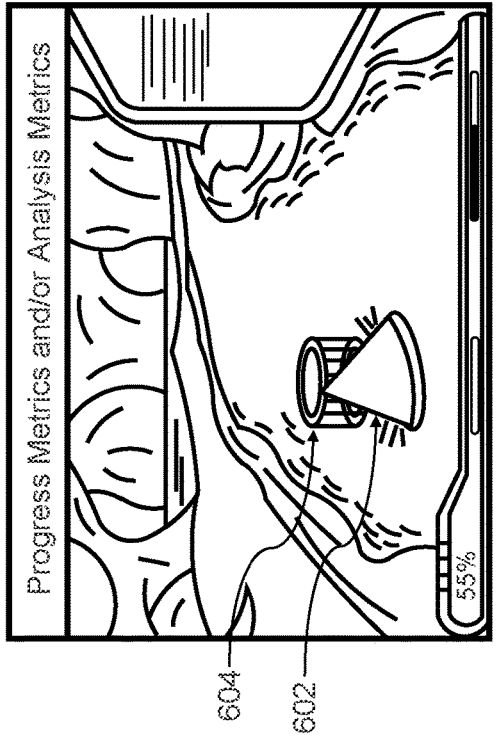
Figure 5C:
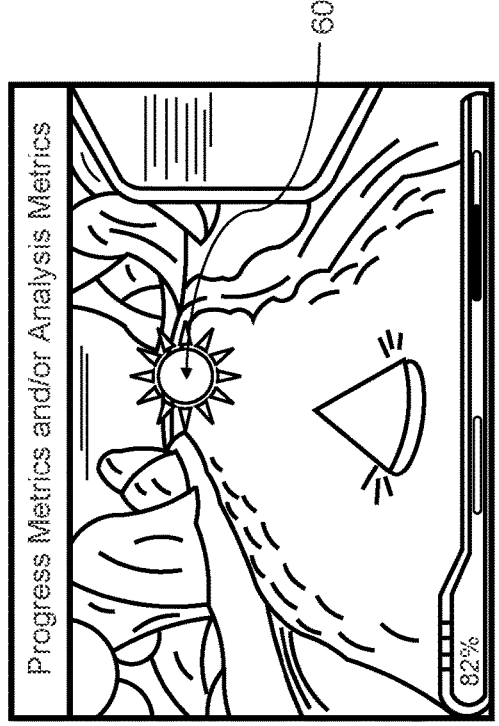
Figure 5D:
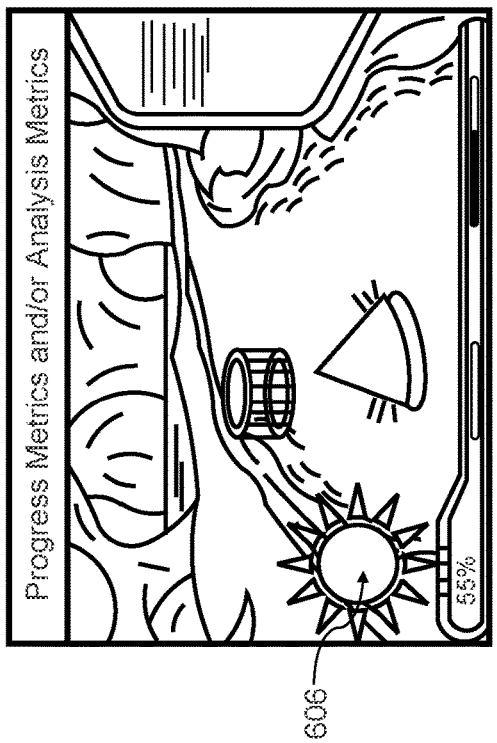
Figure 5E:
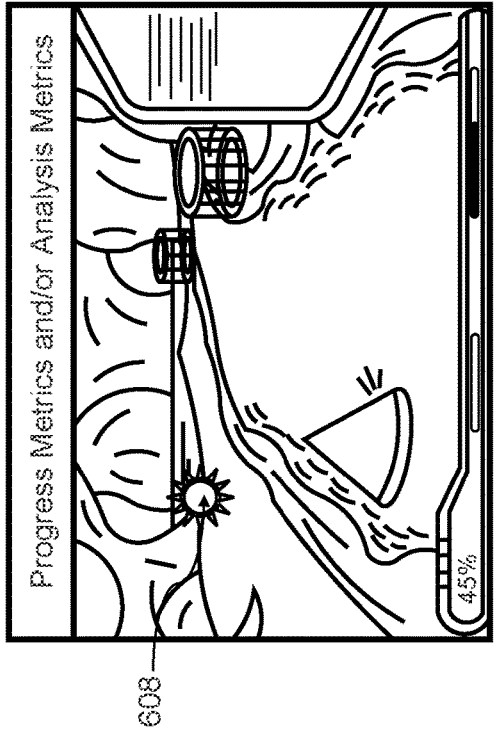
Figure 5F:
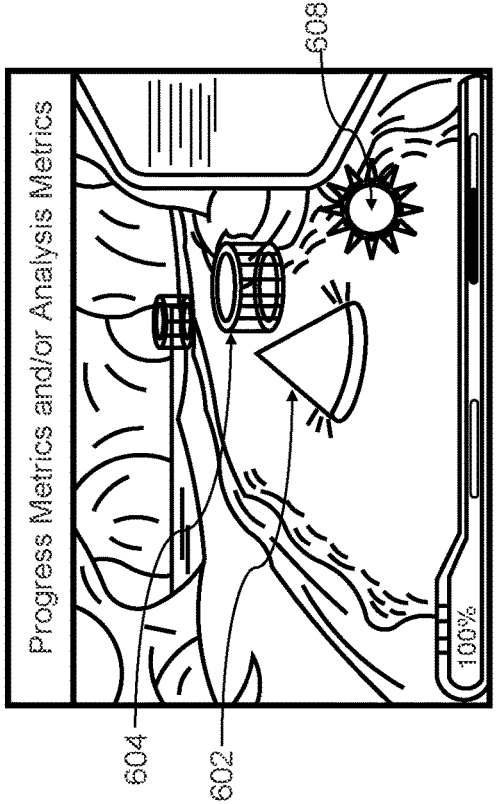
Figure 5G:
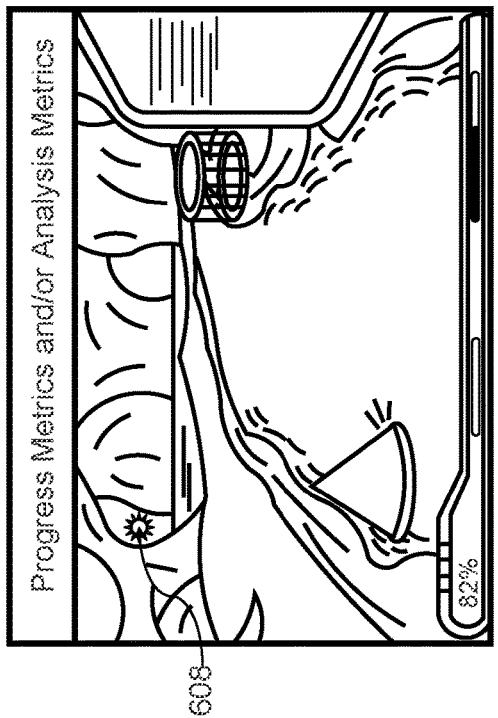
Figure 5H:
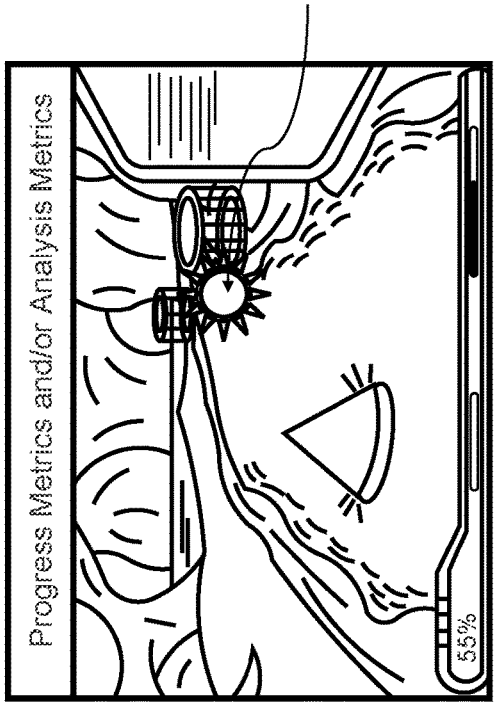
Figure 5I:
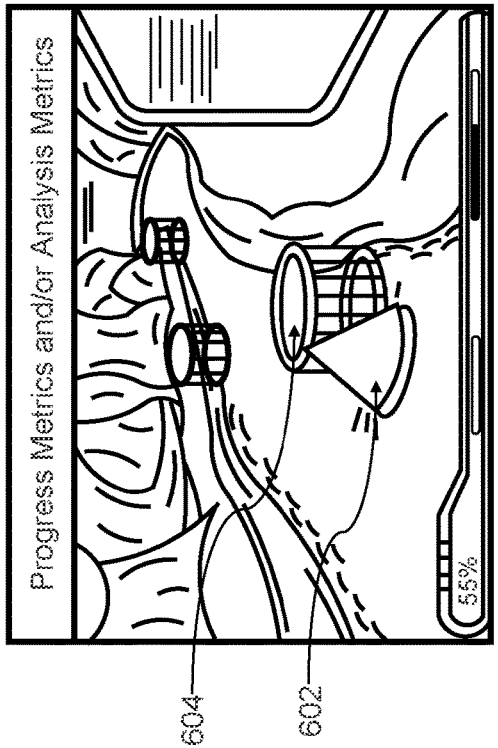
Figure 5J:
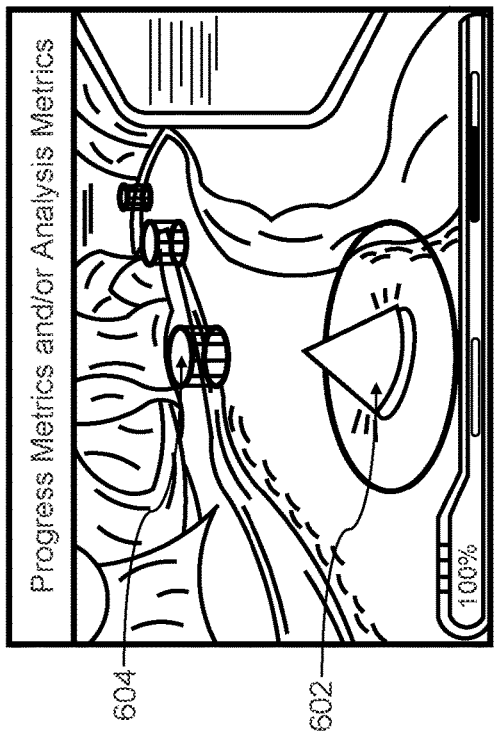
Figure 5K:
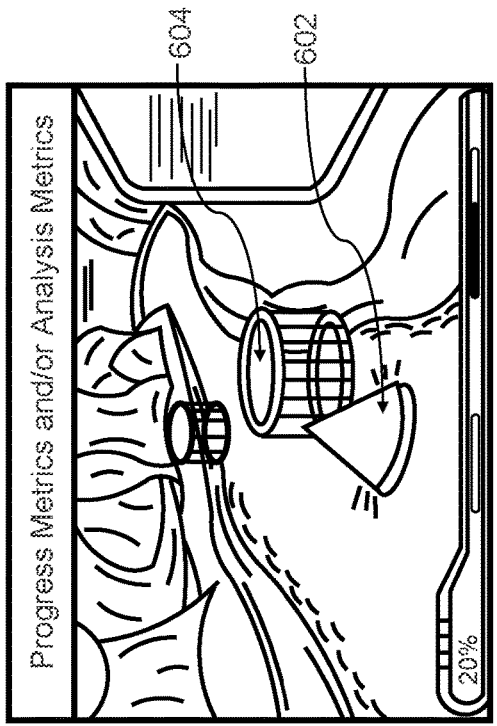
Figure 5L:
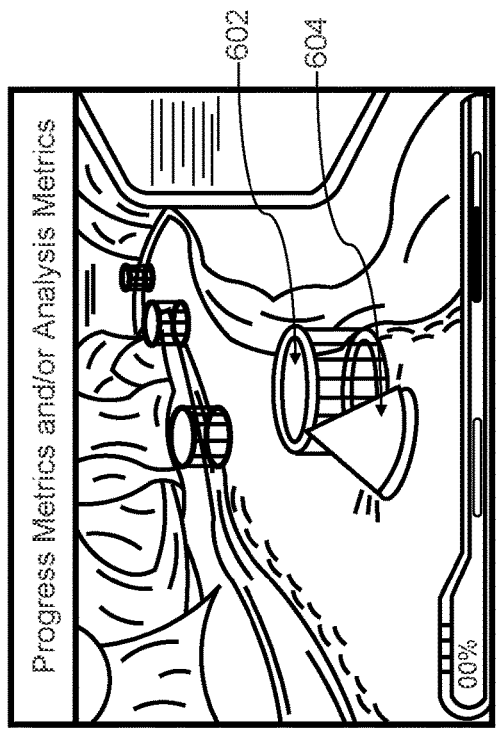
Figure 5M:
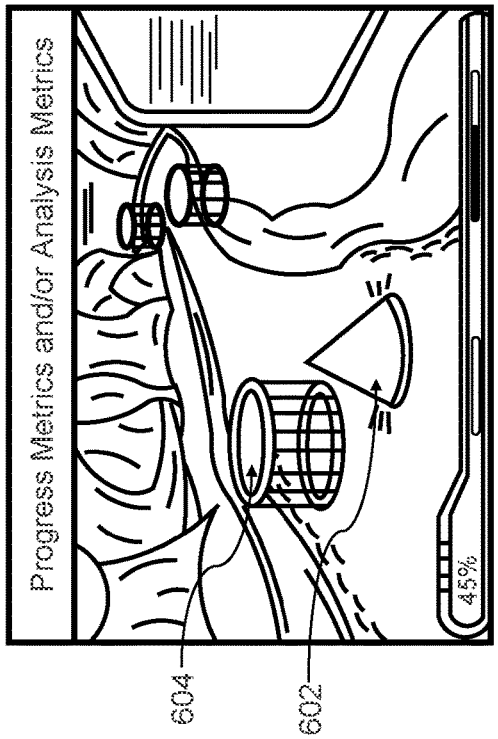
Figure 5N:
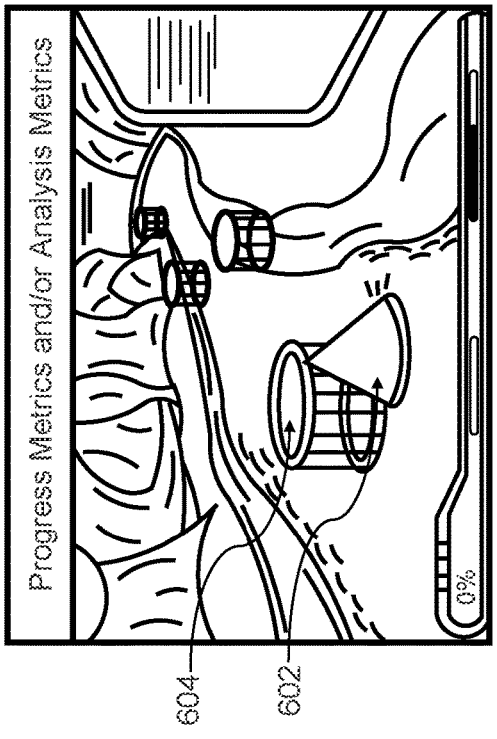
Figure 5O:
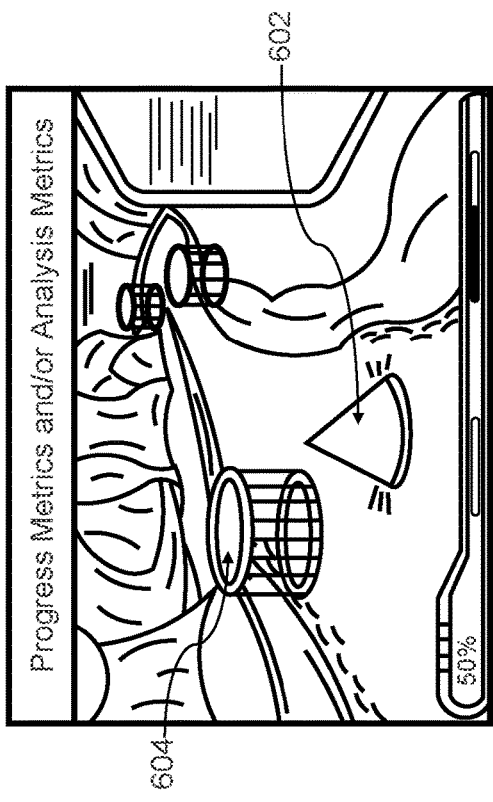
Figure 5P:
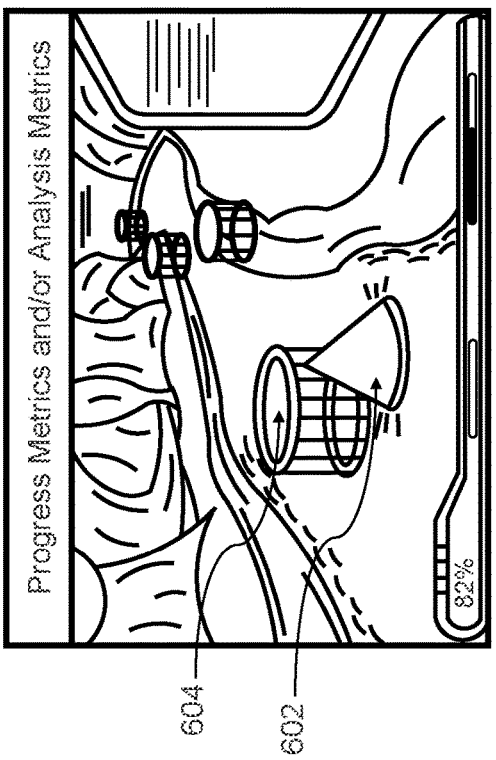
Figure 5Q:
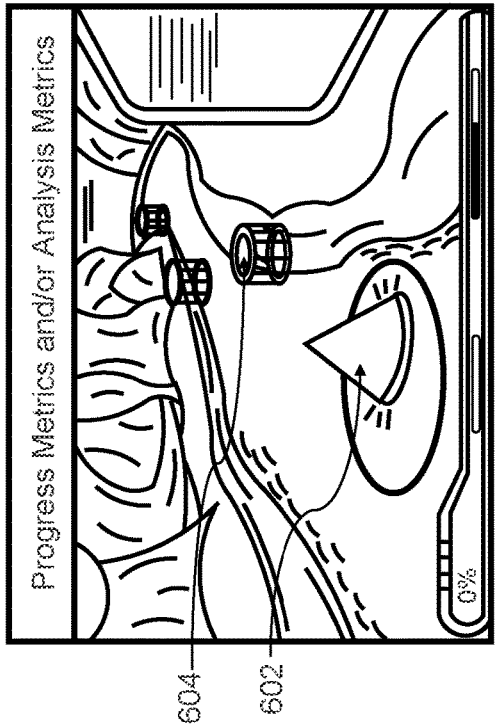
Figure 5R:
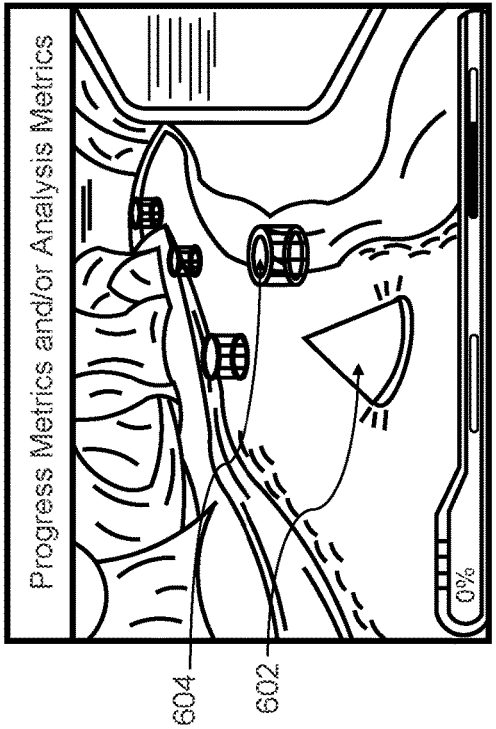
Figure 5S:
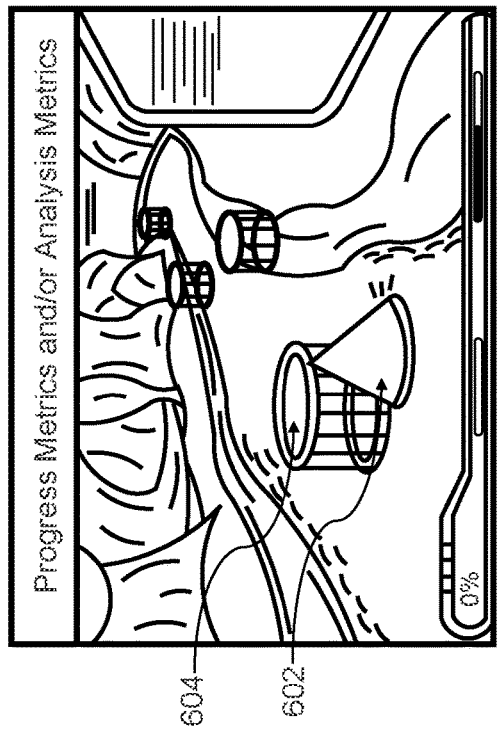
Figure 5T:
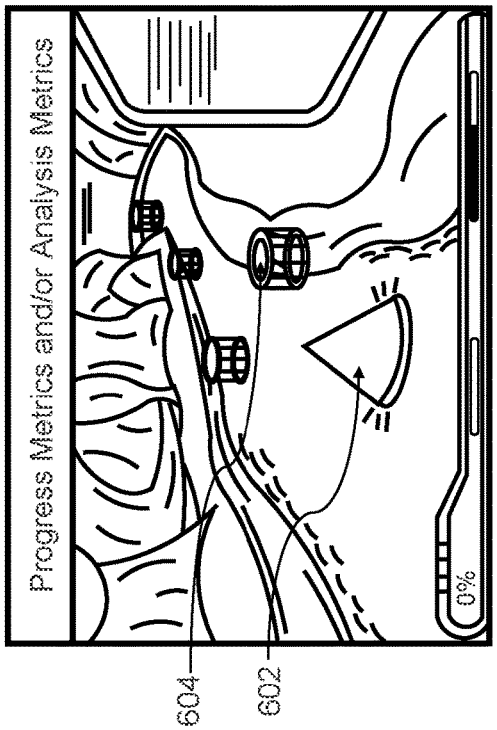
Figure 6A:
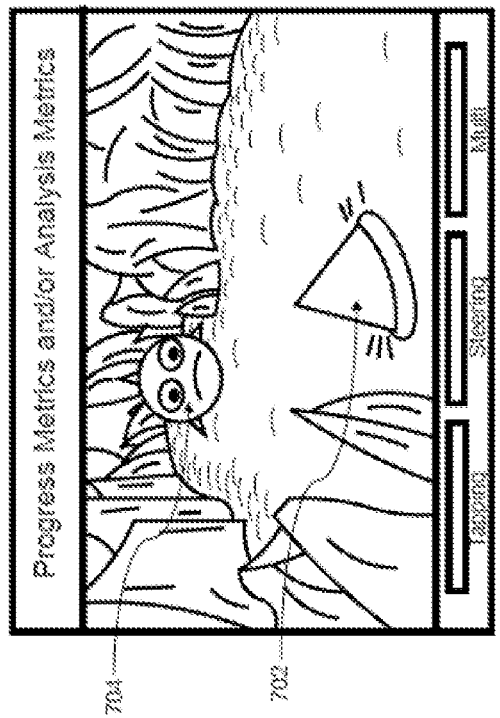
FIGS. 6A-6D show examples of the rendering of tasks and interferences at user interfaces, according to the principles herein.
Figure 6B:
Figure 6C:
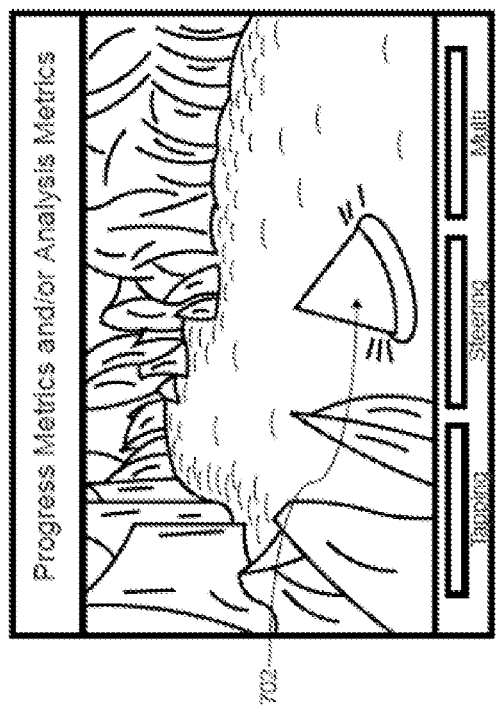
Figure 6D:
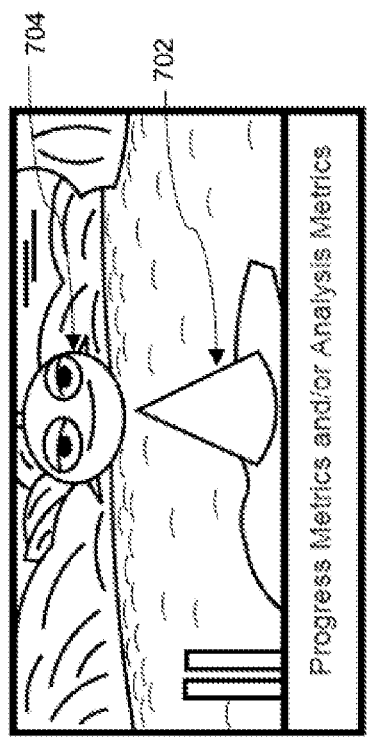

FIGS. 5A-5T show a non-limiting example of the dynamics of tasks and interferences that can be rendered at user interfaces, according to the principles herein. In this example, the primary task is a visuo-motor navigation task, and the interference is target discrimination (as a secondary task). As shown in FIGS. 5D, 5I-5K, and 5O-5Q, the individual is required to perform the navigation task by controlling the motion of the avatar 602 along a path that coincides with the milestone objects 604. FIGS. 5A-5T show a non-limiting example implementation where the individual is expected to actuate an apparatus or computing device (or other sensing device) to cause the avatar 602 to coincide with the milestone object 604 as the response in the navigation task, with scoring based on the success of the individual at crossing paths with (e.g., hitting) the milestone objects 604. In another example, the individual is expected to actuate an apparatus or computing device (or other sensing device) to cause the avatar 602 to miss the milestone object 604, with scoring based on the success of the individual at avoiding the milestone objects 604. FIGS. 5A-5C show the dynamics of a target object 606 (a star having a first type of pattern). FIGS. 5E-5H show the dynamics of a non-target object 608 (a star having a second type of pattern). FIGS. 5I-5T show the dynamics of other portions of the navigation task, where the individual is expected to guide the avatar 602 to cross paths with the milestone object 604 in the absence of an interference (an instance of a secondary task).

In the example of FIGS. 5A-5T, the processing unit of the example system, method, and apparatus is configured to receive data indicative of the individual's physical actions to cause the avatar 602 to navigate the path. For example, the individual may be required to perform physical actions to "steer" the avatar, e.g., by changing the rotational orientation or otherwise moving a computing device. Such action can cause a gyroscope or accelerometer or other motion or position sensor device to detect the movement, thereby providing measurement data indicative of the individual's degree of success in performing the navigation task.

In the example of FIGS. 5A-5C and 5E-5H, the processing unit of the example system, method, and apparatus is configured to receive data indicative of the individual's physical actions to perform the target discrimination task. For example, the individual may be instructed prior to a trial or other session to tap, or make other physical indication, in response to display of a target object 606, and not to tap to make the physical indication in response to display of a non-target object 608. In FIGS. 5A-5C and 5E-5H, the target discrimination task acts as an interference (i.e., an instance of a secondary task) to the primary navigation task, in an interference processing multi-tasking implementation. As described hereinabove, the example systems, methods, and apparatus can cause the processing unit to render a display feature to display the instructions to the individual as to the expected performance. As also described hereinabove, the processing unit of the example system, method, and apparatus can be configured to (i) receive the data indicative of the measure of the degree and type of the individual's response to the primary task substantially simultaneously as the data indicative of the measure of the degree and type of the individual's response to the interference is collected (whether the interference includes a target or a non-target), or (ii) to selectively receive data indicative of the measure of the degree and type of the individual's response to an interference that includes a target stimulus (i.e., an interruptor) substantially simultaneously (i.e., at substantially the same time) as the data indicative of the measure of the degree and type of the individual's response to the task is collected and to selectively not collect the measure of the degree and type of the individual's response to an interference that includes a non-target stimulus (i.e., a distraction) substantially simultaneously (i.e., at substantially the same time) as the data indicative of the measure of the degree and type of the individual's response to the task is collected.

FIGS. 6A-6D show other non-limiting examples of the dynamics of tasks and interferences that can be rendered at user interfaces, according to the principles herein. In this example, the primary task is a visuo-motor navigation task, and the interference is target discrimination (as an instance of a secondary task). Similarly to FIGS. 5A-5T, the individual is required to perform the navigation task by controlling the motion of the avatar 702 along a path. The individual is required to provide a response to the tasks in the presence or absence of an interference 704 (rendered as a target for discrimination).

In a non-limiting example, the adaptation of the difficulty of a task and/or interference may be adapted with each different stimulus that is presented as a computer-implemented time-varying element.

In another non-limiting example, the example system, method, and apparatus herein can be configured to adapt a difficulty level of a task and/or interference one or more times in fixed time intervals or in other set schedule, such as but not limited to each second, in 10 second intervals, every 30 seconds, or on frequencies of once per second, 2 times per second, or more (such as but not limited to 30 times per second).

In a non-limiting example of a visuo-motor task (a type of navigation task), one or more of navigation speed, shape of the course (changing frequency of turns, changing turning radius), and number and/or size of obstacles can be changed to modify the difficulty of a navigation game level, with the difficulty level increasing with increasing speed and/or increasing numbers and/or sizes of obstacles (including types of milestone objects (e.g., some milestone objects to avoid or some milestone objects to cross/coincide with).

In a non-limiting example, the difficulty level of a task and/or interference of a subsequent level can also be changed in real-time as feedback, e.g., the difficulty of a subsequent level can be increased or decreased in relation to the data indicative of the performance of the task.

In an example, the response recorded for the targeting task can be, but is not limited to, a touch, swipe or other gesture relative to a user interface or image collection device (including a touch-screen or other pressure sensitive screen, or a camera) to interact with a user interface. In another example, the response recorded for the targeting task can be, but is not limited to, user actions that cause changes in a position, orientation, or movement of a computing device including the cognitive platform, that is recorded using a sensor disposed in or otherwise coupled to the computing device (such as but not limited to a motion sensor or position sensor).

In this example and any other example herein, the cData and/or nData can be collected in real-time.

In this example and any other example herein, the adjustments to the type of tasks and/or CSIs can be made in real-time.

Navigation

FIGS. 7A-7D show non-limiting examples of computerized renderings of courses (paths) that present navigation tasks.

Figure 7A:
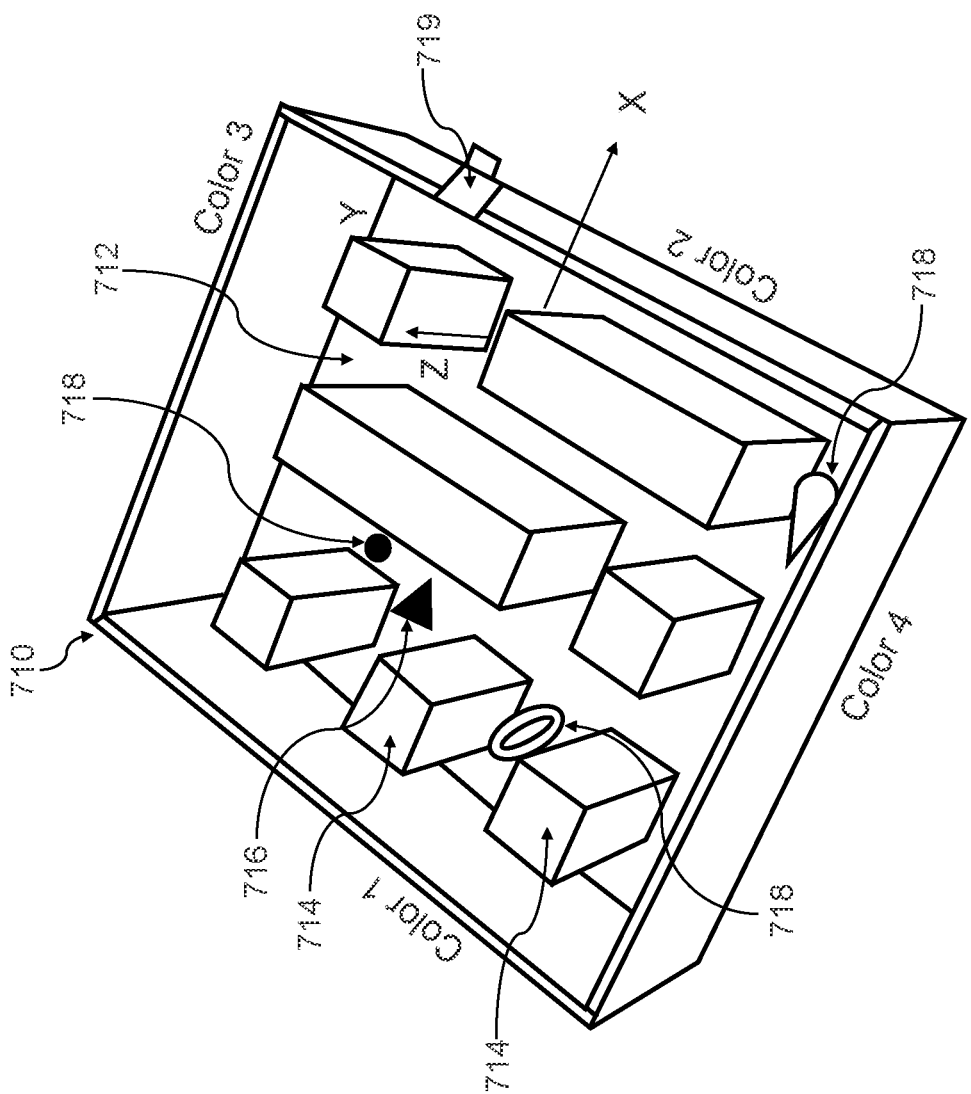
FIGS. 7A-7D show non-limiting examples of computerized renderings of courses that present navigation tasks, according to the principles herein.

FIG. 7A shows a non-limiting example of a computerized rendering of a course that can be used to present a navigation task according to the principles herein, including a route-learning task, or a relative-orientation task, or a way-finding task, or any combination thereof. In this example, the computing device is configured to present an elevated, overhead view of an environment 710 that includes one or more internal courses 712 and obstacles 714. In this example, portions of the course 712 are configured to include pathways and passageways that allow traversal of the user indicator (such as but not limited to an avatar or other guidable element 716). In this example, the environment is rendered as a city-block type structure, however, other example environments are encompassed in this disclosure. The Cartesian axes (x-, y-, and z-axes) directions in the environment are used merely as guides for the description in this disclosure, and are not intended to be limiting on the environment. The example environment also includes a number of strategically placed shaped objects 718 (such as a doughnut, a sphere, a cone, etc.) that a user is tasked to locate. In this example, the user is presented a perspective view of the landscape and obstacles that is sufficiently localized so that the user is required to make selections or decisions on strategy to traverse the course without benefit of an aerial view of the entire course or a significant portion of the course. The navigation task requires an individual to formulate a pathway about the strategically positioned obstacles 714 from an initial point to at least one of the shaped objects 718. The example environment can include one or more entryways 719 that either remain at a same location or at differing locations relative to the environment 710. The computing device can be configured to present instructions to the individual in a testing phase to indicate the shaped objects 718 to be located, and optionally to allow the user an exploration phase (including a guided route phase or a free-exploration phase) to become familiar with location and type of the obstacles 714 and shaped object 718 in the environment 710. The computing device also can be configured to provide an individual with an input device or other type of control element (including the joystick, steering wheel, buttons, or other controls described hereinabove) that allows the individual to traverse the course 712, including specifying and/or controlling one or more of the speed of movement, orientation, velocity, choice of navigation strategy, the wait or delay period or other period of inaction, prior to continuing in a given direction of a course or changing direction, time interval to complete a course, and/or frequency or number of times of referral to an aerial or elevated view of a landscape (including as a map), a measure of accuracy in recreating a previously learned route (e.g., in the one or more testing phases), a measure of accuracy of a user in using spatial memory rather than visual cues to orient the user indicator relative to (including to point back to) a specific location in space (such as but not limited to the point of origin of the given pre-specified navigation route), and/or a measure of the strategies employed in exploring and learning a novel environment. In any example herein, the measure can include values of any of these parameters as a function of time. As non-limiting examples, the performance metrics can include a measure of the degree of optimization of the path navigated by the individual through the course, such as determining the shortest path or near-shortest path through the course, the time to complete the task, or other scoring mechanism associated with a route-learning task, or a relative-orientation task, or a way-finding task, or any combination thereof (as described herein).

In an example implementation, the walls of the environment can be configured with differing colors, indicated as a color 1, color 2, color 3, and color 4, to provide a user with visual cues for navigating through the environment 710. For example, each can be a different color, two or more can be the same color, or all can be the same color. A first specific color can be used to indicate walls crossing the x-axis of the environment (e.g., color 3 and color 4 are the same), while a second, different specific color can be used to indicate walls crossing the y-axis of the environment (e.g., color 3 and color 4 are the same).

The computing device can be configured to collect data indicative of the performance metric that quantifies the navigation strategy (including path, speed, and number of turns and sweeping gazes) employed by the individual from the initial point ("A") or entryway 719 to reach one or more target locations, landmarks, shaped objects, or end-points ("B") in performing the route-learning task, way-finding task, or combination task. For example, the computing device can be configured to collect data indicative of the individual's decisions to proceed from the initial point ("A") or entryway 719 along the dashed line or the dotted line, the speed of movement, the orientation of the user indicator (such as but not limited to the avatar or other guidable element 716), among other measures (as described hereinabove). The data can be collected in the one or more testing phases. The data also can be collected in the exploration phase to provide a baseline or other comparison metric for computing the scores described herein. In the various examples, performance metrics that can be measured using the computing device can include data indicative of the speed of movement, orientation, velocity, choice of navigation strategy, wait or delay period, or other period of inaction, prior to continuing in a given direction of a course or changing direction, time interval to complete a course, and/or frequency or number of times of referral to an aerial or elevated view of a landscape (including as a map), including values of any of these parameters as a function of time. As another non-limiting example, the performance metrics can include a measure of the degree of optimization of the path navigated by the individual through the course, such as determining the shortest path or near-shortest path through the course, the time to complete the task, or other scoring mechanism associated with a route-learning task, or a relative-orientation task, or a way-finding task, or any combination thereof (as described herein).

As shown in the example of FIG. 7A, the course 712 may include one or more targets (such as shaped objects 718, landmarks, or other desired location) that the individual is instructed to locate in traversing the course 712. In this example, the performance metric may include a scoring based on a specific type of target located, and/or the total number of targets located and/or the time taken to locate the targets. In a non-limiting example, the individual may be instructed to navigate the course 712 such that the multiple targets are located in a specified sequence. In this example, the performance metric may include a scoring based on the number of targets located in sequence and/or the time taken to complete the sequence.

Figure 7B:
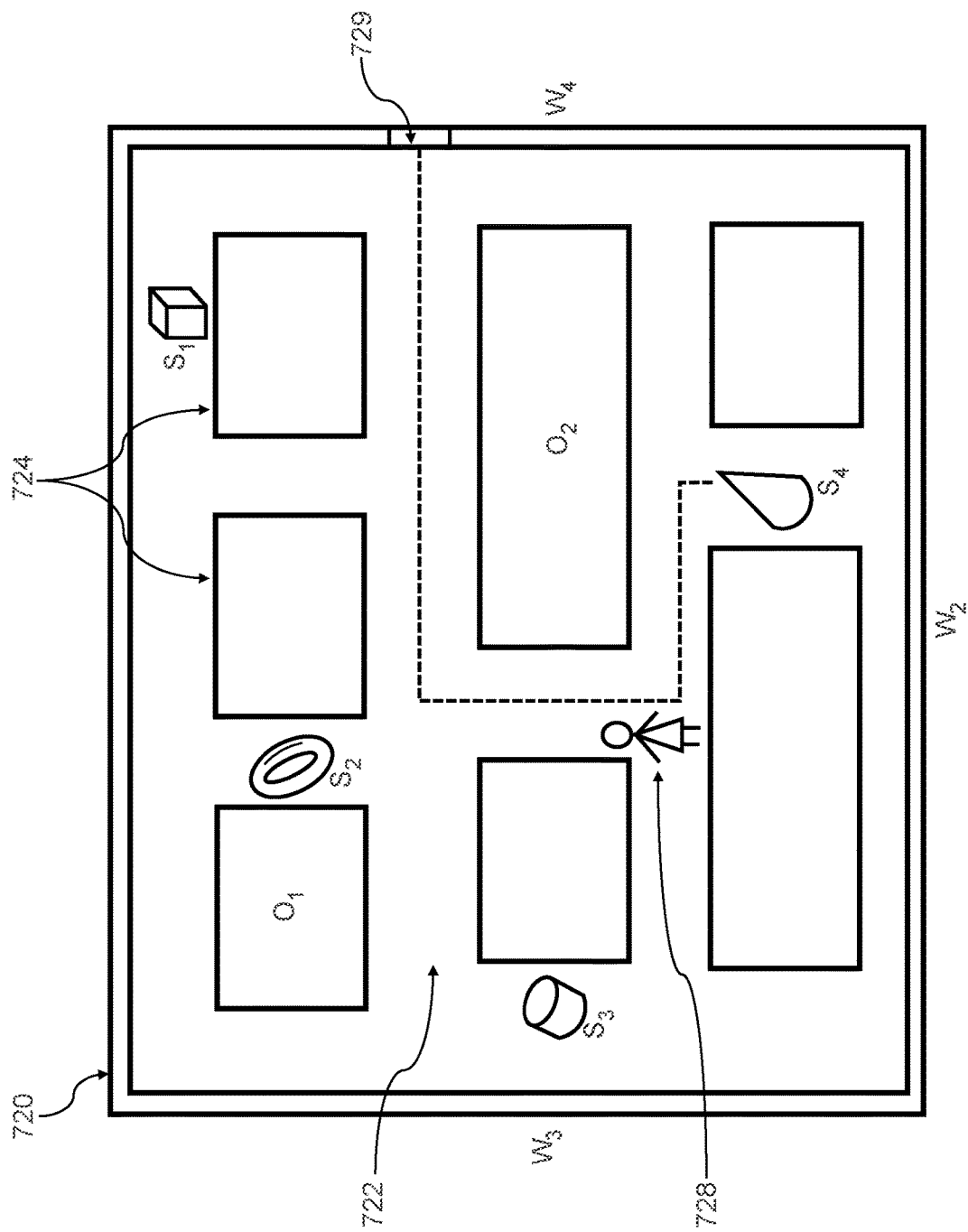

FIG. 7B shows a non-limiting example of another computerized rendering of an environment 720 that a computing device can render to present a navigation task according to the principles herein. In this example landscape 720, portions of the course 722 are defined by obstacles 724, and are configured to allow traversal of the user indicator (such as but not limited to an avatar or other guidable element 726) from a point of origin 729 to a specified target. As described hereinabove, the point of origin 729 may be at the same or different location relative to the environment between the two testing phases. As shown in FIG. 7B, the obstacles 724 can have differing cross-sectional shapes, such as a substantially square cross-section of obstacle $O_1$ compared to a longitudinal cross-section of obstacle $O_2$. In this example, the user is presented a perspective view of the landscape and obstacles that is sufficiently localized so that an individual is required to make selections or decisions on strategy to traverse the course without benefit of an aerial view of the entire course or a significant portion of the course. The computing device can be configured to collect data indicative of the individual's decision to proceed along the dashed line or the dotted line (such as but not limited to the forward or backtracking movement of a user in the testing phase of a route-learning task), and/or the speed of movement, and/or the orientation of the user indicator (such as but not limited to the avatar or other guidable element 726), such as but not limited to the point of origin pointing (or other indication) that may be required of a user in the testing phase of a route-learning task), among other measures. In this example, performance metrics that can be measured using the computing device relative to the localized landscape can include data indicative of one or more of the speed of movement, orientation, velocity, choice of navigation strategy, wait or delay period, or other period of inaction, prior to continuing in a given direction of a course or changing direction, time interval to complete a course, and/or frequency or number of times of referral to an aerial or elevated view of a landscape (including as a map), a measure of accuracy in recreating a previously learned route (e.g., in the one or more testing phases), a measure of accuracy of a user in using spatial memory rather than visual cues to orient the user indicator relative to (including to point back to) a specific location in space (such as but not limited to the point of origin of the given pre-specified navigation route), and/or a measure of the strategies employed in exploring and learning a novel environment. In any example herein, the measure can include values of any of these parameters as a function of time. As another non-limiting example, the performance metrics can include a measure of the degree of optimization of the path navigated by the individual through the course, such as but not limited to determining the shortest path or near-shortest path through the course.

The example environment 720 includes multiple target shaped objects $S_i$ (i=1, 2, 3, 4) that the individual is instructed to locate in traversing the course 722 from point of origin 729. In this example, the performance metric may include a scoring based on the success in locating a specific target object, the number of targets located (including from multiple testing phases), and/or the time taken to locate the target(s). In a non-limiting example, the individual may be instructed to navigate the course 722 such that the multiple targets are located in a specified sequence. In this example, the performance metric may include a scoring based on the number of targets located in sequence and/or the time taken to complete the sequence.

In an example way-finding task, a computing device can be configured to present an individual with the capability of changing, in at least one instance in a session, from a wider aerial view (such as but not limited to the view shown in FIGS. 7A-7B) to a more localized, perspective view (such as but not limited to the perspective views shown in FIGS. 9A-9U hereinbelow).

As a non-limiting example implementation of a way-finding task, an individual may be presented with an aerial view such as shown in FIG. 7A or 7B to obtain an overview of the course, but then be required to navigate the course from a more localized perspective view shown in FIGS. 9A-9U hereinbelow. In this example, an individual may be required to rely on allocentric navigate capabilities, to navigate the course by making selections and decisions from more localized, perspective views similar to that shown in FIGS. 9A-9U hereinbelow based on the spatial memory the individual forms from the wider aerial view of FIG. 7A or 7B.

Figure 7C:
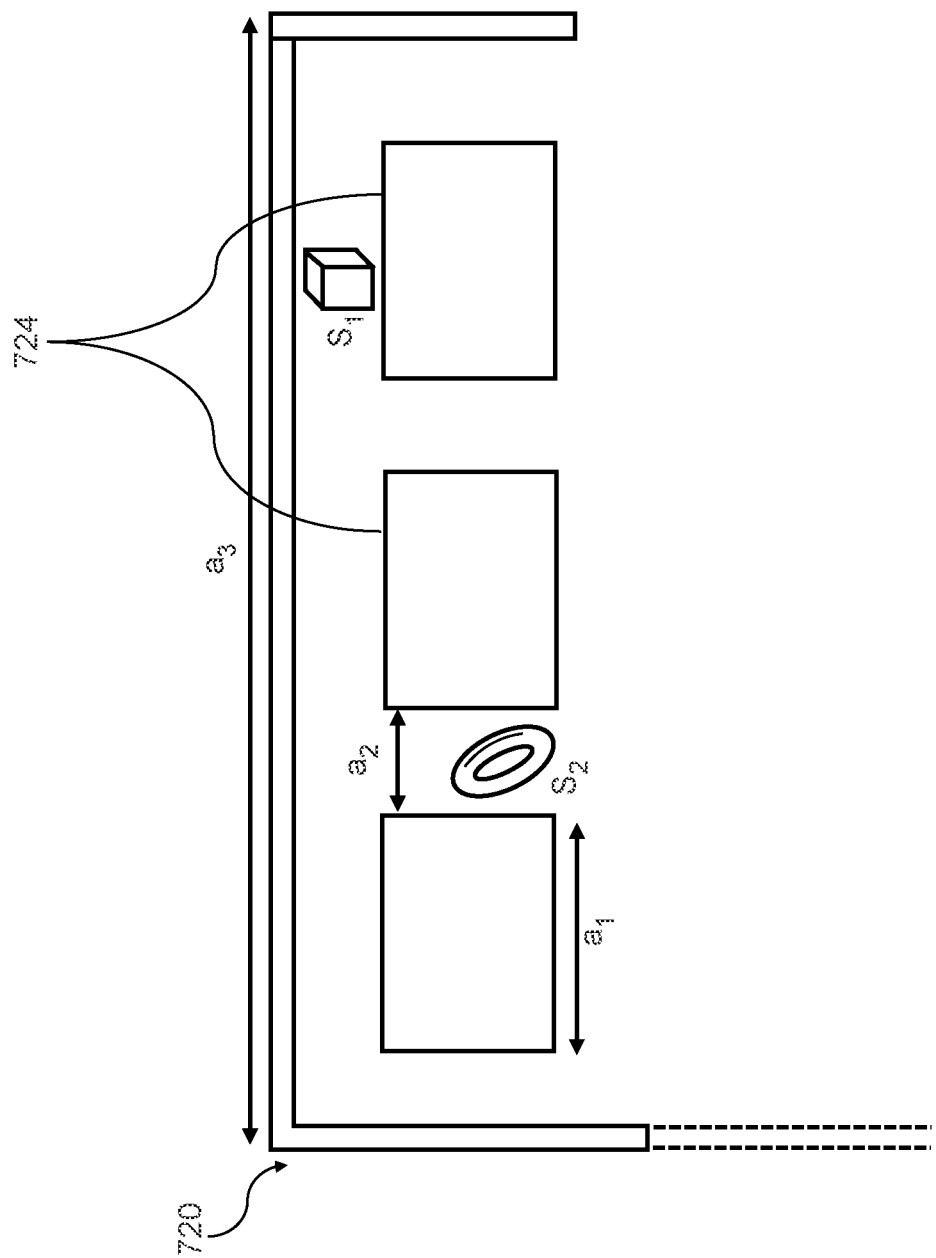

FIG. 7C shows a non-limiting example of the type of dimensional constraints that can be imposed on the passageways, obstacles, and dimensions of the environment. As shown in FIG. 7C, the width ($\alpha_1$) of the obstacles is greater than or about equal to the width ($\alpha_2$) of the passageway. In a non-limiting example, $\alpha_1$ is about twice $\alpha_2$. The width ($\alpha_1$) is also smaller than the length of environment wall ($\alpha_3$), such that no portion of the environment is rendered inaccessible by an obstacle. In a non-limiting example, $\alpha_1$ is about one-fourth or one-fifth of $\alpha_3$. While example proportionate values are given for the relative dimensions (width and lengths) of the passageway, obstacles, and environment walls, they are not intended to be limiting, other than to require that $\alpha_3 > \alpha_2 > \alpha_1$.

Figure 7D:
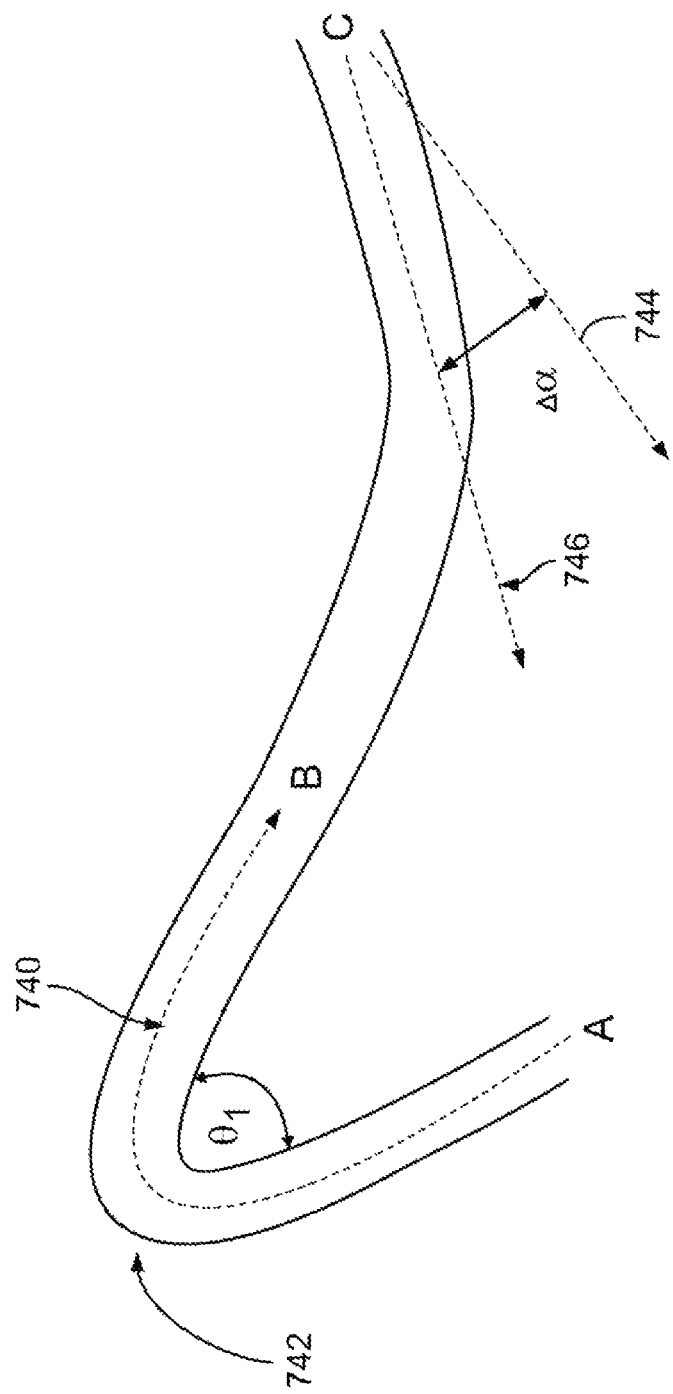

FIG. 7D shows a non-limiting example of a computerized environment, where the path 740 from point A to point B includes at least one turn 742 of a discrete angular amount (represented by angle $\theta_1$). In an non-limiting example of a task involving path integration (such as but not limited to dead-reckoning), a user is required to navigate from an initial point A to a target end-point (C) via the path, and from point C use an indicator to "point" back to or otherwise indicate the point of origin A. In an example, the system is controllable to allow the user to indicate any angle within the range of 0° to at least about 180° about point C. In another example, the system is controllable to allow to the user to indicate any angle within the entire range of from 0° to 360° about point C. A measure of the degree of success of performance of the task is the measure of the delta angle ($\Delta\alpha$) between what the user indicates as the relative orientation of the point of origin (dashed arrow 744) and the actual relative orientation (dashed arrow 746) of the point of origin.

As shown in FIG. 7D, a navigation path in any example environment described herein, including in the example of any of FIGS. 8A-9U hereinbelow) may include a portion that is curved or substantially non-linear.

FIGS. 8A-9U show various perspective views of portions of computerized renderings of an environment during various non-limiting example navigation tasks according to the principles herein. In these examples, the computing device is configured to present differing perspective views of a selected portion of an environment that the individual is required to navigate, but from the perspective of the user indicator (such as but not limited to and avatar or other guidable element). The example perspective views are illustrative of navigation through an example environment and are not to be limiting on the scope of the instant disclosure. The example images depict the type of sequence of perspective views that a user can encounter as the user navigates through the environment.

Figure 8A:
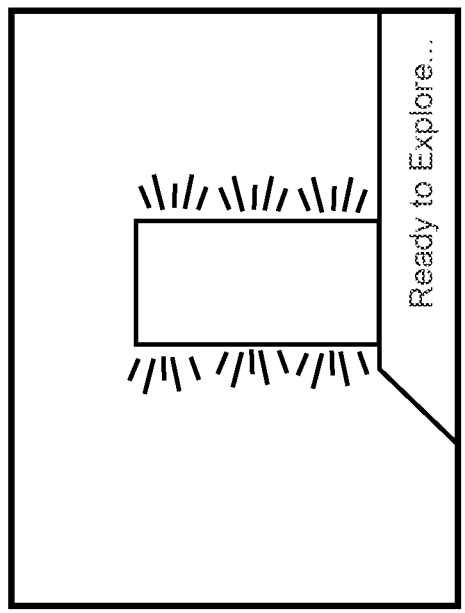
FIGS. 8A-8C show a computerized rendering of an entrance to an environment of a non-limiting example navigation task, according to the principles herein.
Figure 8B:
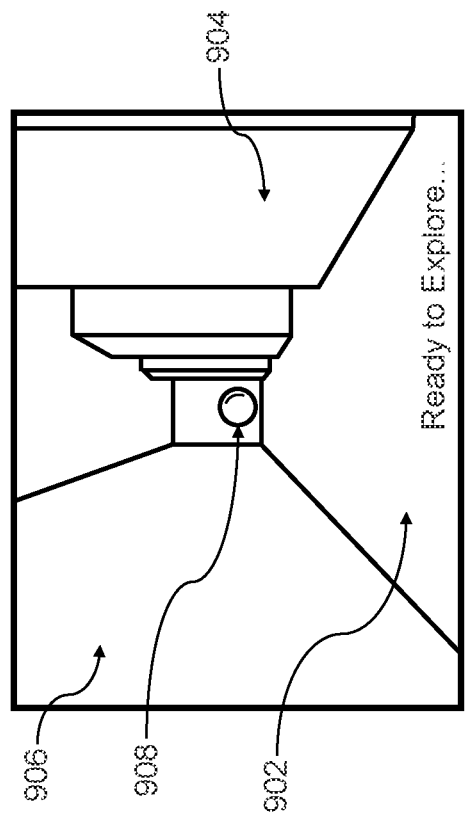
Figure 8C:
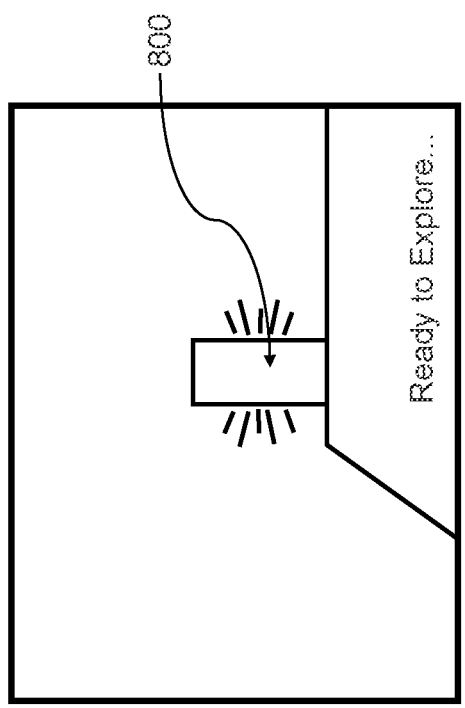

FIGS. 8A-8C show differing perspective views of an example entryway 800 (here depicted as a lit opening) as the user actuates the controls of the computing device to pass through the entryway to enter the environment. FIGS. 8A-8C also show examples of the types of heads-up display (HUD) 802 that the computing device can be used to display to a user as they navigate the environment. In this example, the computing device prompts the user with the display of the instructions "READY TO EXPLORE" as the HUD 802.

Figure 9A:
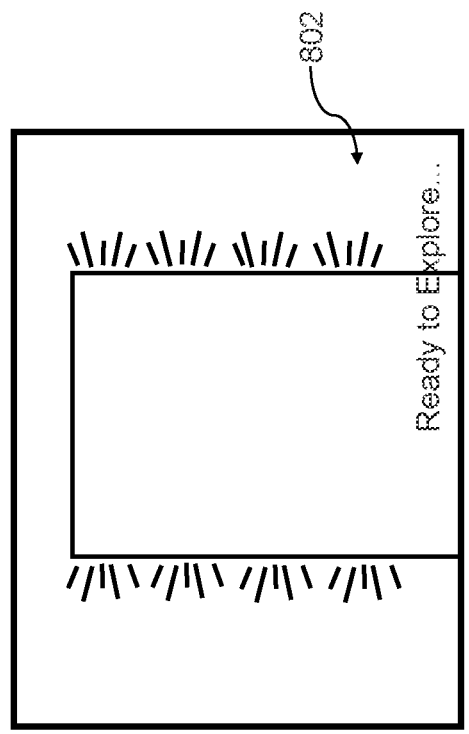
FIGS. 9A-9U show views of portions of a computerized rendering of an environment of a non-limiting example navigation task, according to the principles herein.
Figure 9C:
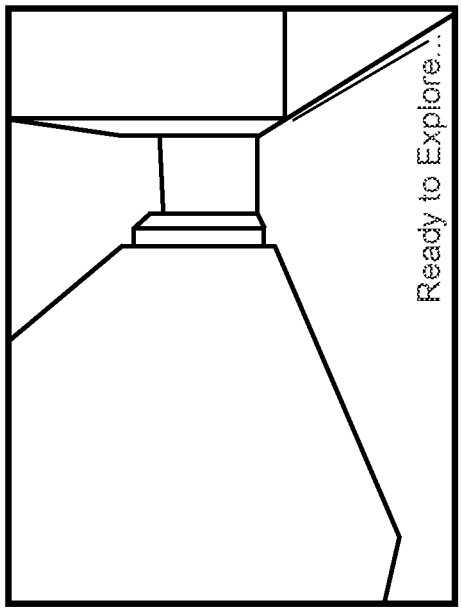
Figure 9E:
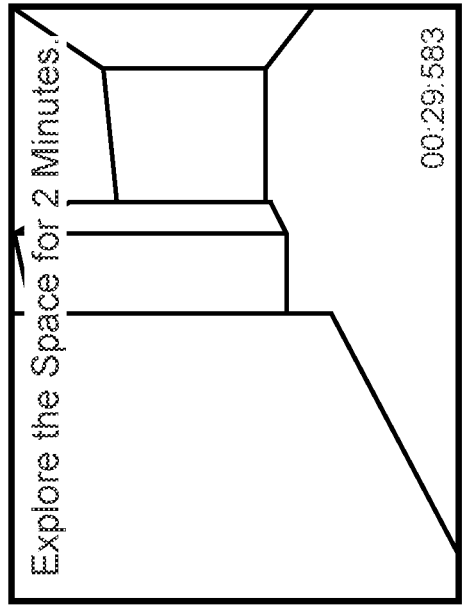
Figure 9B:
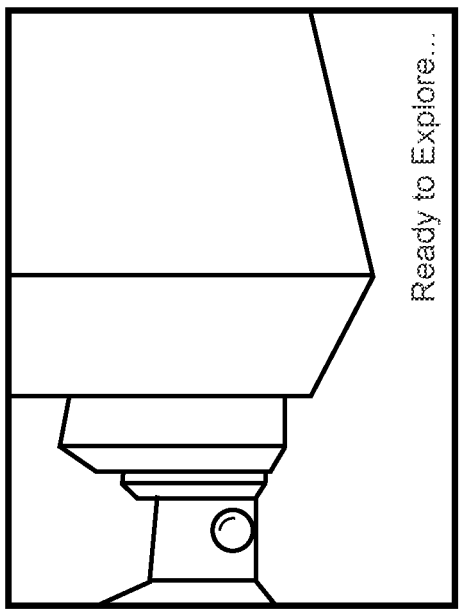
Figure 9D:
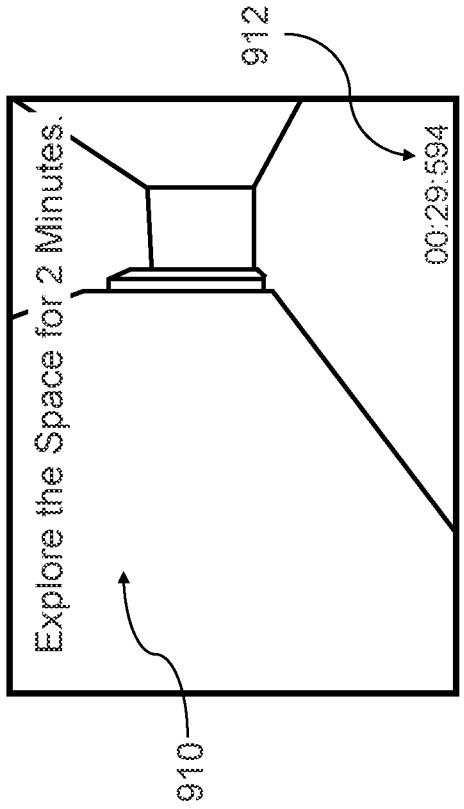
Figure 9F:
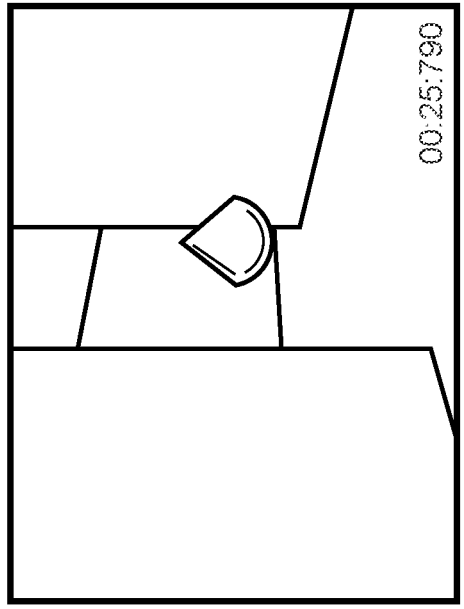
Figure 9G:
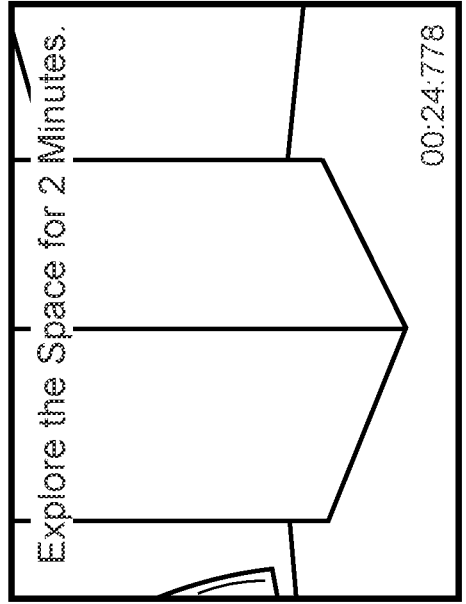
Figure 9H:
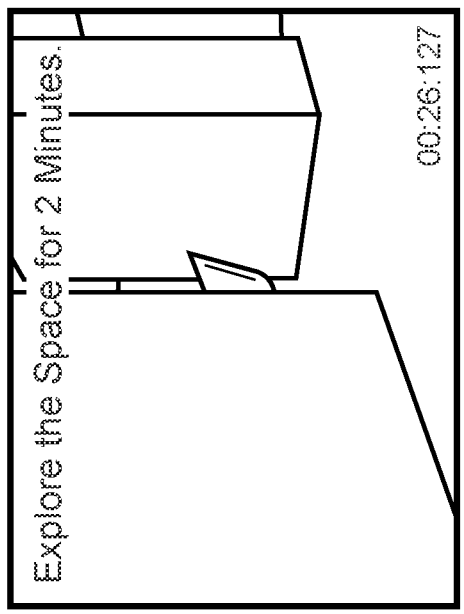
Figure 9I:
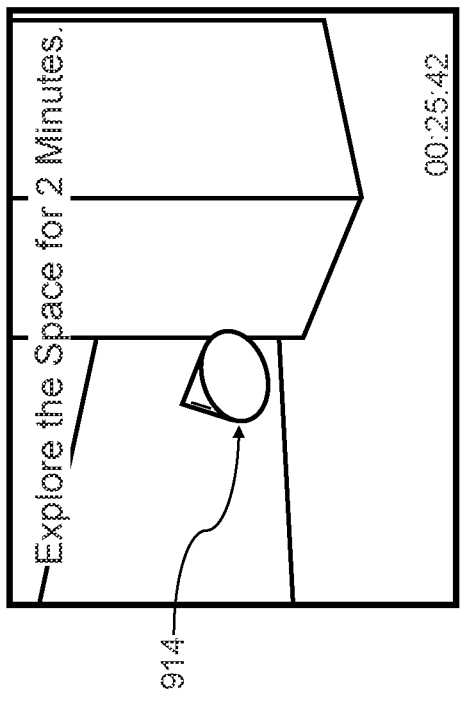
Figure 9K:
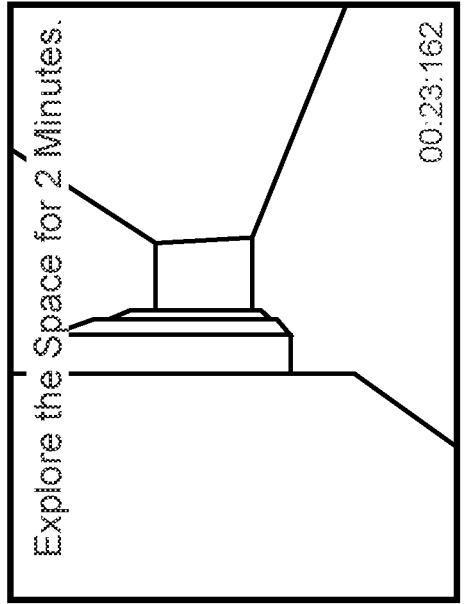
Figure 9M:
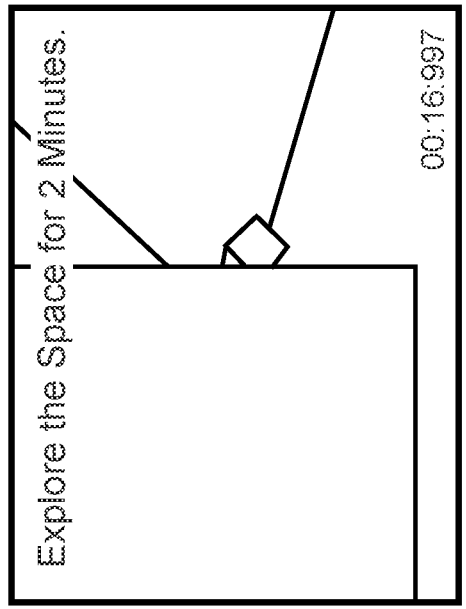
Figure 9J:
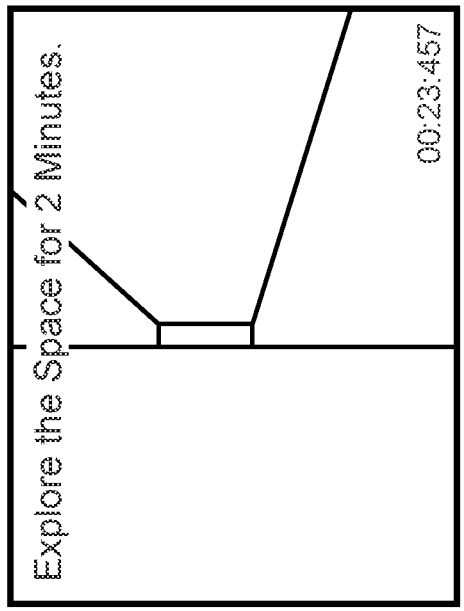
Figure 9L:
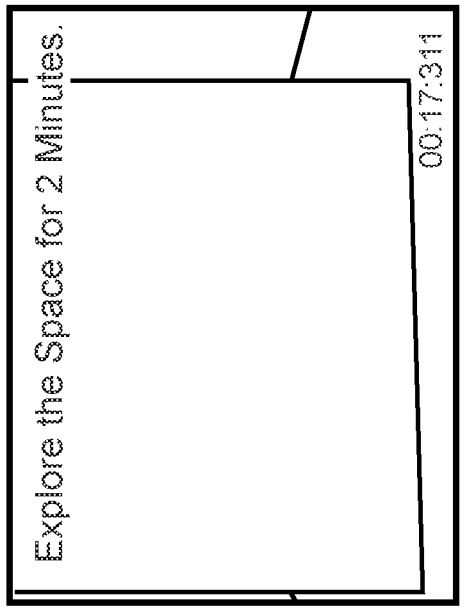
Figure 9N:
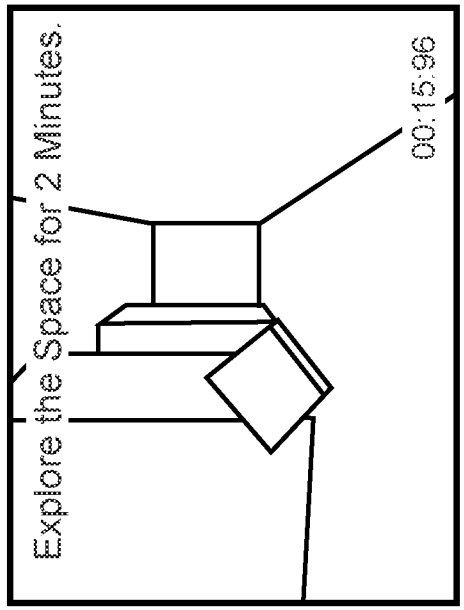
Figure 9O:
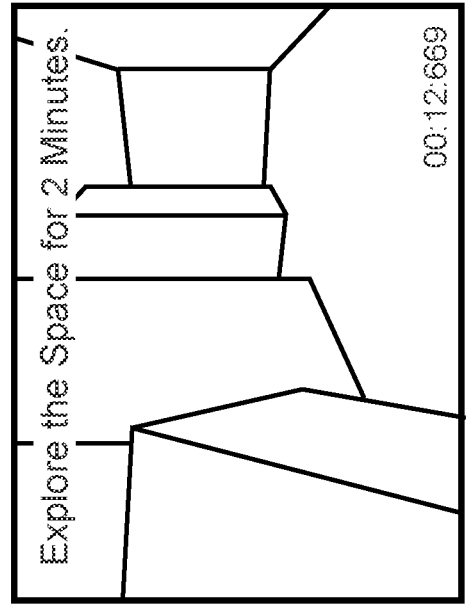
Figure 9P:
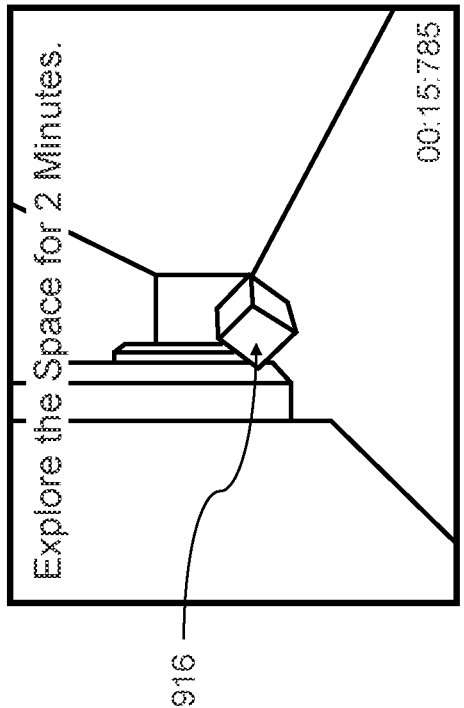
Figure 9Q:
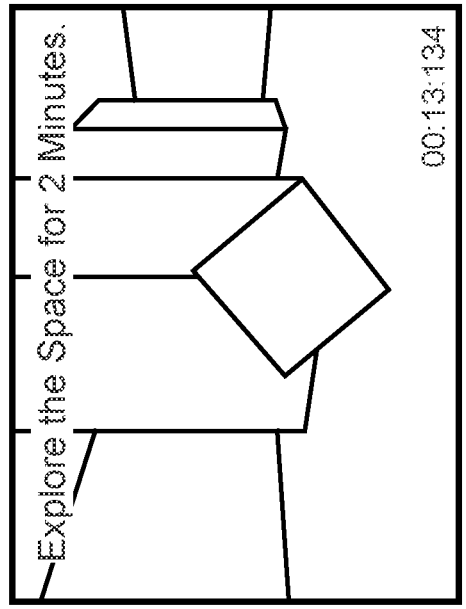
Figure 9S:
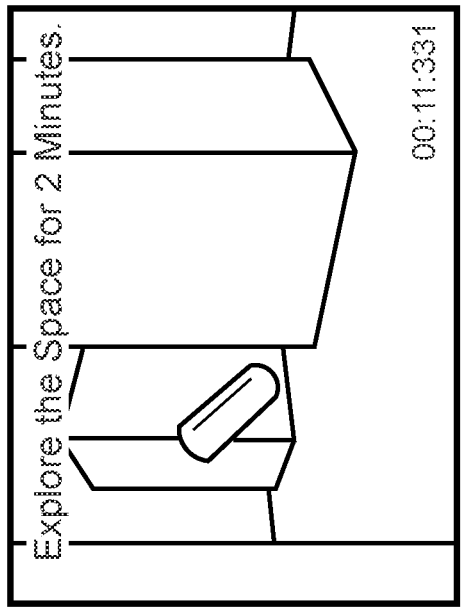
Figure 9U:
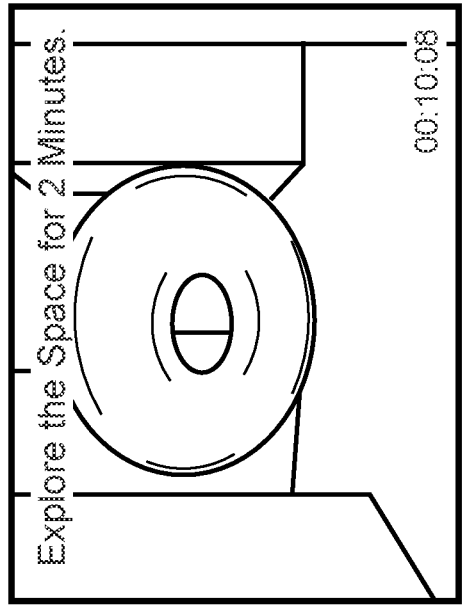
Figure 9R:
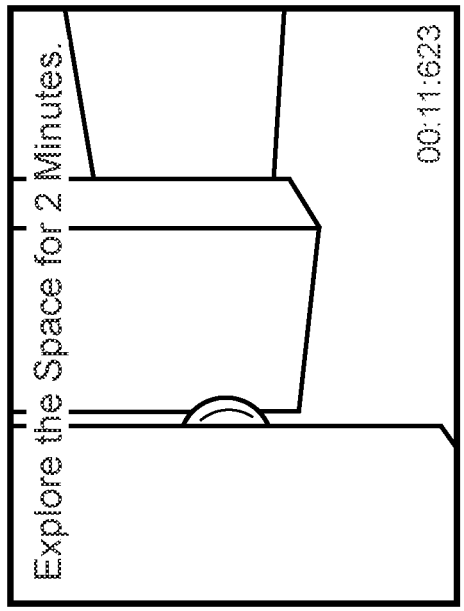
Figure 9T:
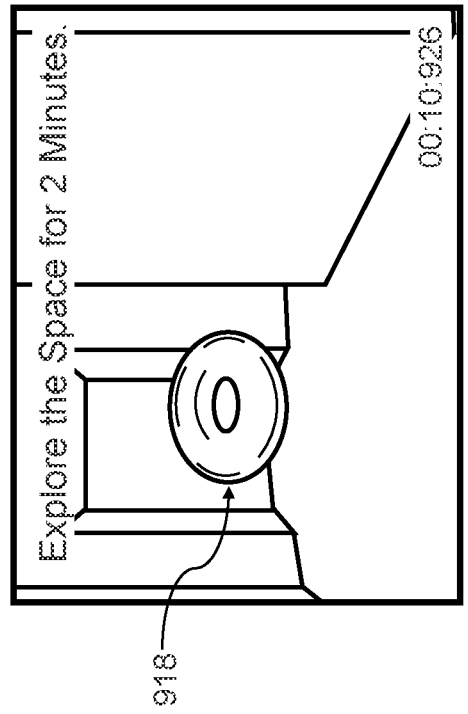

FIGS. 9A-9U show non-limiting examples of a series of perspective views of an environment as the computing device allows a user to conduct an exploration to gain some familiarity with the environment. In the example of FIG. 9A, portions of the example course 902 are defined by obstacles 904, and a wall 906 and are configured to allow traversal of the user indicator (such as but not limited to an avatar or other guidable element), as the user explores the environment. Also shown is an example of a target shaped object 908 (in this example, a sphere) that the user may be instructed to locate in one or more testing sessions. FIGS. 9B and 9C show examples of the perspective views rendered as the user actuates the computing device controls to turn and move around in the environment. FIGS. 9D-9U show the perspective views of the environment as the user moves forward, moves backwards, and turns around obstacles in the environment. FIGS. 9D-9U also show the non-limiting example HUD 910 display rendered to the user by the computing device to indicate that it is an exploration phase and the amount of time the user is allowed for the exploration (whether a guided route or a free-exploration), as well as a HUD 912 that indicates the time spent as the user navigates through the exploration phase. FIGS. 9D-9U show the other non-limiting example shaped objects located about the environment, including a cone 914, a cube 916, and a doughnut 918.

In a non-limiting example, an individual may be presented with a perspective view such as shown in FIGS. 9A-9U, with verbal or visual instructions indicating that they have been placed at an unknown location within a previously-experienced virtual environment (through the exploration phase), and instructed to perform a navigation task from this unknown location. As an example of such a navigation task, an individual may be required to use the computing device controls to look around, determine their current location to the best of their ability, and point to a previously navigated (and presumed-known) location within the environment. Performance metrics for such a task would include the accuracy of the directional response, and the time required to generate this response. As another example of such a navigation task, an individual may be required to move their avatar from the unknown location to a presumed-known location within the environment. Performance metrics for such a task could include the time required to reach the goal location, and differences between the path used to reach the goal location and one or more optimal paths (e.g., optimal paths determined using mathematical or algorithmic computational or modeling methods).

As shown in FIGS. 9A-9U, the relative dimensions the passageway, obstacles, and environment walls are configured such that that $\alpha_3 > \alpha_2 > \alpha_1$ (as described in connection with FIG. 7C) and such that a user presented with the perspective view is obstructed from observing the contents of adjacent passageways until the user is within a certain distance of a cross-channel or a turn. As a non-limiting example, dimensions $\alpha_3:\alpha_2:\alpha_1$ can be related in a ratio of 10:2:1.

Emotional Processing

As described herein, using the example systems, methods, and apparatus herein can be implemented to adapt the tasks and/or interference (at least one including an evocative element) from one user session to another (or even from one user trial to another) to enhance the cognitive skills of an individual under emotional load based on the science of brain plasticity. Adaptivity is a beneficial design element for any effective plasticity-harnessing tool. In example systems, methods, and apparatus, the processing unit is configured to control parameters of the tasks and/or interference, such as but not limited to the timing, positioning, and nature of the stimuli, so that the physical actions of the individual can be recorded during the interaction(s). As described hereinabove, the individual's physical actions are affected by their neural activity during the interactions with the computing device to perform single-tasking and multi-tasking tasks. The science of interference processing shows (based on the results from physiological and behavioral measurements) that the aspect of adaptivity can result in changes in the brain of an individual in response to the training from multiple sessions (or trials) based on neuroplasticity, thereby enhancing the cognitive skills of the individual. The example systems, methods, and apparatus are configured to implement tasks and/or interference with at least one evocative element, where the individual performs the interference processing under emotional load. As supported in the published research results described hereinabove, the effect on an individual of performing tasks under emotional load can tap into novel aspects of cognitive training to enhance the cognitive abilities of the individual.

FIGS. 10A-13P show non-limiting example user interfaces that can be rendered using example systems, methods, and apparatus herein to render the tasks and/or interferences (either or both with evocative element) for user interactions. The non-limiting example user interfaces of FIGS. 10A-13P also can be used for one or more of: to display instructions to the individual for performing the tasks and/or interferences, interact with the evocative element, to collect the data indicative of the individual's responses to the tasks and/or the interferences and the evocative element, to show progress metrics, and to provide the analysis metrics.

Figure 10A:
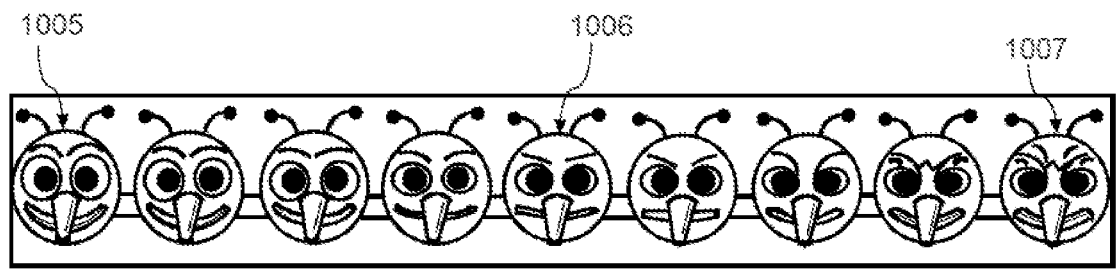
FIGS. 10A-10B show examples of the evocative elements and a user interface including instructions for user interaction, according to the principles herein.
Figure 10B:
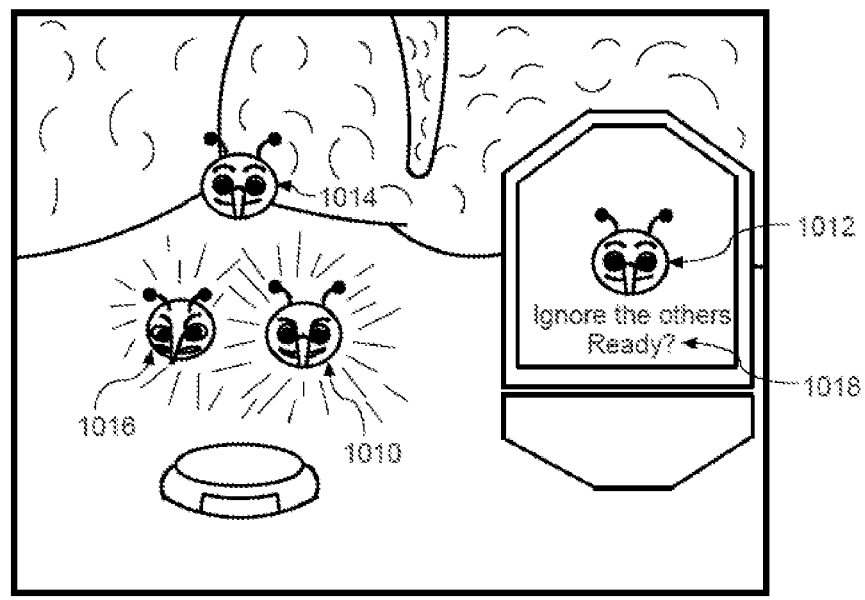

FIGS. 10A-10B show examples of the evocative elements (targets or non-targets) that can be rendered to an example user interface, according to the principles herein. FIG. 10A shows an example of the evocative elements rendered as differing types of facial expressions, including facial expressions with positive valence (happy) and facial expressions with negative valence (angry). For example, the evocative elements can be rendered as a face with a happy expression 1005, a neutral expression 1006, or an angry expression 1007. FIG. 10A also shows modulations of the facial expression of the evocative element, showing differing degrees of the facial expression from the very happy face 1005 (highest degree) with gradual reduction of the degree of happiness down to the neutral face 1006, and also showing differing degrees of the facial expression from the very angry face 1007 (highest degree) with gradual reduction of the degree of anger down to the neutral face 1006, with each potentially evoking differing levels of emotional response in an individual. FIG. 10B shows an example user interface with evocative elements rendered as differing types of facial expressions (happy 1010, neutral 1014, angry 1016). FIG. 10B also shows an example display feature 1018 for displaying instructions to the individual for performing the tasks and/or interferences and to interact with the evocative element. In the non-limiting example of FIG. 10B, the display feature 1018 can be used to instruct the individual what is expected to perform a target discrimination task, with an indication of the type of response required for the evocative element (in this example, recognize and target the happy face 1012.

Figure 11A:
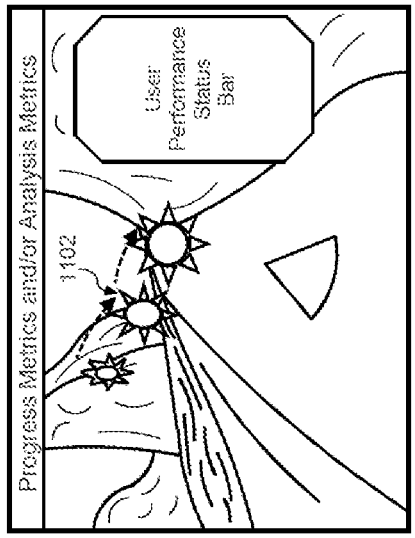
FIGS. 11A-11D show examples of the time-varying features of example objects (targets or non-targets) that can be rendered to an example user interface, according to the principles herein.
Figure 11B:
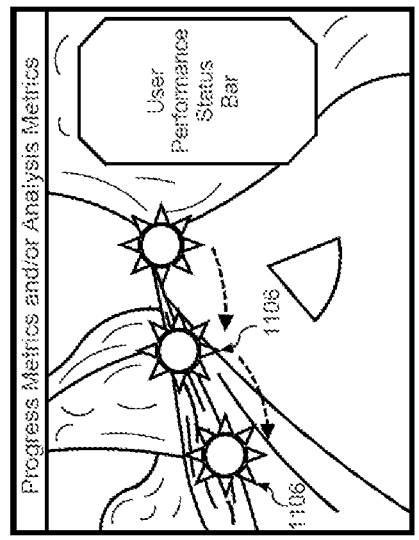
Figure 11C:
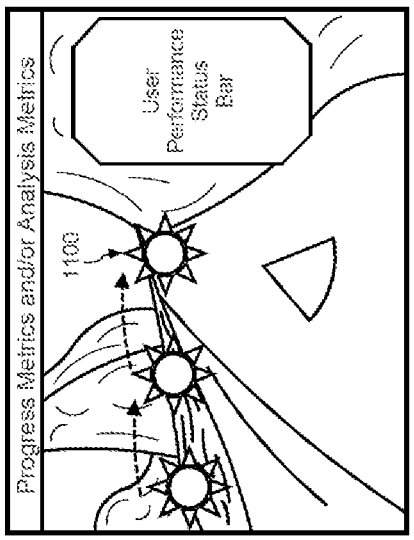
Figure 11D:
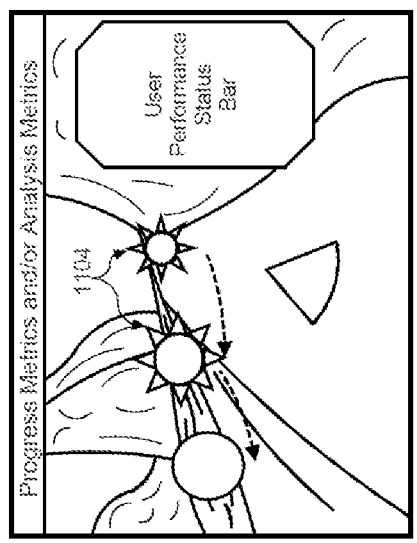

FIGS. 11A-11D show examples of the features of object(s) (targets or non-targets) that can be rendered as time-varying characteristics to an example user interface, according to the principles herein. FIG. 11A shows an example where the modification to the time-varying characteristics of an aspect of the object 1100 rendered to the user interface is a dynamic change in position and/or speed of the object 1100 relative to environment rendered in the graphical user interface. FIG. 11B shows an example where the modification to the time-varying characteristics of an aspect of the object 1102 rendered to the user interface is a dynamic change in size and/or direction of trajectory/motion, and/or orientation of the object 1102 relative to the environment rendered in the graphical user interface. FIG. 11C shows an example where the modification to the time-varying characteristics of an aspect of the object 1104 rendered to the user interface is a dynamic change in shape or other type of the object 1104 relative to the environment rendered in the graphical user interface. In this non-limiting example, the time-varying characteristic of object 1104 is effected using morphing from a first type of object (a star object) to a second type of object (a round object). In another non-limiting example, the time-varying characteristic of object 1104 is effected by rendering a blendshape as a proportionate combination of a first type of object and a second type of object. FIG. 11C shows an example where the modification to the time-varying characteristics of an aspect of the object 1104 rendered to the user interface is a dynamic change in shape or other type of the object 1104 rendered in the graphical user interface (in this non-limiting example, from a star object to a round object). FIG. 11D shows an example where the modification to the time-varying characteristics of an aspect of the object 1106 rendered to the user interface is a dynamic change in pattern, or color, or visual feature of the object 1106 relative to environment rendered in the graphical user interface (in this non-limiting example, from a star object having a first pattern to a round object having a second pattern). In another non-limiting example, the time-varying characteristic of object can be a rate of change of a facial expression depicted on or relative to the object. In any example herein, the foregoing time-varying characteristic can be applied to an object including the evocative element to modify an emotional load of the individual's interaction with the apparatus (e.g., computing device or cognitive platform).

Figure 12A:
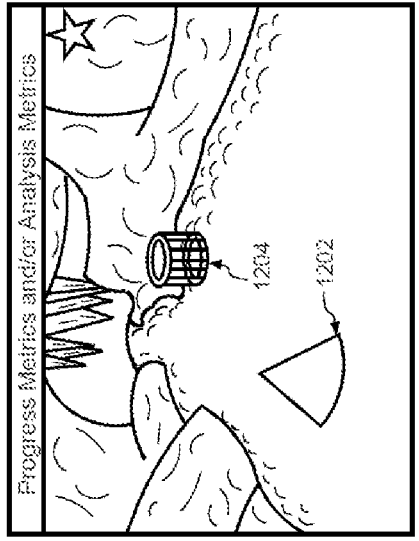
FIGS. 12A-12T show a non-limiting example of the dynamics of tasks and interferences that can be rendered at user interfaces, according to the principles herein.
Figure 12B:
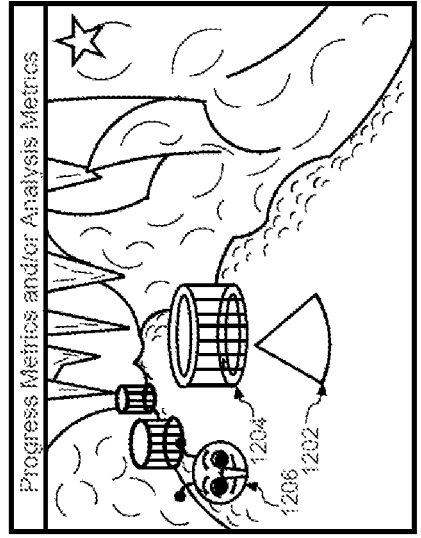
Figure 12C:
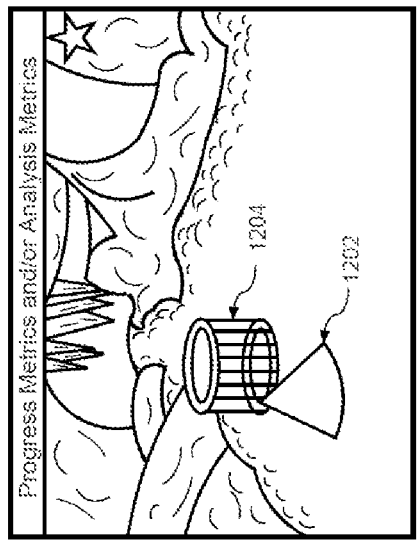
Figure 12D:
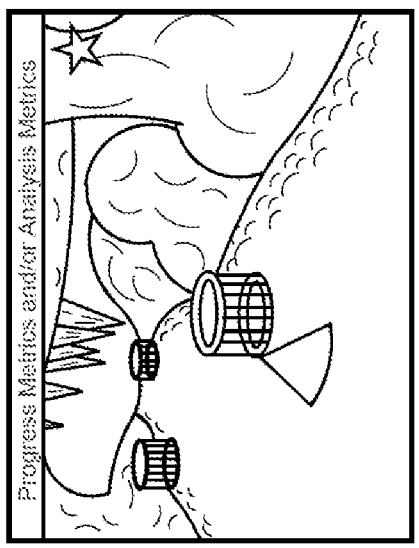
Figure 12E:
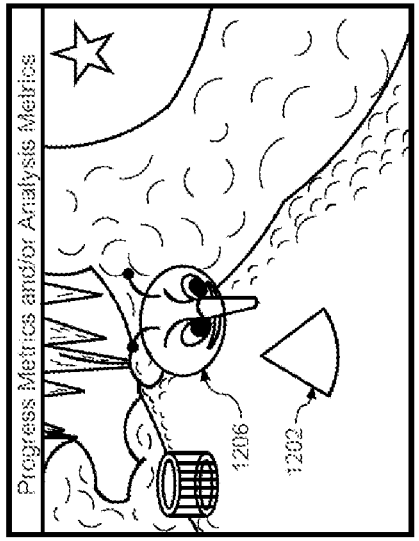
Figure 12F:
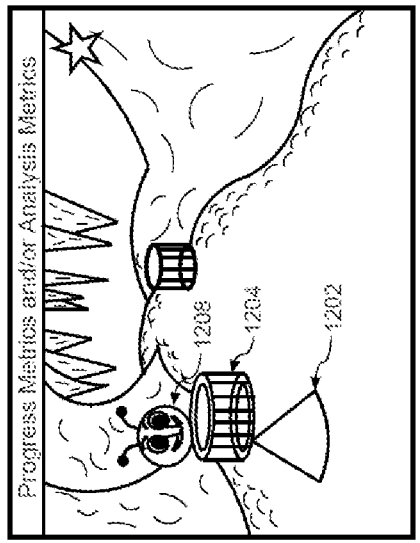
Figure 12G:
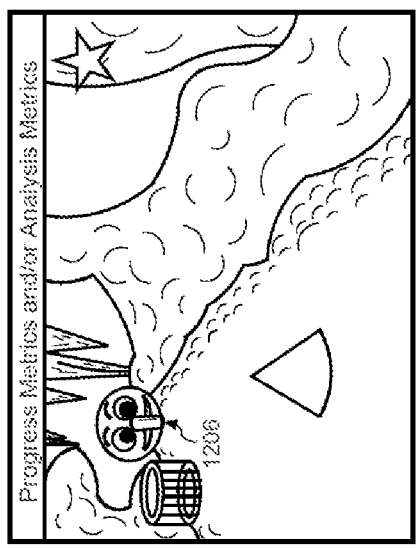
Figure 12H:
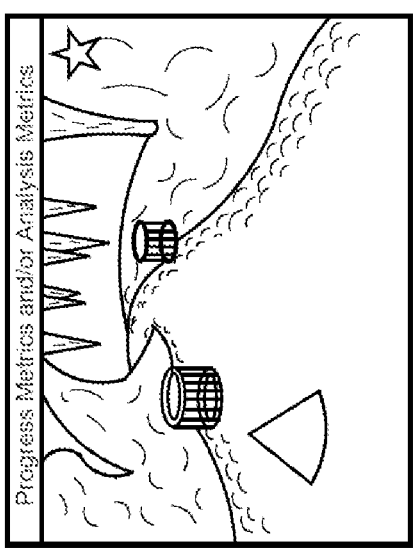
Figure 12I:
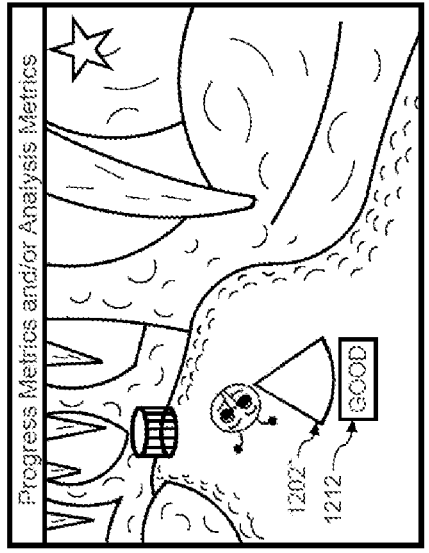
Figure 12J:
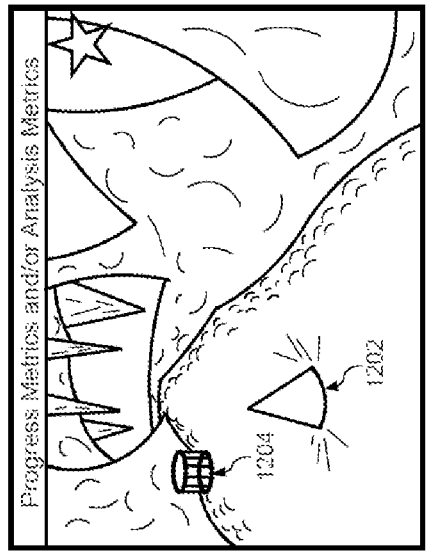
Figure 12K:
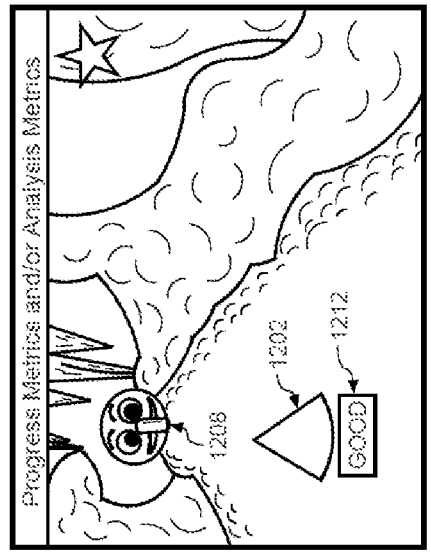
Figure 12L:
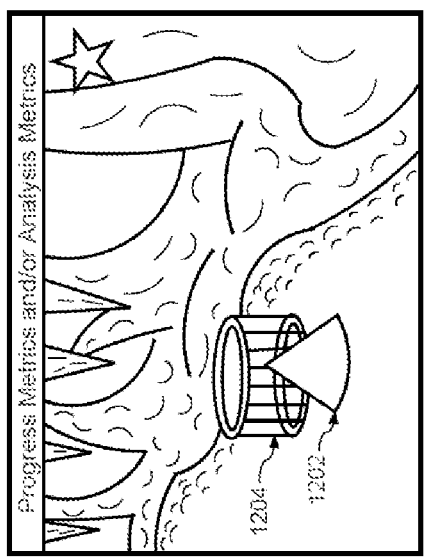
Figure 12M:
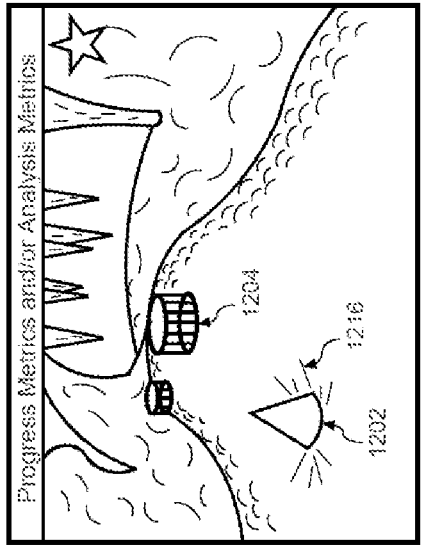
Figure 12N:
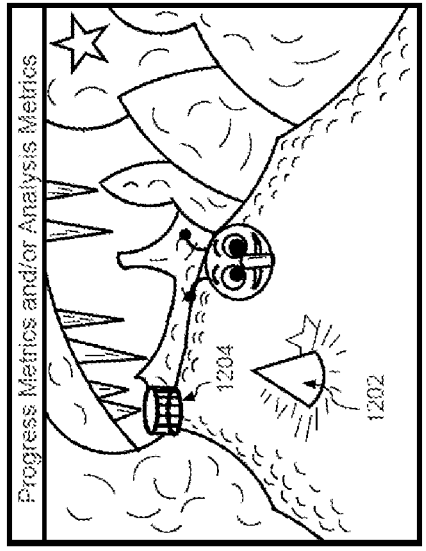
Figure 12O:
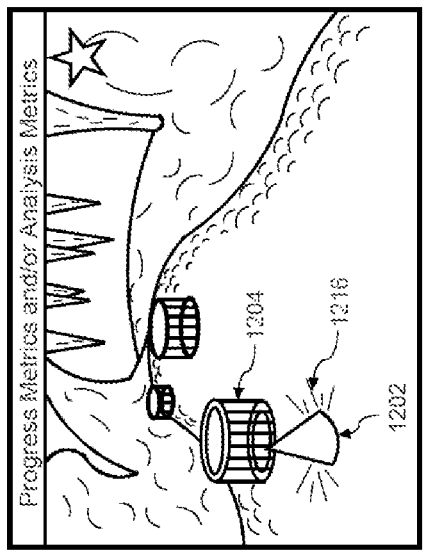
Figure 12P:
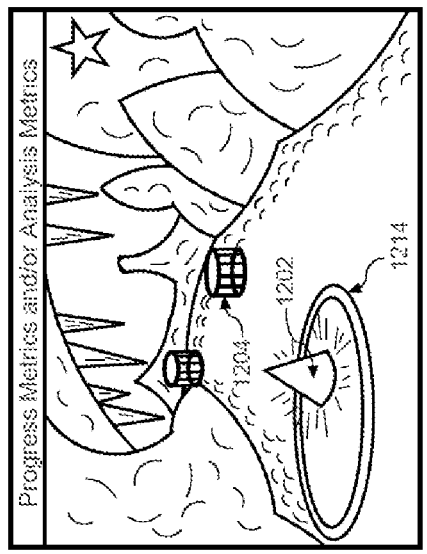
Figure 12Q:
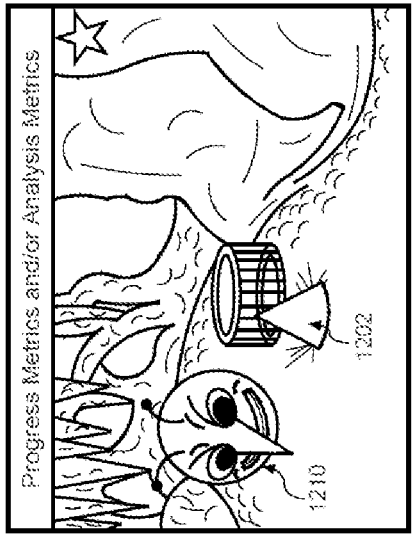
Figure 12R:
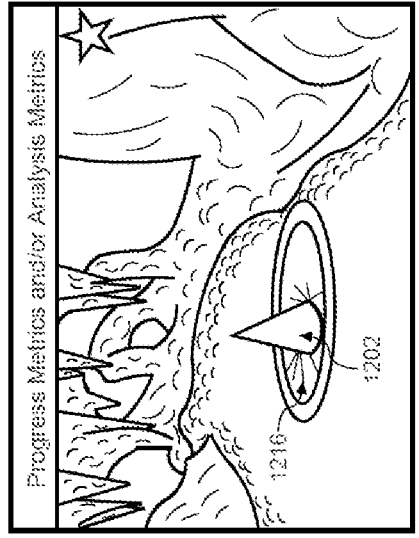
Figure 12S:
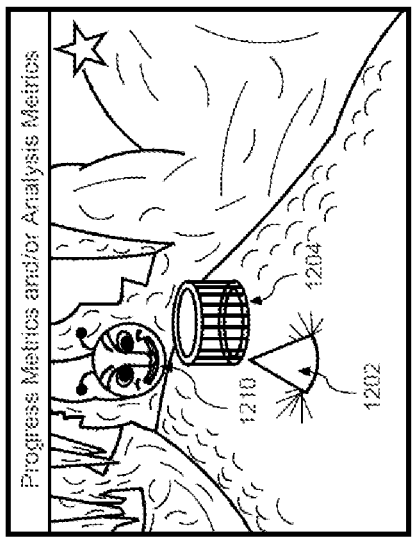
Figure 12T:
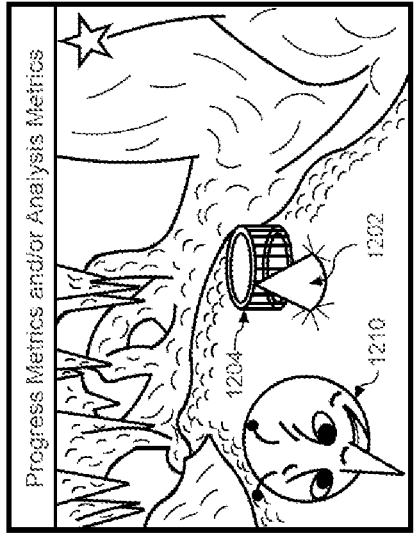

FIGS. 12A-12T show a non-limiting example of the dynamics of tasks and interferences that can be rendered at user interfaces, according to the principles herein. In this example, the task is a visuo-motor navigation task, and the interference is target discrimination (as a secondary task). The evocative element is rendered faces with differing facial expressions, and the evocative element is a part of the interference. The example system is programmed to instruct the individual to perform the visuo-motor task and target discrimination (with identification of a specific facial expression as the response to the evocative element). As shown in FIGS. 12A-12T, the individual is required to perform the navigation task by controlling the motion of the avatar 1202 along a path that coincides with the milestone objects 1204. FIGS. 12A-12T show a non-limiting example implementation where the individual is expected to actuate an apparatus or computing device (or other sensing device) to cause the avatar 1202 to coincide with the milestone object 1204 as the response in the navigation task, with scoring based on the success of the individual at crossing paths with (e.g., hitting) the milestone objects 804. In another example, the individual is expected to actuate an apparatus or computing device (or other sensing device) to cause the avatar 1202 to miss the milestone object 1204, with scoring based on the success of the individual at avoiding the milestone objects 1204. FIGS. 12A-12T also show the dynamics of a non-target object 1206 having an first type of evocative element (a neutral facial expression), where the time-varying characteristic is the trajectory of motion of the object. FIGS. 12A-12T also show the dynamics of a target object 1208 having a second type of evocative element (a happy facial expression), where the time-varying characteristic is the trajectory of motion of the object. FIGS. 12A-12T also show the dynamics of another non-target object 1210 having a third type of evocative element (an angry facial expression), where the time-varying characteristic is the trajectory of motion of the object.

In the example of FIGS. 12A-12T, the processing unit of the example system, method, and apparatus is configured to receive data indicative of the individual's physical actions to cause the avatar 1202 to navigate the path. For example, the individual may be required to perform physical actions to "steer" the avatar, e.g., by changing the rotational orientation or otherwise moving a computing device. Such action can cause a gyroscope or accelerometer or other motion or position sensor device to detect the movement, thereby providing measurement data indicative of the individual's degree of success in performing the navigation task.

In the example of FIGS. 12A-12T, the processing unit of the example system, method, and apparatus is configured to receive data indicative of the individual's physical actions to perform the target discrimination and to identify a specified evocative element (i.e., a specified facial expression). For example, the individual may be instructed prior to a trial or other session to tap, or make other physical indication, in response to display of a target object having the specified evocative element 1208, and not to tap to make the physical indication in response to display of a non-target object 1206 or 1210 (based on the type of the evocative element). In FIGS. 12A-12C and 12E-12H, the target discrimination acts as an interference (i.e., a secondary task) to the primary navigation task, in an interference processing multi-tasking implementation. As described hereinabove, the example systems, methods, and apparatus can cause the processing unit to render a display feature (e.g., display feature 500 in FIGS. 4A-4D) to display the instructions to the individual as to the expected performance (i.e., which evocative element to respond to, and how to perform the target discrimination and navigation tasks). As also described hereinabove, the processing unit of the example system, method, and apparatus can be configured to (i) receive the data indicative of the measure of the degree and type of the individual's response to the primary task substantially simultaneously as the data indicative of the measure of the individual's response to the evocative element is collected (for a specified evocative element), or (i) to selectively receive data indicative of the measure of the individual's response to the specified evocative element as a target stimulus (i.e., an interruptor) substantially simultaneously (i.e., at substantially the same time) as the data indicative of the measure of the degree and type of the individual's response to the task is collected and to selectively not collect the measure of the individual's response to the non-specified evocative element a non-target stimulus (i.e., a distraction) substantially simultaneously (i.e., at substantially the same time) as the data indicative of the measure of the degree and type of the individual's response to the task is collected.

In FIGS. 12A-12T, a feature 812 including the word "GOOD" is rendered near the avatar 1202 to signal to the individual that analysis of the data indicative of the individual's responses to the navigation task and target discrimination interference including the evocative element indicate satisfactory performance. The figures show an example of a change in the type of rewards presented to the individual as another indication of satisfactory performance, including at least one modification to the avatar 1202 to symbolize excitement, such as but not limited to the rings 1214 or other active element and/or showing jet booster elements 1216 that become star-shaped (and reward graphics such as but not limited to the "STAR-ZONE" graphic). Many other types of reward elements can be used, and the rate and type of reward elements displayed can be changed and modulated as a time-varying element.

Figure 13A:
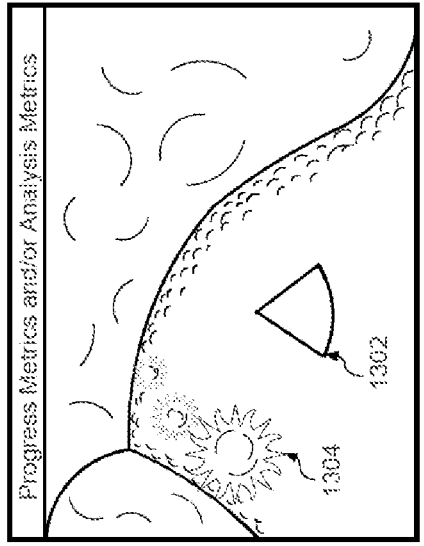
FIGS. 13A-13P show a non-limiting example of the dynamics of tasks and interferences that can be rendered at user interfaces, according to the principles herein.
Figure 13B:
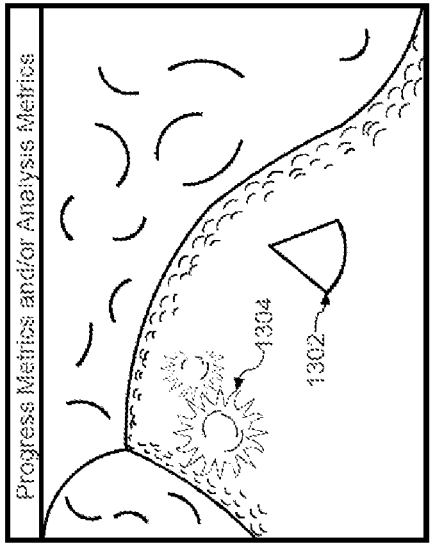
Figure 13C:
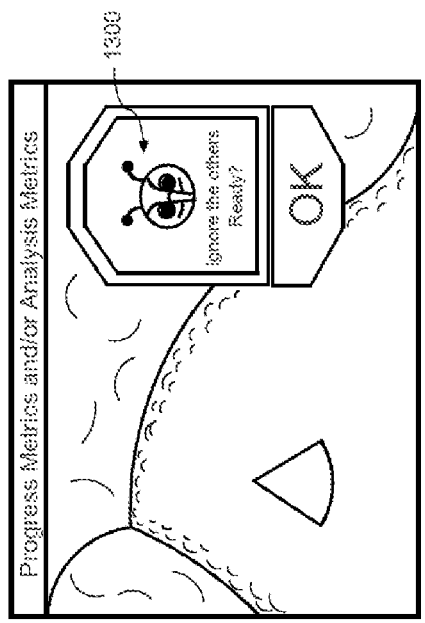
Figure 13D:
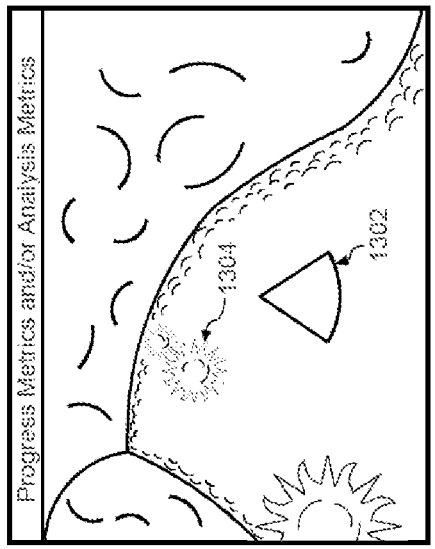
Figure 13F:
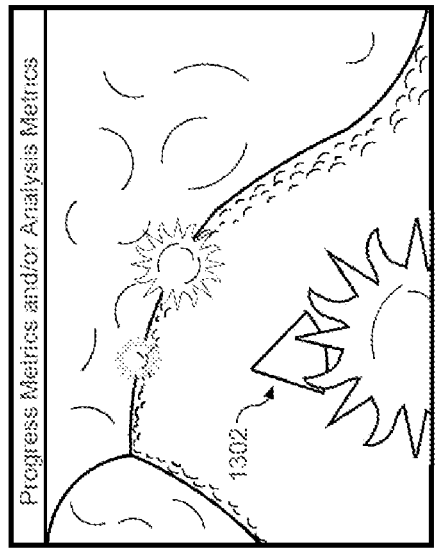
Figure 13H:
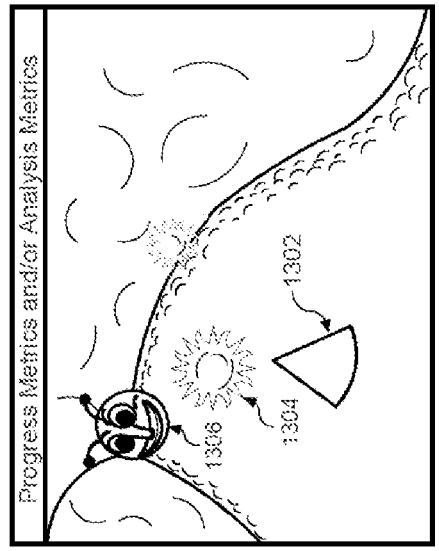
Figure 13E:
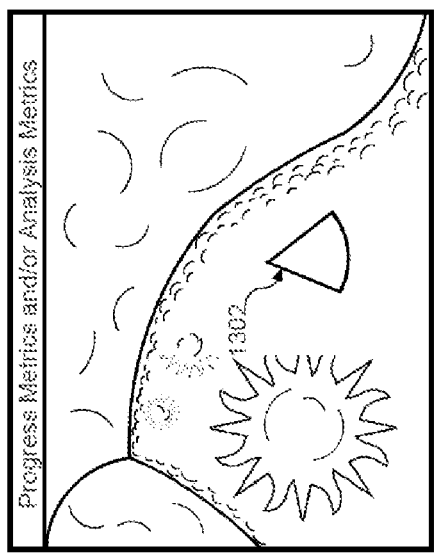
Figure 13G:
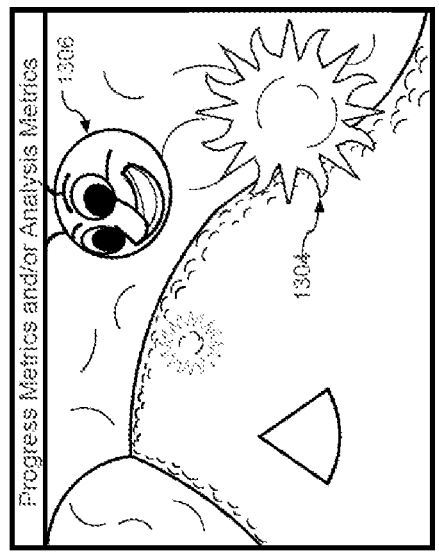
Figure 13J:
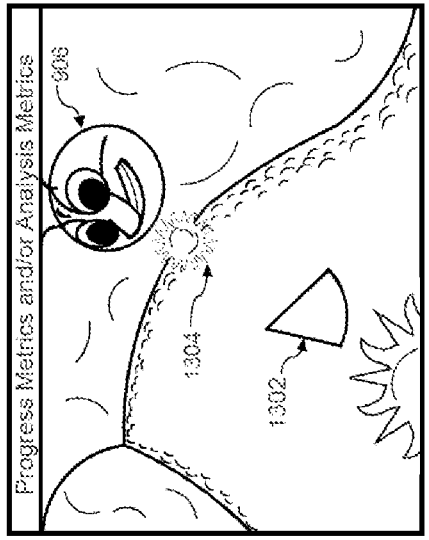
Figure 13L:
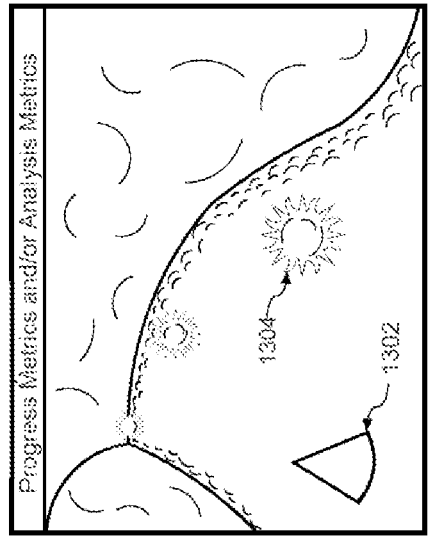
Figure 13I:
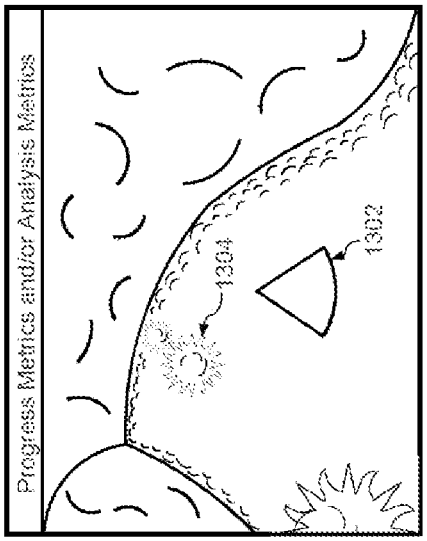
Figure 13K:
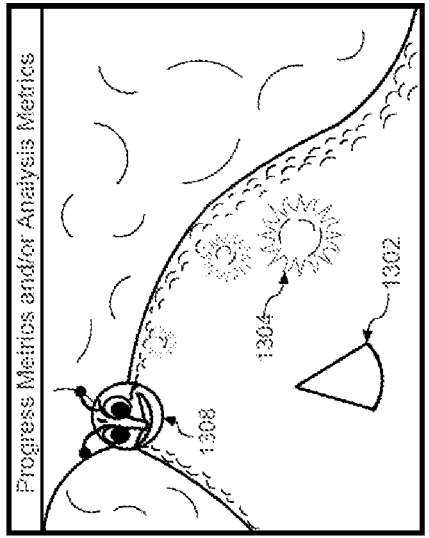
Figure 13M:
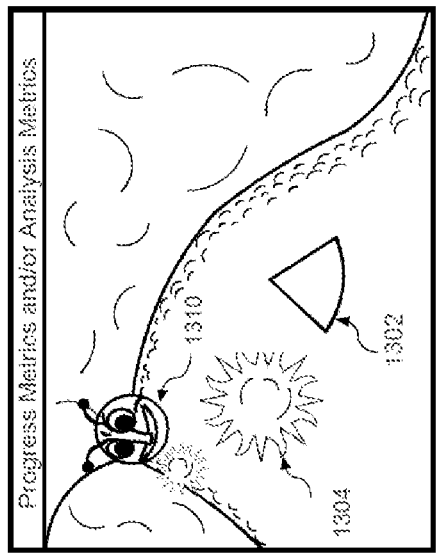
Figure 13N:
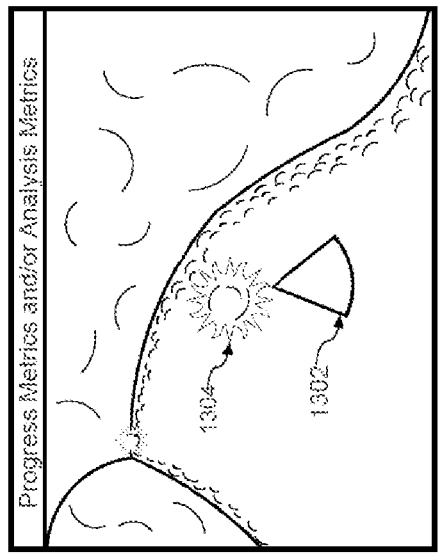
Figure 13O:
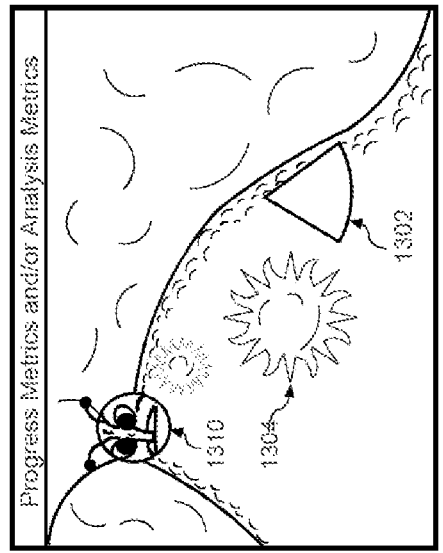
Figure 13P:
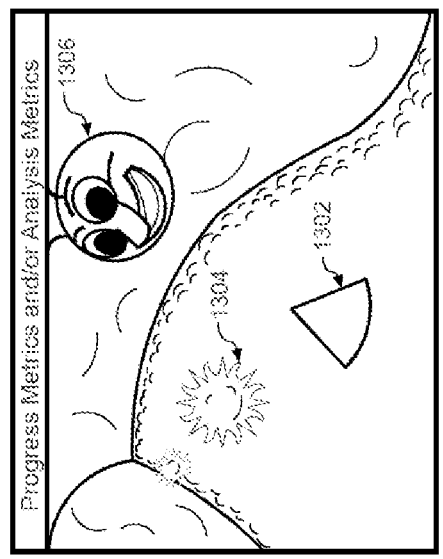

FIGS. 13A-13P show a non-limiting example of the dynamics of tasks and interferences that can be rendered at user interfaces, according to the principles herein. In this example, the task is a visuo-motor navigation task, and the interference is target discrimination (as a secondary task).

The evocative element is rendered faces with differing facial expressions, and the evocative element is a part of the interference. FIG. 13A shows an example display feature 1300 that can be rendered to instruct the individual to perform the visuo-motor task and target discrimination (with identification of a specific facial expression as the response to the evocative element). As shown in FIGS. 13A-13P, the individual is required to perform the navigation task by controlling the motion of the avatar 1302 along a path that avoids (i.e., does not coincides with) the milestone objects 1304. FIGS. 13A-13P show a non-limiting example implementation where the individual is expected to actuate an apparatus or computing device (or other sensing device) to cause the avatar 1302 to avoid the milestone object 1304 as the response in the navigation task, with scoring based on the success of the individual at not crossing paths with (e.g., not hitting) the milestone objects 1304. FIGS. 13A-13P also show the dynamics of a non-target object 1306 having a first type of evocative element (a happy facial expression), where the time-varying characteristic is the trajectory of motion of the object. FIGS. 13A-13P also show the dynamics of a target object 1308 having a second type of evocative element (an angry facial expression), where the time-varying characteristic is the trajectory of motion of the object. FIGS. 13A-13P also show the dynamics of another non-target object 1310 having a third type of evocative element (an angry facial expression), where the time-varying characteristic is the trajectory of motion of the object.

In the example of FIGS. 13A-13P, the processing unit of the example system, method, and apparatus is configured to receive data indicative of the individual's physical actions to cause the avatar 1302 to navigate the path. For example, the individual may be required to perform physical actions to "steer" the avatar, e.g., by changing the rotational orientation or otherwise moving a computing device. Such action can cause a gyroscope or accelerometer or other motion or position sensor device to detect the movement, thereby providing measurement data indicative of the individual's degree of success in performing the navigation task.

In the example of FIGS. 13A-13P, the processing unit of the example system, method, and apparatus is configured to receive data indicative of the individual's physical actions to perform the target discrimination and to identify a specified evocative element (i.e., a specified facial expression). For example, the individual may be instructed using display feature 1300 prior to a trial or other session to tap, or make other physical indication, in response to display of a target object having the specified evocative element 1308, and not to tap to make the physical indication in response to display of a non-target object 1306 or 1310 (based on the type of the evocative element). In FIGS. 13A-13P, the target discrimination acts as an interference (i.e., a secondary task) to the primary navigation task, in an interference processing multitasking implementation. As described hereinabove, the example systems, methods, and apparatus can cause the processing unit to render a display feature (e.g., display feature 500 in FIGS. 4A-4D) to display the instructions to the individual as to the expected performance (i.e., which evocative element to respond to, and how to perform the target discrimination and navigation tasks). As also described hereinabove, the processing unit of the example system, method, and apparatus can be configured to (i) receive the data indicative of the measure of the degree and type of the individual's response to the primary task substantially simultaneously as the data indicative of the measure of the individual's response to the evocative element is collected (for a specified evocative element), or (i) to selectively receive data indicative of the measure of the individual's response to the specified evocative element as a target stimulus (i.e., an interruptor) substantially simultaneously (i.e., at substantially the same time) as the data indicative of the measure of the degree and type of the individual's response to the task is collected and to selectively not collect the measure of the individual's response to the non-specified evocative element a non-target stimulus (i.e., a distraction) substantially simultaneously (i.e., at substantially the same time) as the data indicative of the measure of the degree and type of the individual's response to the task is collected.

In various examples, the degree of non-linearity of the accumulation of belief for an individual's decision making (i.e., as to whether to execute a response) can be modulated based on adjusting the time-varying characteristics of the task and/or interference. As a non-limiting example, where the time-varying characteristic is a trajectory, speed, orientation, or size of the object (target or non-target), the amount of information available to an individual to develop a belief (in order to make decision as to whether to execute a response) can be made smaller initially, e.g., where the object caused to be more difficult to discriminate by being rendered as farther away or smaller, and can be made to increase at differing rates (nonlinearly) depending on how quickly more information is made available to the individual to develop belief (e.g., as the object is rendered to appear to get larger, change orientation, move slower, or move closer in the environment). Other non-limiting example time-varying characteristics of the task and/or interference that can be adjusted to modulate the degree of non-linearity of the accumulation of belief include one or more of a rate of change of a facial expression, at least one color of an object, the type of the object, a rate of morphing of a first type of object to change to a second type of object, and a blendshape of evocative elements (e.g., a blendshape of facial expressions).

The data indicative of the individual's response to the task and the response of the individual to the at least one evocative element is used to compute at least one performance metric comprising at least one quantified indicator of cognitive abilities of the individual under emotional load. In a non-limiting example, the performance metric can include the computed interference cost under emotional load.

The difficulty levels (including the difficulty of the task and/or interference, and of the evocative element) of a subsequent session can be set based on the performance metric computed for the individual's performance from a previous session, and can be optimized to modify an individual's performance metric (e.g., to lower or optimize the interference cost under emotional load).

In a non-limiting example, the adaptation of the difficulty of a task and/or interference may be adapted with each different stimulus that is presented as an evocative element.

In another non-limiting example, the example system, method, and apparatus herein can be configured to adapt a difficulty level of a task and/or interference (including the evocative element) one or more times in fixed time intervals or in other set schedule, such as but not limited to each second, in 10 second intervals, every 30 seconds, or on frequencies of once per second, 2 times per second, or more (such as but not limited to 30 times per second).

In an example, the difficulty level of a task or interference can be adapted by changing the time-varying characteristics, such as but not limited to a speed of an object, a rate of change of a facial expression, a direction of trajectory of an object, a change of orientation of an object, at least one color of an object, a type of an object, or a size of an object, or changing a sequence or balance of presentation of a target stimulus versus a non-target stimulus.

In a non-limiting example of a visuo-motor task (a type of navigation task), one or more of navigation speed, shape of the course (changing frequency of turns, changing turning radius), and number or size of obstacles can be changed to modify the difficulty of a navigation game level, with the difficulty level increasing with increasing speed and/or increasing numbers and/or sizes of obstacles (milestone objects).

In a non-limiting example, the difficulty level of a task and/or interference of a subsequent level can also be changed in real-time as feedback, e.g., the difficulty of a subsequent level can be increased or decreased in relation to the data indicative of the performance of the task.

Figure 14:
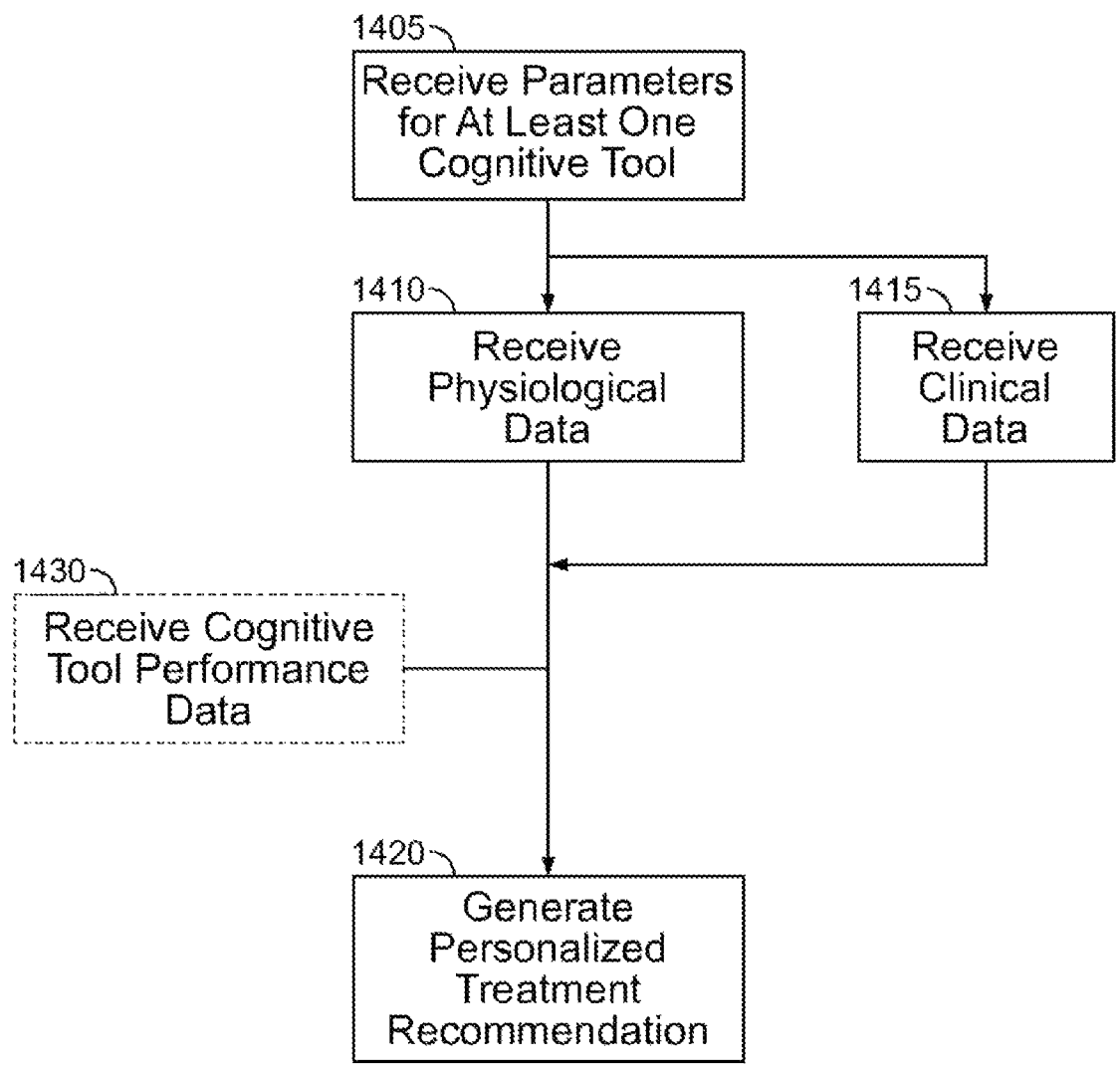
FIG. 14 is a flowchart of an exemplary method, according to the principles herein.

FIG. 14 shows a flowchart of a non-limiting exemplary computer-implemented method for generating a personalized cognitive treatment recommendation for an individual that can be implemented using one or more processors and a memory. One or more processors execute instructions stored in one or more memory storage devices comprising computer executable instructions to perform operations. In block 1405, the operation is receive parameters for at least one cognitive treatment tool. In block 1410, the operation is receive physiological data indicative of a condition of the individual. In block 1415, the operation is receive clinical data associated with the individual. In block 1420, the personalized cognitive treatment recommendation is generated based on at least one of the physiological data or the clinical data, the recommendation including a specification of (i) at least one first cognitive treatment tool, (ii) at least one second cognitive treatment tool different from the at least one first cognitive treatment tool, or (iii) both (i) and (ii). In block 1430, the operations optionally further include receive performance data indicative of the individual's performance of at least one task associated with the at least one cognitive treatment tool of the recommendation.

CONCLUSION

The above-described embodiments can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention may be embodied at least in part as a computer readable storage medium (or multiple computer readable storage media) (e.g., a computer memory, compact disks, optical disks, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A system for generating a personalized cognitive treatment for an individual, the system comprising:
    one or more processors; and
    a memory to store processor-executable instructions and communicatively coupled with the one or more processors,
    wherein upon execution of the processor-executable instructions by the one or more processors, the one or more processors are configured to:
        a) receive parameters for at least one computerized cognitive treatment tool;
        b) receive at least one of physiological data indicative of a condition of the individual, or clinical data associated with the individual;
        c) generate a personalized cognitive treatment recommendation based on at least one of the physiological data or the clinical data, the personalized cognitive treatment recommendation comprising a first specification for at least one first computerized cognitive treatment tool,
        wherein the at least one first computerized cognitive treatment tool comprises a first cognitive treatment engine configured to target a first brain region of the individual,
        wherein the at least one second computerized cognitive treatment tool comprises a second cognitive treatment engine configured to target a second brain region of the individual,
        wherein the first brain region and the second brain region are selected from the group consisting of prefrontal cortex, extended hippocampal network, amygdala-dependent network, caudate nucleus, and entorhinal cortex region,
        wherein the first brain region is different from the second brain region,
        wherein the first specification comprises a first calculated percentage of a first set of computerized stimuli or interactions to be presented in an instance of the personalized cognitive treatment and the second specification comprises a second calculated percentage of a second set of computerized stimuli or interactions to be presented in the instance of the personalized cognitive treatment,
        wherein the instance of the personalized cognitive treatment comprises a particular graphical output of the personalized cognitive treatment,
        wherein the first set of computerized stimuli or interactions comprises a first set of tasks associated with the first brain region,
        wherein the second set of computerized stimuli or interactions comprises a second set of tasks associated with the second brain region;
        d) configure the instance of the personalized cognitive treatment for the individual according to the first specification and the second specification; and
        e) present the instance of the personalized cognitive treatment to the individual at a graphical user interface of an end user device,
        wherein instance of the personalized cognitive treatment is configured to render or modify one or more graphical elements in the first set of computerized stimuli or interactions according to the first specification and render or modify one or more graphical elements in the second set of computerized stimuli or interactions according to the second specification.

2. The system of claim 1, wherein the one or more processors are further configured to: receive performance data indicative of the individual's performance of at least one first task associated with the first set of computerized stimuli or interactions presented during the instance of the personalized cognitive treatment and at least one second task associated with the second set of computerized stimuli or interactions presented during the instance of the personalized cognitive treatment.

3. The system of claim 2, further comprising: repeating steps b) and c) after the individual performs the instance of the personalized cognitive treatment, wherein data received during the repetition of step b) comprises data collected subsequent to the individual's performance of the at least one first task or the at least one second task.

4. The system of claim 3, wherein the one or more processors are further configured to: monitor a status of the condition of the individual based on an analysis of the at least one of the physiological data or the clinical data, or data indicative of an interaction of the individual with at least one cognitive monitoring tool; wherein data received during the repetition of step b) comprises data indicative of the status of the condition based on the monitoring.

5. The system of claim 1, wherein generating the personalized cognitive treatment recommendation comprises using a predictive model that is trained using a plurality of training datasets, each training dataset in the plurality of training datasets corresponding to a previously classified individual of a plurality of individuals, and each training dataset comprising data representing at least one indicator of a cognitive ability of the classified individual and data indicative of a diagnosis of a status or progression of the condition in the classified individual.

6. The system of claim 1, wherein the at least one computerized cognitive treatment tool comprises at least one of an interference processing tool, a spatial navigation tool, or an emotional processing tool.

7. The system of claim 6, wherein the personalized cognitive treatment recommendation comprises an interference processing tool and the one or more processors are further configured to:
   generate a user interface;
   present via the user interface a first instance of a task with an interference at the user interface, requiring a first response from the individual to the first instance of the task in the presence of the interference;
   present via the user interface the first instance of the task, requiring a second response from the individual to the first instance of the task in the absence of the interference;
   wherein:
   at least one of the first instance of the task and the interference comprises a computerized element;
   measure substantially simultaneously the first response from the individual to the first instance of the task and the response from the individual to the interference;
   receive data indicative of the first response and the second response; and
   analyze the data indicative of the first response and the second response to compute at least one performance metric comprising at least one quantified indicator of cognitive abilities of the individual.

8. The system of claim 6, wherein the personalized cognitive treatment recommendation comprises a spatial navigation tool and the one or more processors are further configured to:
   generate a user interface;
   present via the user interface a first task that requires navigation of a specified route through an environment;
   present via the user interface a first indicator configured to navigate the specified route from an initial point in the environment to a target endpoint with or without input from the individual;
   configure the user interface to display instructions to the individual to perform a second task, the second task requiring the individual either: (i) to navigate a reverse of at least a portion of the specified route, or (ii) to navigate at least a portion of the specified route at least one additional time;
   present via the user interface a second indicator configured to navigate in the environment in response to physical actions of the individual to control one of (i) a relative direction of the second indicator, or (ii) a speed of movement of the second indicator, or (iii) both (i) and (ii), to perform the second task;
   obtain measurement data by measuring data indicative of the physical actions of the individual to control the second indicator in performing the second task; and
   analyze the measurement data to generate a performance metric for the performance of the second task, the performance metric providing an indication of a cognitive ability of the individual.

9. The system of claim 6, wherein the personalized cognitive treatment recommendation comprises an emotional processing tool and the one or more processors are further configured to:
   generate a user interface;
   present via the user interface a first instance of a task with an interference at the user interface, requiring a first response from the individual to the first instance of the task in the presence of the interference and a response from the individual to at least one evocative element;
   wherein:
   at least one of the first instance of the task and the interference comprises the at least one evocative element;
   measure substantially simultaneously (i) the first response from the individual to the first instance of the task and (ii) the response from the individual to the at least one evocative element, providing a measure of emotional processing capabilities of the individual under emotional load;
   receive data indicative of the first response and the response of the individual to the at least one evocative element; and
   analyze the data indicative of the first response and the response of the individual to the at least one evocative element to compute at least one performance metric comprising at least one quantified indicator of cognitive abilities of the individual under emotional load.

10. A computer-implemented method for generating a personalized cognitive treatment recommendation for an individual, the method comprising:
    using one or more processors to execute instructions stored in one or more memory storage devices comprising computer executable instructions to perform operations including:
    a) receive parameters for at least one cognitive treatment tool;
    b) receive at least one of physiological data indicative of a condition of the individual, or clinical data associated with the individual;
    c) generate a personalized cognitive treatment recommendation based on at least one of the physiological data or the clinical data, the personalized cognitive treatment recommendation comprising a first specification for at least one first computerized cognitive treatment tool and a second specification for at least one second computerized cognitive treatment tool,
       wherein the at least one first computerized cognitive treatment tool comprises a first cognitive treatment engine configured to target a first brain region of the individual,
       wherein the at least one second computerized cognitive treatment tool comprises a second cognitive treatment engine configured to target a second brain region of the individual,
       wherein the first brain region and the second brain region are selected from the group consisting of prefrontal cortex, extended hippocampal network, amygdala-dependent network, caudate nucleus, and entorhinal cortex region,
       wherein the first brain region is different from the second brain region,
       wherein the first specification comprises a first calculated percentage of a first set of computerized stimuli or interactions to be presented in an instance of the personalized cognitive treatment and the second specification comprises a second calculated percentage of a second set of computerized stimuli or interactions to be presented in the instance of the personalized cognitive treatment,
       wherein the instance of the personalized cognitive treatment comprises a particular graphical output of the personalized cognitive treatment, wherein the first set of computerized stimuli or interactions comprises a first set of tasks associated with the first brain region, wherein the second set of computerized stimuli or interactions comprises a second set of tasks associated with the second brain region;

d) configure the instance of the personalized cognitive treatment for the individual according to the first specification and the second specification; and e) present the instance of the personalized cognitive treatment to the individual at a graphical user interface of an end user device, wherein the instance of the personalized cognitive treatment is configured to render or modify one or more graphical elements in the first set of computerized stimuli or interactions according to the first specification and render or modify one or more graphical elements in the second set of computerized stimuli or interactions according to the second specification.

11. The method of claim 10, wherein the operations further include:
receive performance data indicative of the individual's performance of at least one task associated with the at least one first computerized cognitive treatment tool or the at least one second computerized cognitive treatment tool.

12. The method of claim 10, wherein the operations further include:
d) repeat steps b) and c) after the individual performs the instance of the personalized cognitive treatment, wherein data received during the repetition of step b) comprises data collected subsequent to the individual's performance of at least one task associated with the at least one first computerized cognitive treatment tool or the at least one second computerized cognitive treatment tool.

13. The method of claim 12, wherein the operations further include:
monitor a status of the condition of the individual based on an analysis of the at least one of the physiological data, the clinical data, or data indicative of an interaction of the individual with at least one cognitive monitoring tool;
wherein data received during the repetition of step b) comprises data indicative of the status of the condition based on the monitoring.

14. The method of claim 10, wherein generating the personalized cognitive treatment recommendation comprises using a predictive model that is trained using a plurality of training datasets, each training dataset in the plurality of training datasets corresponding to a previously classified individual of a plurality of individuals, and each training dataset comprising data representing at least one indicator of a cognitive ability of the classified individual and data indicative of a diagnosis of a status or progression of the condition in the classified individual.

15. The method of claim 10, wherein the operations further include:
monitor a status of the condition of the individual based on an analysis of at the least one of the physiological data, the clinical data, or data indicative of an interaction of the individual with the at least one cognitive treatment tool.

16. The method of claim 10, wherein the at least one cognitive treatment tool comprises at least one of an interference processing tool, a spatial navigation tool, or an emotional processing tool.

17. The method of claim 16, wherein the personalized cognitive treatment recommendation comprises an interference processing tool and the operations further include:
generate a user interface;
present via the user interface a first instance of a task with an interference at the user interface, requiring a first response from the individual to the first instance of the task in the presence of the interference;
present via the user interface the first instance of the task, requiring a second response from the individual to the first instance of the task in the absence of the interference; wherein:
at least one of the first instance of the task and the interference comprises a computerized element;
measure substantially simultaneously the first response from the individual to the first instance of the task and the response from the individual to the interference;
receive data indicative of the first response and the second response; and
analyze the data indicative of the first response and the second response to compute at least one performance metric comprising at least one quantified indicator of cognitive abilities of the individual.

18. The method of claim 16, wherein the personalized cognitive treatment recommendation comprises a spatial navigation tool and the operations further include:
generate a user interface;
present via the user interface a first task that requires navigation of a specified route through an environment;
present via the user interface a first indicator configured to navigate the specified route from an initial point in the environment to a target end-point with or without input from the individual;
configure the user interface to display instructions to the individual to perform a second task, the second task requiring the individual either: (i) to navigate a reverse of at least a portion of the specified route, or (ii) to navigate at least a portion of the specified route at least one additional time;
present via the user interface a second indicator configured to navigate in the environment in response to physical actions of the individual to control one of (i) a relative direction of the second indicator, or (ii) a speed of movement of the second indicator, or (iii) both (i) and (ii), to perform the second task;
obtain measurement data by measuring data indicative of the physical actions of the individual to control the second indicator in performing the second task; and
analyze the measurement data to generate a performance metric for the performance of the second task, the performance metric providing an indication of the cognitive ability of the individual.

19. The method of claim 16, wherein the personalized cognitive treatment recommendation comprises an emotional processing tool and the operations further include:
generate a user interface;
present via the user interface a first instance of a task with an interference at the user interface, requiring a first response from the individual to the first instance of the task in the presence of the interference and a response from the individual to at least one evocative element; wherein:
at least one of the first instance of the task and the interference comprises the at least one evocative element;
measure substantially simultaneously (i) the first response from the individual to the first instance of the task and (ii) the response from the individual to the at least one evocative element, providing a measure of emotional processing capabilities of the individual under emotional load;

receive data indicative of the first response and the response of the individual to the at least one evocative element; and analyze the data indicative of the first response and the response of the individual to the at least one evocative element to compute at least one performance metric comprising at least one quantified indicator of cognitive abilities of the individual under emotional load.

20. A non-transitory computer-readable medium encoded with instructions for commanding one or more processors to execute operations of a method for generating a personalized cognitive treatment recommendation for an individual, the operations comprising:

a) receive parameters for at least one cognitive treatment tool;

b) receive at least one of physiological data indicative of a condition of the individual, or clinical data associated with the individual;

c) generate a personalized cognitive treatment recommendation based on at least one of the physiological data or the clinical data, the personalized cognitive treatment recommendation comprising a first specification for at least one first computerized cognitive treatment tool and a second specification for at least one second computerized cognitive treatment, wherein the at least one first computerized cognitive treatment tool comprises a first cognitive treatment engine configured to target a first brain region of the individual, wherein the at least one second computerized cognitive treatment tool comprises a second cognitive treatment engine configured to target a second brain region of the individual, wherein the first brain region and the second brain region are selected from the group consisting of prefrontal cortex, extended hippocampal network, amygdala-dependent network, caudate nucleus, and entorhinal cortex region, wherein the first brain region is different from the second brain region, wherein the first specification comprises a first calculated percentage of a first set of computerized stimuli or interactions to be presented in an instance of the personalized cognitive treatment and the second specification comprises a second calculated percentage of a second set of computerized stimuli or interactions to be presented in the instance of the personalized cognitive treatment, wherein the instance of the personalized cognitive treatment comprises a particular graphical output of the personalized cognitive treatment, wherein the first set of computerized stimuli or interactions comprises a first set of tasks associated with the first brain region, wherein the second set of computerized stimuli or interactions comprises a second set of tasks associated with the second brain region;

d) configure the instance of the personalized cognitive treatment for the individual according to the first specification and the second specification; and e) present the instance of the personalized cognitive treatment to the individual at a graphical user interface of an end user device, wherein the instance of the personalized cognitive treatment is configured to render or modify one or more graphical elements in the first set of computerized stimuli or interactions according to the first specification and render or modify one or more graphical elements in the second set of computerized stimuli or interactions according to the second specification.

* * * * *